United States Patent
Kurihara et al.

(10) Patent No.: US 12,232,420 B2
(45) Date of Patent: Feb. 18, 2025

(54) ORGANIC COMPOUND, LIGHT-EMITTING ELEMENT, LIGHT-EMITTING DEVICE, ELECTRONIC DEVICE, AND LIGHTING DEVICE

(71) Applicant: SEMICONDUCTOR ENERGY LABORATORY CO., LTD., Atsugi (JP)

(72) Inventors: Miki Kurihara, Kanagawa (JP); Hideko Yoshizumi, Kanagawa (JP); Satomi Watabe, Kanagawa (JP); Hiromitsu Kido, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 276 days.

(21) Appl. No.: 17/981,689

(22) Filed: Nov. 7, 2022

(65) Prior Publication Data
US 2023/0112454 A1    Apr. 13, 2023

Related U.S. Application Data

(63) Continuation of application No. 16/493,842, filed as application No. PCT/IB2018/051455 on Mar. 7, 2018, now Pat. No. 11,495,753.

(30) Foreign Application Priority Data

Mar. 16, 2017    (JP) .................................. 2017-051536

(51) Int. Cl.
H01L 51/00    (2006.01)
C07D 491/048    (2006.01)
(Continued)

(52) U.S. Cl.
CPC ..... H10K 85/6576 (2023.02); C07D 491/048 (2013.01); H10K 85/657 (2023.02);
(Continued)

(58) Field of Classification Search
None
See application file for complete search history.

(56) References Cited

U.S. PATENT DOCUMENTS 7,906,226 B2    3/2011    Matsuura et al.
8,105,701 B2    1/2012    Matsuura et al.
(Continued)

FOREIGN PATENT DOCUMENTS

CN    105103327 A    11/2015
CN    106397460 A    2/2017
(Continued)

OTHER PUBLICATIONS

Vanitha.G et al., "Synthesis of novel antimicrobial agents encompassing naphthofuran, pyrimidine and thiadiazole moieties", Journal of Chemical and Pharmaceutical Research, 2013, vol. 5, No. 7, pp. 75-79.
(Continued)

*Primary Examiner* — Robert S Loewe
(74) *Attorney, Agent, or Firm* — Fish & Richardson P.C.

(57) ABSTRACT

A novel organic compound is provided. That is, a novel organic compound that is effective in improving reliability of a light-emitting element is provided. The organic compound includes a condensed ring including a pyrimidine ring and is represented by General Formula (G1). In General Formula (G1), A represents a group having 6 to 100 carbon atoms and includes at least one of an aromatic ring and a heteroaromatic ring. The aromatic ring and the heteroaromatic ring may each include a substituent. Furthermore, Q represents oxygen or sulfur. A ring X represents a substituted
(Continued)

or unsubstituted naphthalene ring or a substituted or unsubstituted phenanthrene ring.

13 Claims, 18 Drawing Sheets

(51) Int. Cl.
  *H10K 85/60* (2023.01)
  *H10K 50/11* (2023.01)
  *H10K 59/12* (2023.01)
  *H10K 71/16* (2023.01)
(52) U.S. Cl.
  CPC .............. *H10K 50/11* (2023.02); *H10K 59/12* (2023.02); *H10K 71/164* (2023.02)

(56) References Cited

U.S. PATENT DOCUMENTS

| | | | |
|---|---|---|---|
| 8,470,455 | B2 | 6/2013 | Matsuura et al. |
| 9,331,288 | B2 | 5/2016 | Park et al. |
| 9,570,689 | B2 | 2/2017 | Park et al. |
| 10,381,574 | B2 | 8/2019 | Jang et al. |
| 10,734,588 | B2 | 8/2020 | Park et al. |
| 11,127,905 | B2 | 9/2021 | Xia et al. |
| 11,299,459 | B2 | 4/2022 | Mun et al. |
| 2010/0160630 | A1 | 6/2010 | Nakazawa et al. |
| 2014/0291645 | A1 | 10/2014 | Inoue et al. |
| 2015/0207082 | A1 | 7/2015 | Dyatkin et al. |
| 2016/0013421 | A1 | 1/2016 | Inoue et al. |
| 2016/0141515 | A1 | 5/2016 | Hayama et al. |
| 2016/0268534 | A1* | 9/2016 | Hosoumi ............... H10K 50/11 |
| 2016/0336519 | A1* | 11/2016 | Seo ..................... H10K 85/6572 |
| 2016/0351829 | A1 | 12/2016 | Hosoumi et al. |
| 2016/0351833 | A1 | 12/2016 | Hosoumi et al. |
| 2017/0012207 | A1* | 1/2017 | Seo ..................... H10K 2101/10 |
| 2017/0025615 | A1* | 1/2017 | Seo ..................... H10K 85/611 |
| 2017/0033295 | A1* | 2/2017 | Xia ..................... H10K 85/6572 |
| 2017/0141331 | A1 | 5/2017 | Kim et al. |
| 2017/0200903 | A1 | 7/2017 | Park et al. |
| 2017/0271610 | A1* | 9/2017 | Takahashi ............... H10K 50/16 |
| 2018/0251473 | A1* | 9/2018 | Mun ..................... C07D 209/88 |
| 2018/0282276 | A1* | 10/2018 | Mun ..................... C07D 209/82 |
| 2019/0019962 | A1 | 1/2019 | Mun et al. |
| 2019/0103561 | A1 | 4/2019 | Jang et al. |
| 2019/0131537 | A1* | 5/2019 | Kim ..................... H10K 85/636 |
| 2019/0131543 | A1* | 5/2019 | Lee ..................... C07D 487/04 |
| 2019/0135730 | A1* | 5/2019 | Mun ..................... C07D 471/04 |
| 2021/0376256 | A1 | 12/2021 | Xia et al. |

FOREIGN PATENT DOCUMENTS

| | | | |
|---|---|---|---|
| CN | 106661038 | A | 5/2017 |
| EP | 3124488 | A | 2/2017 |
| JP | 2010-182699 | A | 8/2010 |
| JP | 2014-209611 | A | 11/2014 |
| JP | 2016-028421 | A | 2/2016 |
| JP | 2016-147897 | A | 8/2016 |
| JP | 2016-174161 | A | 9/2016 |
| JP | 2017-031138 | A | 2/2017 |
| JP | 2017-098561 | A | 6/2017 |
| JP | 2017-210483 | A | 11/2017 |
| KR | 2015-0132837 | A | 11/2015 |
| KR | 2015-0136942 | A | 12/2015 |
| KR | 2016-0007380 | A | 1/2016 |
| KR | 2016-0017530 | A | 2/2016 |
| KR | 2017-0015216 | A | 2/2017 |
| KR | 2017-0022505 | A | 3/2017 |
| KR | 2017-0082377 | A | 7/2017 |
| TW | 201443058 | | 11/2014 |
| TW | 201605863 | | 2/2016 |
| WO | WO-2014/157599 | | 10/2014 |
| WO | WO-2016/021815 | | 2/2016 |
| WO | WO-2017/119654 | | 7/2017 |

OTHER PUBLICATIONS

Badr.M et al., "Synthesis and biological study of some new naphtho [2,1-b] furan and related heterocyclic systems", Journal of Chemical Research, Nov. 1, 2006, vol. 2006, No. 11, pp. 748-752.
Padmashali.B et al., "Synthesis of Novel Angularly Fused Pentacyclic Heterocycles of Pharmacological Interest", Indian Journal of Chemistry Section B, Jul. 1, 2005, vol. 44B, No. 7, pp. 1446-1451.
International Search Report (Application No. PCT/IB2018/051455) dated Jul. 3, 2018.
Written Opinion (Application No. PCT/IB2018/051455) dated Jul. 3, 2018.
Chinese Office Action (Application No. 201880016674.7) dated May 31, 2022.

* cited by examiner

ORGANIC COMPOUND, LIGHT-EMITTING ELEMENT, LIGHT-EMITTING DEVICE, ELECTRONIC DEVICE, AND LIGHTING DEVICE

CROSS REFERENCE TO RELATED APPLICATIONS

This application is a continuation of U.S. application Ser. No. 16/493,842, filed Sep. 13, 2019, now allowed, which is a U.S. National Phase Application under 35 U.S.C. § 371 of International Application PCT/IB2018/051455, filed on Mar. 7, 2018, and claims the benefit of a foreign priority application filed in Japan as Application No. 2017-051536 on Mar. 16, 2017, all of which are incorporated by reference.

TECHNICAL FIELD

One embodiment of the present invention relates to an organic compound, a light-emitting element, a light-emitting device, an electronic device, and a lighting device. Note that one embodiment of the present invention is not limited to the above technical field. That is, one embodiment of the present invention relates to an object, a method, a manufacturing method, or a driving method. In addition, one embodiment of the present invention relates to a process, a machine, manufacture, and a composition of matter. Specific examples include a semiconductor device, a display device, and a liquid crystal display device.

BACKGROUND ART

A light-emitting element including an EL layer between a pair of electrodes (also referred to as an organic EL element) has characteristics such as thinness, light weight, high-speed response to input signals, and low power consumption, and a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the spectrum of light emitted from a light-emitting substance depends on the light-emitting substance, the use of different types of organic compounds as light-emitting substances makes it possible to obtain light-emitting elements which exhibit various colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

DISCLOSURE OF INVENTION

In development of light-emitting elements, organic compounds used in the light-emitting element are very important for improving reliability. Thus, an object of one embodiment of the present invention is to provide a novel organic compound. That is, an object is to provide a novel organic compound that is effective in improving reliability of a light-emitting element. Another object of one embodiment of the present invention is to provide a novel organic compound that can be used in a light-emitting element. Another object of one embodiment of the present invention is to provide a novel organic compound that can be used in an EL layer of a light-emitting element. Another object is to provide a highly reliable and novel light-emitting element using a novel organic compound of one embodiment of the present invention. Another object is to provide a novel light-emitting device, a novel electronic device, or a novel lighting device. Note that the description of these objects does not disturb the existence of other objects. In one embodiment of the present invention, there is no need to achieve all the objects. Other objects will be apparent from and can be derived from the description of the specification, the drawings, the claims, and the like.

One embodiment of the present invention is an organic compound that includes a condensed ring including a pyrimidine ring and is represented by General Formula (G1).

[Chemical Formula 1]

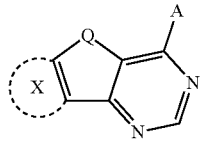

(G1)

In General Formula (G1), A represents a group having 6 to 100 carbon atoms and includes at least one of an aromatic ring and a heteroaromatic ring. Note that the aromatic ring and the heteroaromatic ring may each include a substituent. Furthermore, Q represents oxygen or sulfur. A ring X represents a substituted or unsubstituted naphthalene ring or a substituted or unsubstituted phenanthrene ring.

In the above structure, A preferably includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure, and the rings and the structure each preferably include a substituent.

Another embodiment of the present invention is an organic compound represented by General Formula (G2) below.

[Chemical Formula 2]

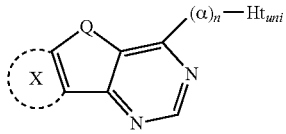

(G2)

In General Formula (G2), a represents a substituted or unsubstituted phenylene group, and n represents an integer of 0 to 4. In addition, $Ht_{uni}$ represents a hole-transport skeleton. Furthermore, Q represents oxygen or sulfur. A ring X represents a substituted or unsubstituted naphthalene ring or a substituted or unsubstituted phenanthrene ring.

Another embodiment of the present invention is an organic compound represented by General Formula (G3) below.

[Chemical Formula 3]

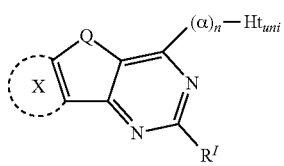

(G3)

In General Formula (G3), a represents a substituted or unsubstituted phenylene group, and n represents an integer of 1 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. Moreover, Q represents oxygen or sulfur. A ring X represents a substituted or unsubstituted naphthalene ring or a substituted or unsubstituted phenanthrene ring.

Another embodiment of the present invention is an organic compound represented by General Formula (G4) below.

[Chemical Formula 4]

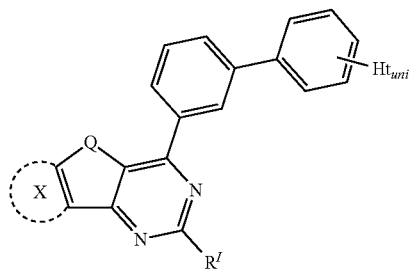

(G4)

In General Formula (G4), $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. In addition, Q represents oxygen or sulfur. A ring X represents a substituted or unsubstituted naphthalene ring or a substituted or unsubstituted phenanthrene ring.

Another embodiment of the present invention is an organic compound represented by General Formula (G5) below.

[Chemical Formula 5]

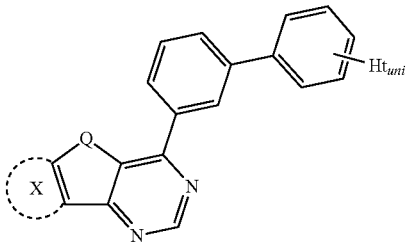

(G5)

In General Formula (G5), $Ht_{uni}$ represents a hole-transport skeleton. Furthermore, Q represents oxygen or sulfur. A ring X represents a substituted or unsubstituted naphthalene ring or a substituted or unsubstituted phenanthrene ring.

The organic compounds of embodiments of the present invention that are represented by General Formulae (G2) to (G5) each preferably include a hole-transport skeleton ($Ht_{uni}$). Note that $Ht_{uni}$ preferably has a pyrrole ring structure, a furan ring structure, or a thiophene ring structure. Specifically, $Ht_{uni}$ preferably has a structure represented by any one of General Formulae (Ht-1) to (Ht-7).

[Chemical Formulae 6]

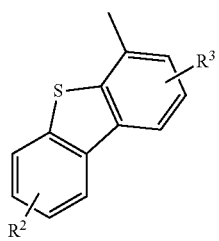

(Ht-1)

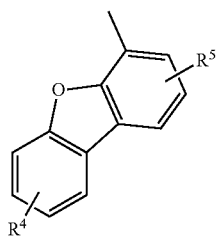

(Ht-2)

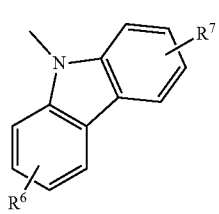

(Ht-3)

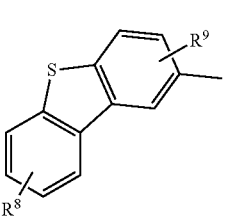

(Ht-4)

(Ht-5)
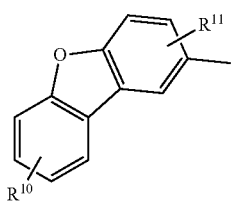

(Ht-6)
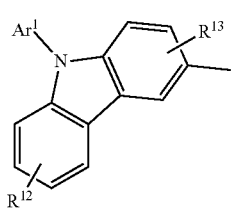

(Ht-7)
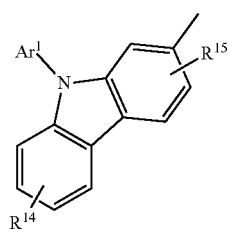

In General Formulae (Ht-1) to (Ht-7), $R^2$ to $R^{15}$ each represent 1 to 4 substituents and independently represent any one of hydrogen, an alkyl group having 1 to 6 carbon atoms, and a substituted or unsubstituted phenyl group. Furthermore, $Ar^1$ represents a substituted or unsubstituted aryl group having 6 to 13 carbon atoms.

The ring X in General Formulae (G1) to (G5) is represented by any one of General Formulae (X-1) to (X-4) and is condensed with an adjacent ring at a position represented by a.

[Chemical Formulae 7]

(X-1)
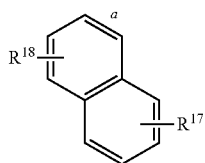

(X-2)
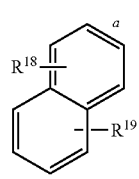

(X-3)
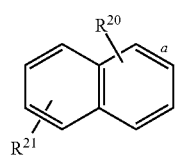

(X-4)
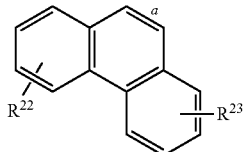

In General Formulae (X-1) to (X-4), $R^{16}$ to $R^{23}$ each represent 1 to 4 substituents and independently represent any one of hydrogen, an alkyl group having 1 to 6 carbon atoms, and a substituted or unsubstituted phenyl group.

One embodiment of the present invention is the organic compound that includes a condensed ring including a pyrimidine ring, that is, the organic compound preferably has a structure in which a specific ring structure is condensed with a hetero ring condensed with the pyrimidine ring. Note that the specific ring structure refers to the structure of the ring X in General Formulae (G1) to (G5) and preferably refers to, for example, any of the structures represented by General Formulae (X-1) to (X-4).

One embodiment of the present invention is the organic compound that includes a condensed ring including a pyrimidine ring, and the organic compound may further include a hole-transport skeleton ($Ht_{uni}$). Note that the organic compound of one embodiment of the present invention having such a structure has a bipolar property owing to a hole-transport property of $Ht_{uni}$ and an electron-transport property of the condensed ring including the pyrimidine ring. When the organic compound of one embodiment of the present invention has a bipolar property, the use of the organic compound as a host material is very effective in fabricating a light-emitting element because the range of choices for guest materials to be combined with the host material is widened. The hole-transport skeleton ($Ht_{uni}$) preferably has a pyrrole ring structure, a furan ring structure, a thiophene ring structure, or the like. Further preferably, the hole-transport skeleton ($Ht_{uni}$) has a structure represented by any one of General Formulae (Ht-1) to (Ht-7).

One embodiment of the present invention is the organic compound that includes a condensed ring including a pyrimidine ring. When the condensed ring including a pyrimidine ring includes a condensed ring such as a substituted or unsubstituted naphthalene ring or a substituted or unsubstituted phenanthrene ring, the LUMO is widely distributed over the condensed ring and thus the organic compound is stabilized. Hence, electrical resistance to electrons is increased. In addition, stability against an exciton is increased. Therefore, the structure in which the condensed ring including a pyrimidine ring includes the condensed ring is preferably used for a transport layer and a light-emitting layer, in which case reliability of a light-emitting element is improved.

The organic compounds of embodiments of the present invention that are represented by General Formulae (G1), (G2), and (G5) in each of which a carbon atom between two nitrogen atoms that form a pyrimidine ring is bonded to a hydrogen atom as a substituent tend to have deeper LUMO levels than an organic compound in which a carbon atom is bonded to a substituent other than a hydrogen atom. Thus, an exciplex is easily formed by a plurality of host materials, and it is preferable to use an element utilizing the energy transfer from the exciplex formed by the plurality of host materials to a guest material (this energy transfer is also referred to as ExTET) because the emission efficiency can be increased.

Another embodiment of the present invention is an organic compound represented by Structural Formula (100) or Structural Formula (101).

[Chemical Formulae 8]

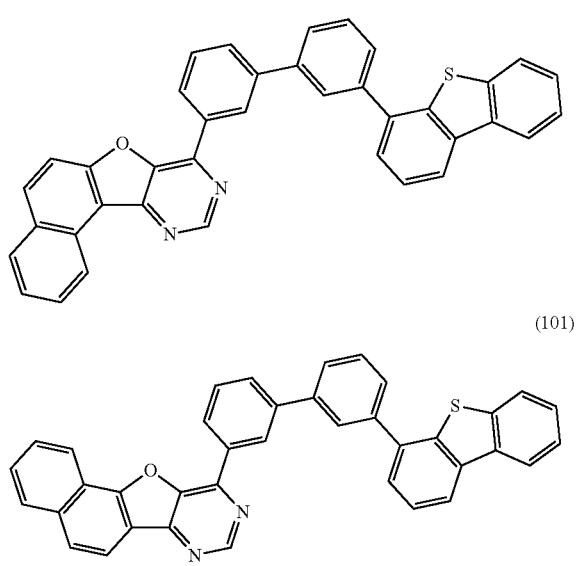

Another embodiment of the present invention is a light-emitting element formed using an organic compound that includes a condensed ring including a pyrimidine ring. The present invention also includes a light-emitting element formed using the above organic compound and a guest material.

Another embodiment of the present invention is a light-emitting element containing the organic compound of one embodiment of the present invention. Note that the present invention also includes a light-emitting element in which an EL layer provided between a pair of electrodes or a light-emitting layer included in the EL layer contains the organic compound of one embodiment of the present invention. In addition to the above light-emitting elements, a light-emitting device including a transistor, a substrate, or the like is also included in the scope of the invention. Furthermore, in addition to the light-emitting device, an electronic device and a lighting device that include a microphone, a camera, an operation button, an external connection portion, a housing, a cover, a support, a speaker, or the like are also included in the scope of the invention.

One embodiment of the present invention includes, in its scope, a light-emitting device including a light-emitting element, and a lighting device including the light-emitting device. Accordingly, the light-emitting device in this specification refers to an image display device and a light source (including a lighting device). In addition, the light-emitting device includes, in its category, all of a module in which a connector such as a flexible printed circuit (FPC) or a tape carrier package (TCP) is connected to a light-emitting device, a module in which a printed wiring board is provided at the end of a TCP, and a module in which an integrated circuit (IC) is directly mounted on a light-emitting element by a chip on glass (COG) method.

According to one embodiment of the present invention, a novel organic compound can be provided. In other words, a novel organic compound that is effective in improving reliability of a light-emitting element can be provided. According to one embodiment of the present invention, a novel organic compound that can be used in a light-emitting element can be provided. According to one embodiment of the present invention, a novel organic compound that can be used in an EL layer of a light-emitting element can be provided. According to one embodiment of the present invention, a highly reliable and novel light-emitting element using a novel organic compound of one embodiment of the present invention can be provided. In addition, a novel light-emitting device, a novel electronic device, or a novel lighting device can be provided. Note that the description of these effects does not disturb the existence of other effects. In one embodiment of the present invention, there is no need to achieve all the effects. Other effects will be apparent from and can be derived from the description of the specification, the drawings, the claims, and the like.

BRIEF DESCRIPTION OF DRAWINGS

In the accompanying drawings.

BEST MODE FOR CARRYING OUT THE INVENTION

Figure 1A:
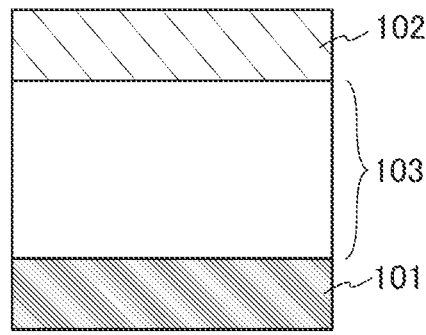
FIGS. 1A to 1E illustrate structures of light-emitting elements.

Embodiments of the present invention will be described below with reference to the drawings. Note that the present invention is not limited to the following description, and the modes and details of the present invention can be modified in various ways without departing from the spirit and scope of the present invention. Therefore, the present invention should not be construed as being limited to the description in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in the drawings and the like.

In the description of structures of the present invention in this specification and the like with reference to the drawings, the same components in different drawings are denoted by the same reference numeral.

Embodiment 1

In this embodiment, organic compounds of embodiments of the present invention will be described.

The organic compound described in this embodiment includes a condensed ring including a pyrimidine ring and has a structure represented by General Formula (G1).

[Chemical Formula 9]

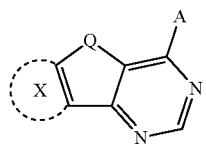

(G1)

Note that in General Formula (G1), A represents a group having 6 to 100 carbon atoms and includes at least one of an aromatic ring and a heteroaromatic ring. The aromatic ring and the heteroaromatic ring may each include a substituent. Furthermore, Q represents oxygen or sulfur. A ring X represents a substituted or unsubstituted naphthalene ring or a substituted or unsubstituted phenanthrene ring.

In General Formula (G1), A preferably includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure, and the rings and the structure each preferably include a substituent.

Typical examples of A, which is the group having 6 to 100 carbon atoms, in General Formula (G1) include groups represented by General Formulae (A-1) to (A-6). Note that the groups shown below are merely typical examples and the group having 6 to 100 carbon atoms is not limited to these examples.

[Chemical Formulae 10]

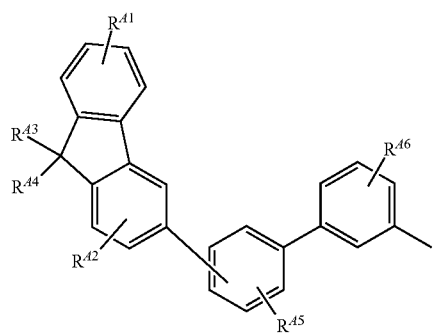

(A-1)

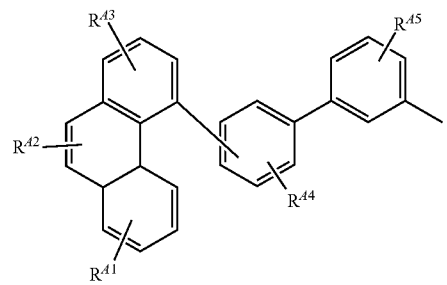

(A-2)

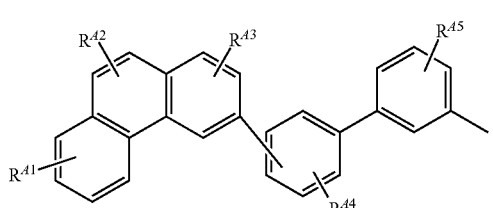

(A-3)

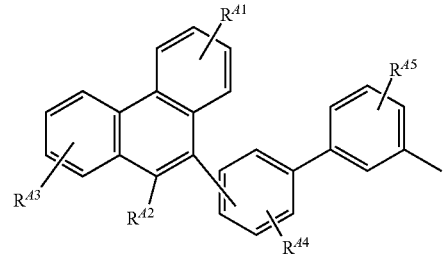

(A-4)

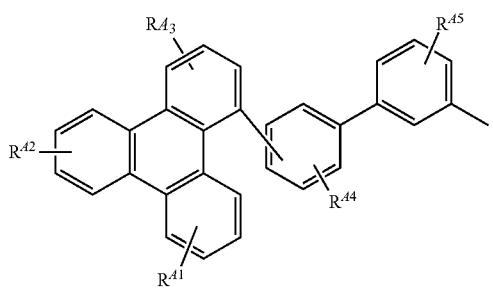

(A-5)

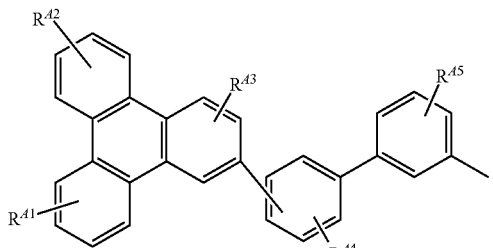

(A-6)

In General Formulae (A-1) to (A-6), $R^{A1}$ to $R^{A6}$ each represent 1 to 4 substituents, and the substituents independently represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

Other typical examples of A, which is the group having 6 to 100 carbon atoms, in General Formula (G1) include groups represented by General Formulae (A-10) to (A-25).

Note that the groups shown below are merely typical examples and A is not limited to these examples.
[Chemical Formulae 11]
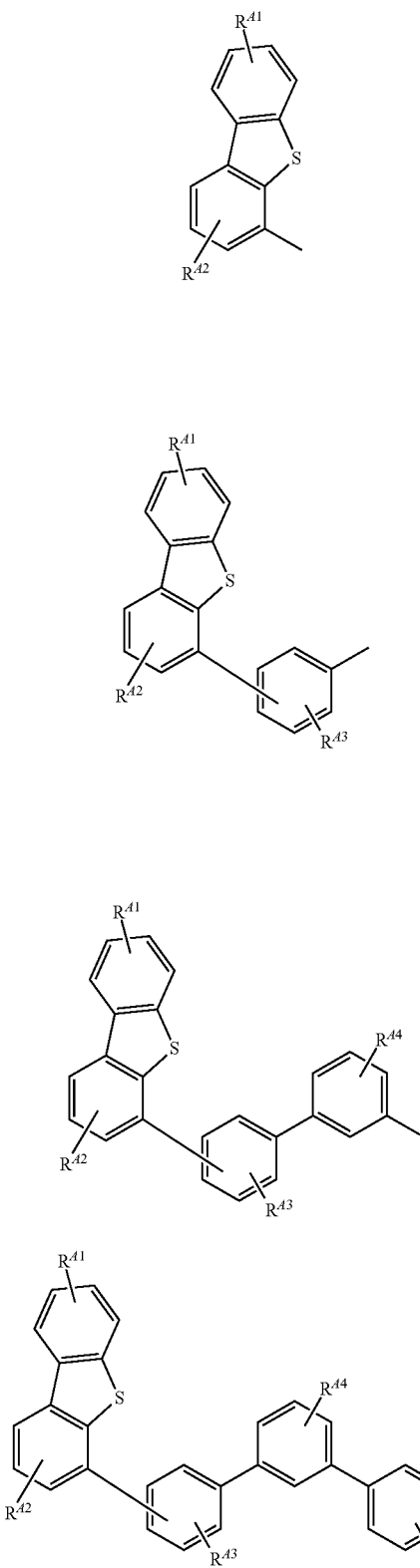
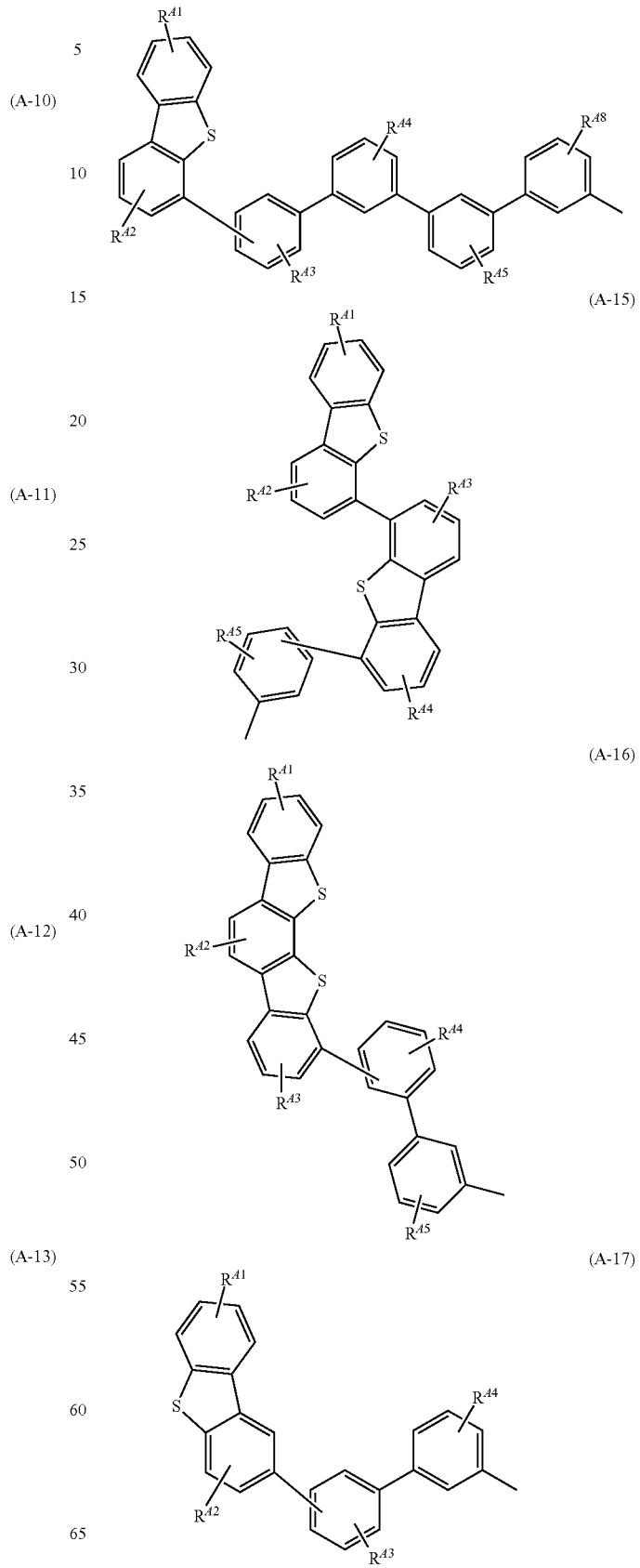

-continued

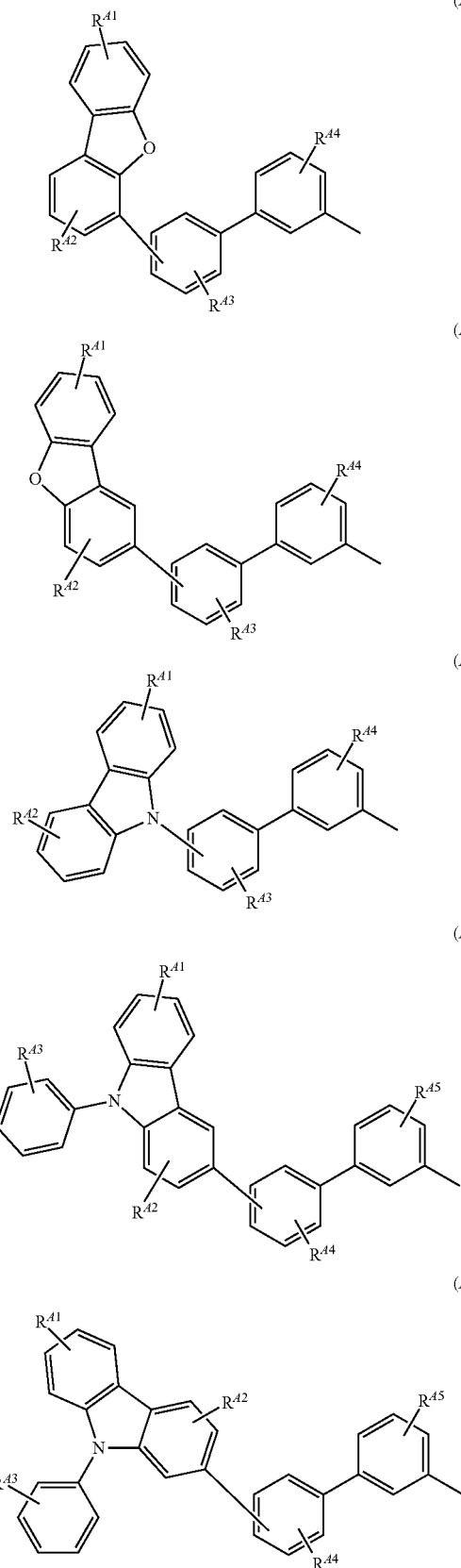

(A-18)
(A-19)
(A-20)
(A-21)
(A-22)

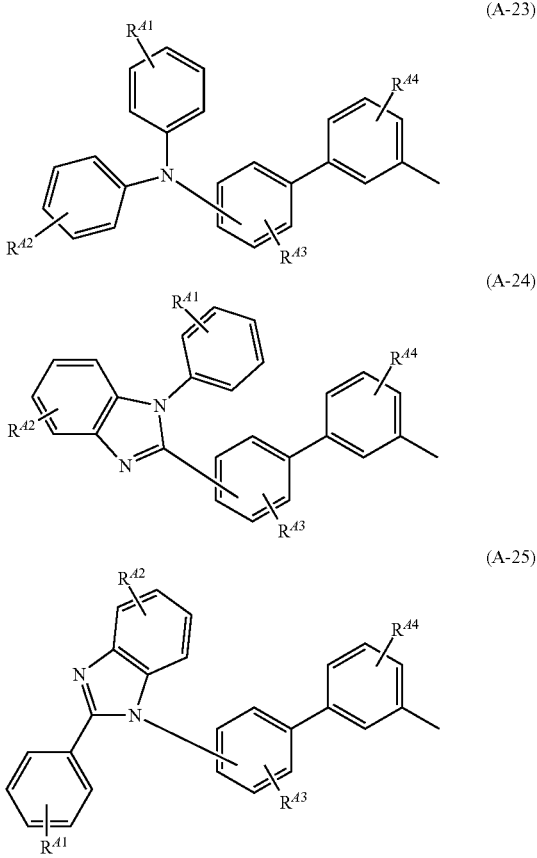

(A-23)
(A-24)
(A-25)

In General Formulae (A-10) to (A-25), $R^{A1}$ to $R^{A6}$ each represent 1 to 4 substituents, and the substituents independently represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. When $R^{A1}$ to $R^{A6}$ each represent the substituent, the substituent is assumed to be a group that does not significantly change the characteristics of the compound, such as an alkyl group having 1 to 3 carbon atoms.

Another organic compound described in this embodiment includes a condensed ring including a pyrimidine ring and has a structure represented by General Formula (G2).

[Chemical Formula 13]

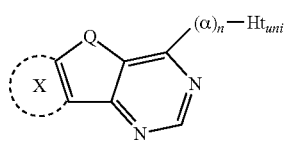

(G2)

Note that in General Formula (G2), α represents a substituted or unsubstituted phenylene group, and n represents an integer of 0 to 4. In addition, $Ht_{uni}$ represents a hole-transport skeleton. Furthermore, Q represents oxygen or sulfur. The ring X represents a substituted or unsubstituted naphthalene ring or a substituted or unsubstituted phenanthrene ring.

In General Formula (G2), to inhibit interaction between $Ht_n$ and the ring X and keep a high triplet excitation level (Ti level), n is preferably 1 or more; to improve a thermophysical property and stability of a molecule, n is preferably 2. Furthermore, when n is 2, the divalent group represented by a and n is preferably a 1,1'-biphenyl-3,3'-diyl group or a 1,1'-biphenyl-3,4'-diyl group.

Another organic compound described in this embodiment includes a condensed ring including a pyrimidine ring and has a structure represented by General Formula (G3).

[Chemical Formula 14]

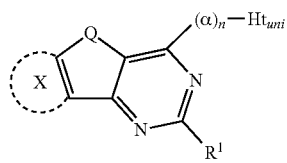

(G3)

Note that in General Formula (G3), a represents a substituted or unsubstituted phenylene group, and n represents an integer of 1 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. Moreover, Q represents oxygen or sulfur. The ring X represents a substituted or unsubstituted naphthalene ring or a substituted or unsubstituted phenanthrene ring.

In General Formula (G3), to inhibit interaction between $Ht_{uni}$ and the ring X or $R^1$ and keep a high triplet excitation level (Ti level), n is 1 or more; to improve a thermophysical property and stability of a molecule, n is preferably 2. Furthermore, when n is 2, the divalent group represented by a and n is preferably a 1,1'-biphenyl-3,3'-diyl group or a 1,1'-biphenyl-3,4'-diyl group.

Another organic compound described in this embodiment includes a condensed ring including a pyrimidine ring and has a structure represented by General Formula (G4).

[Chemical Formula 15]

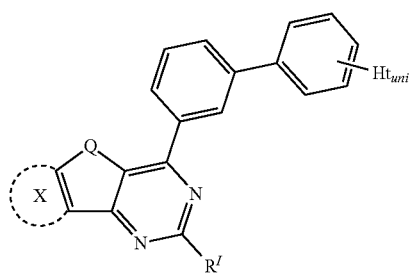

(G4)

Note that in General Formula (G4), $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. In addition, Q represents oxygen or sulfur. The ring X represents a substituted or unsubstituted naphthalene ring or a substituted or unsubstituted phenanthrene ring.

Another organic compound described in this embodiment includes a condensed ring including a pyrimidine ring and has a structure represented by General Formula (G5).

[Chemical Formula 16]

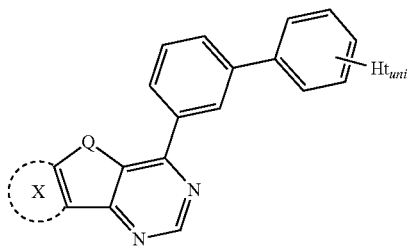

(G5)

Note that in General Formula (G5), $Ht_{uni}$ represents a hole-transport skeleton. Furthermore, Q represents oxygen or sulfur. The ring X represents a substituted or unsubstituted naphthalene ring or a substituted or unsubstituted phenanthrene ring.

In General Formulae (G2) to (G5), $Ht_{uni}$ preferably has a pyrrole ring structure, a furan ring structure, or a thiophene ring structure. Examples of a ring included in these ring structures include a pyrrole ring, a furan ring, a thiophene ring, an indole ring, an isoindole ring, a benzofuran ring, an isobenzofuran ring, a benzothiophene ring, an isobenzothiophene ring, a carbazole ring, a dibenzofuran ring, a dibenzothiophene ring, a naphthofuran ring, a naphthothiophene ring, a benzocarbazole ring, a dibenzocarbazole ring, a benzonaphthofuran ring, a benzonaphthothiophene ring, and a benzothienobenzothiophene ring. Furthermore, these rings may each include any of substituents described later.

In General Formulae (G2) to (G5), $Ht_{uni}$ preferably has a structure represented by any of General Formulae (Ht-1) to (Ht-7).

[Chemical Formulae 17]

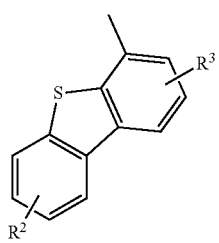

(Ht-1)

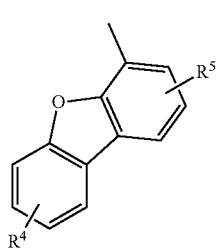

(Ht-2)

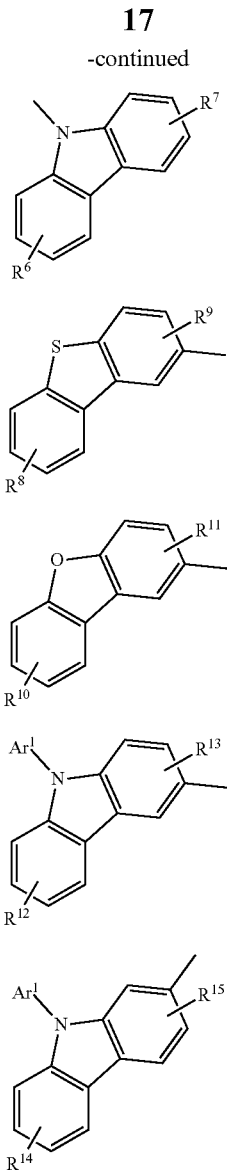

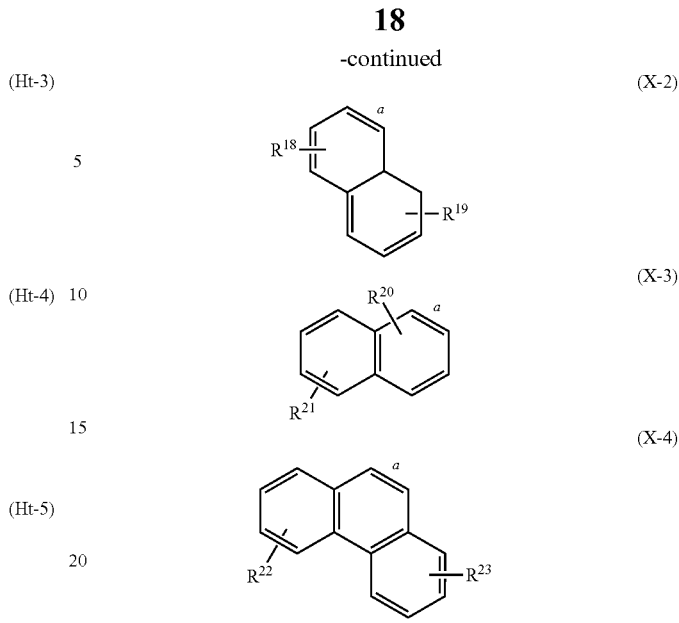

In General Formulae (Ht-1) to (Ht-7), $R^2$ to $R^{15}$ each represent 1 to 4 substituents and independently represent any one of hydrogen, an alkyl group having 1 to 6 carbon atoms, and a substituted or unsubstituted phenyl group. In addition, $Ar^1$ represents a substituted or unsubstituted aryl group having 6 to 13 carbon atoms.

The ring X in General Formulae (G1) to (G5) is represented by any one of General Formulae (X-1) to (X-4) and is condensed with an adjacent ring at a position represented by a.

[Chemical Formulae 18]

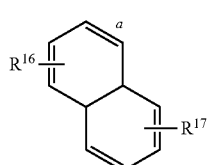

In General Formulae (X-1) to (X-4), $R^{16}$ to $R^{23}$ each represent 1 to 4 substituents and independently represent any one of hydrogen, an alkyl group having 1 to 6 carbon atoms, and a substituted or unsubstituted phenyl group.

The organic compounds of embodiments of the present invention each include a condensed ring including a pyrimidine ring. Note that a light-emitting element in which a specific ring structure is condensed with a hetero ring condensed with a pyrimidine ring can have higher reliability than a light-emitting element in which any of the ring structures other than the specific ring structure is condensed with a hetero ring condensed with a pyrimidine ring. Thus, a light-emitting element including an organic compound in which the ring X in General Formulae (G1) to (G5) is condensed with an adjacent ring (a hetero ring condensed with a pyrimidine ring) at a position a in a specific ring structure represented by any one of General Formulae (X-1) to (X-4) can have higher reliability than a light-emitting element including an organic compound in which any of the other ring structures is fused.

The organic compounds of embodiments of the present invention each include a condensed ring including a pyrimidine ring, and may further include a hole-transport skeleton ($Ht_{uni}$). Note that the organic compound having such a structure has a bipolar property owing to a hole-transport property of $Ht_{uni}$ and an electron-transport property of the condensed ring including the pyrimidine ring. When the organic compound of one embodiment of the present invention has a bipolar property, the use of the organic compound as a host material is very effective in fabricating a light-emitting element because the range of choices for guest materials to be combined with the host material is widened. The hole-transport skeleton ($Ht_{uni}$) preferably has a pyrrole ring structure, a furan ring structure, a thiophene ring structure, or the like. Specifically, the hole-transport skeleton ($Ht_{uni}$) preferably has a structure represented by any one of General Formulae (Ht-1) to (Ht-7).

In the case where any of the aromatic ring, the heteroaromatic ring, the substituted or unsubstituted naphthalene ring, and the substituted or unsubstituted phenanthrene ring in General Formula (G1); the substituted or unsubstituted phenylene group, the substituted or unsubstituted naphthalene ring, and the substituted or unsubstituted phenanthrene ring in General Formula (G2); the substituted or unsubstituted phenylene group, the substituted or unsubstituted monocyclic saturated hydrocarbon having 5 to 7 carbon atoms, the substituted or unsubstituted polycyclic saturated hydrocarbon having 7 to 10 carbon atoms, the substituted or unsubstituted aryl group having 6 to 13 carbon atoms, the substituted or unsubstituted naphthalene ring, and the substituted or unsubstituted phenanthrene ring in General Formula (G3); the substituted or unsubstituted monocyclic saturated hydrocarbon having 5 to 7 carbon atoms, the substituted or unsubstituted polycyclic saturated hydrocarbon having 7 to 10 carbon atoms, the substituted or unsubstituted aryl group having 6 to 13 carbon atoms, the substituted or unsubstituted naphthalene ring, and the substituted or unsubstituted phenanthrene ring in General Formula (G4); the substituted or unsubstituted naphthalene ring and the substituted or unsubstituted phenanthrene ring in General Formula (G5); and $Ht_{uni}$ in General Formulae (G2) to (G5) includes a substituent, examples of the substituent include an alkyl group having 1 to 6 carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group having 5 to 7 carbon atoms, such as a cyclopentyl group, a cyclohexyl group, a cycloheptyl group, a 1-norbornyl group, or a 2-norbornyl group; an aryl group having 6 to 12 carbon atoms, such as a phenyl group or a biphenyl group; and a heteroaryl group having 4 to 18 carbon atoms, such as a 9-carbazolyl group or a 9-phenyl-3-carbazolyl group.

Specific examples of the substituted or unsubstituted naphthalene ring in General Formulae (G1) to (G5) include naphthalene, 1-phenylnaphthalene, and 2-phenylnaphthalene.

Specific examples of the substituted or unsubstituted phenanthrene ring in General Formulae (G1) to (G5) include phenanthrene, 1-phenylphenanthrene, and 1,8-diphenylphenanthrene.

Specific examples of the alkyl group having 1 to 6 carbon atoms in General Formulae (A-10) to (A-25) and General Formulae (G3) and (G4) include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

Specific examples of the substituted or unsubstituted monocyclic saturated hydrocarbon having 5 to 7 carbon atoms in General Formulae (A-10) to (A-25) and General Formulae (G3) and (G4) include a cyclopropyl group, a cyclobutyl group, a cyclopentyl group, a cyclohexyl group, a cyclooctyl group, a 2-methylcyclohexyl group, and a 2,6-dimethylcyclohexyl group.

Specific examples of the substituted or unsubstituted polycyclic saturated hydrocarbon having 7 to 10 carbon atoms in General Formulae (A-10) to (A-25) and General Formulae (G3) and (G4) include a decahydronaphthyl group and an adamantyl group.

Specific examples of the substituted or unsubstituted aryl group having 6 to 13 carbon atoms in General Formulae (G3) and (G4) and General Formulae (Ht-1) to (Ht-7) include a phenyl group, a naphthyl group (a 1-naphthyl group and a 2-naphthyl group), a tolyl group (an o-tolyl group, an m-tolyl group, and a p-tolyl group), and a biphenyl group (a biphenyl-2-yl group, a biphenyl-3-yl group, and a biphenyl-4-yl group).

Next, specific structural formulae of the organic compounds of embodiments of the present invention are shown below. Note that the present invention is not limited to these formulae.

[Chemical Formulae 19]

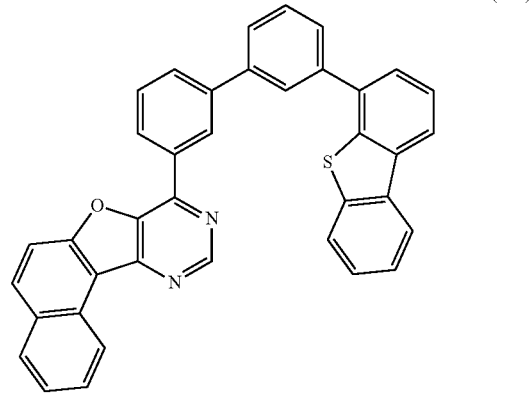

(100)

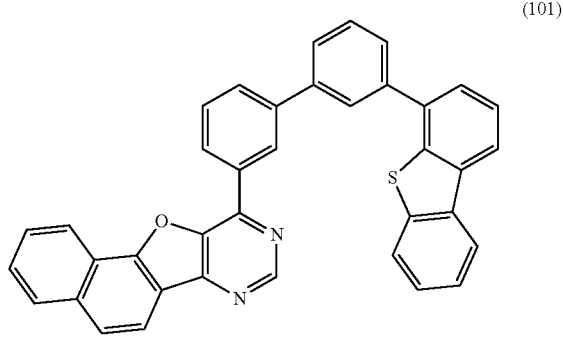

(101)

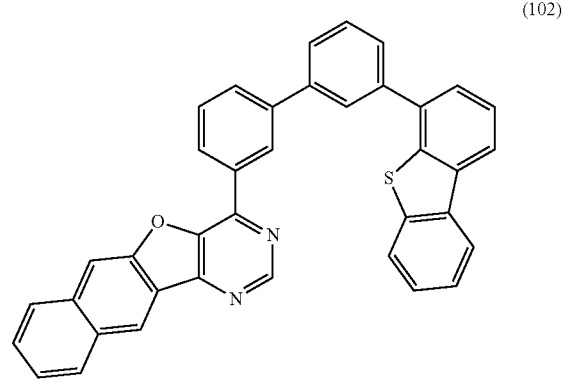

(102)

(103)
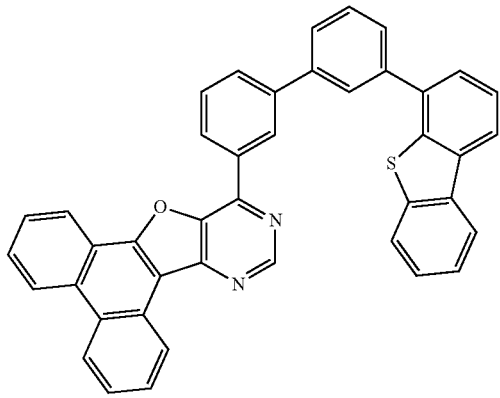
(104)
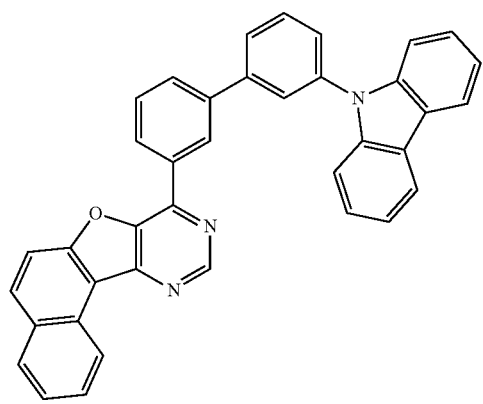
(105)
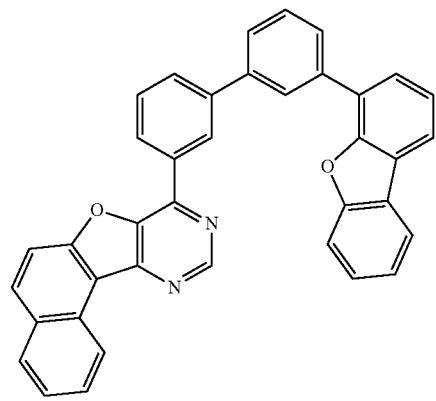
(106)
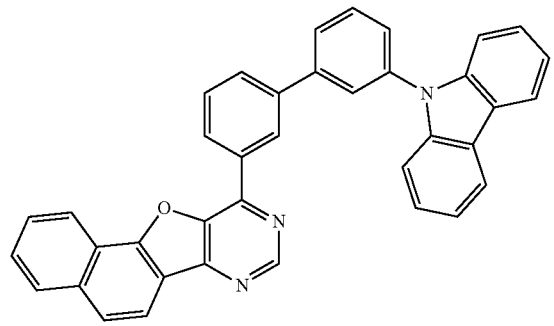
(107)
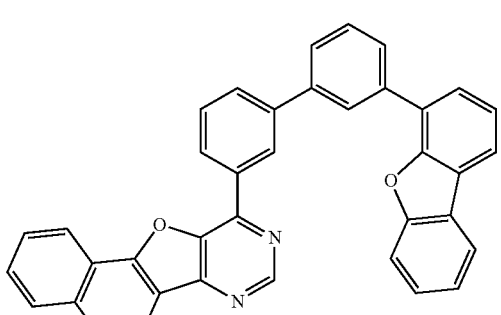
(108)
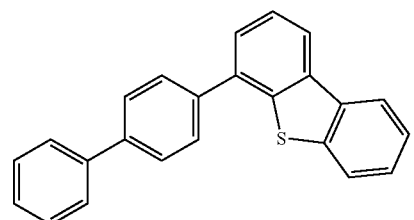
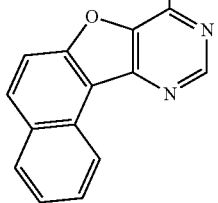
(109)
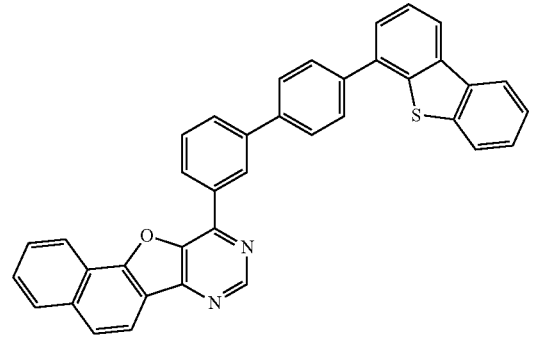

(110)
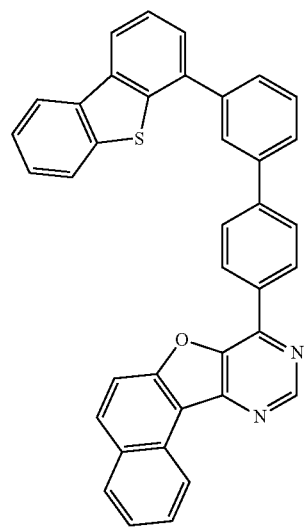
(111)
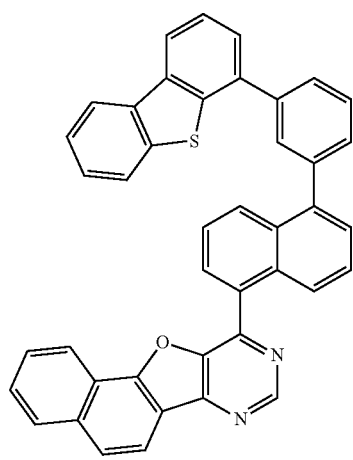
[Chemical Formulae 20]
(112)
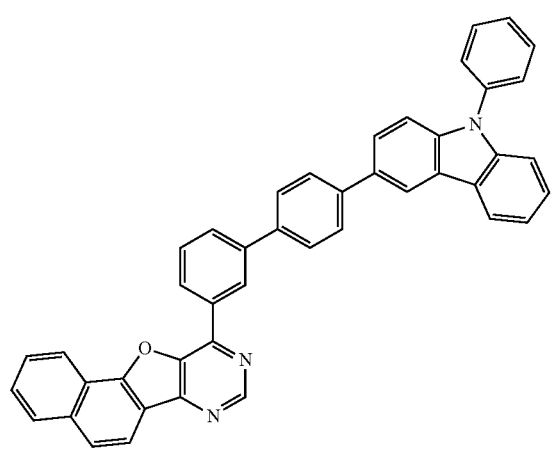
(113)
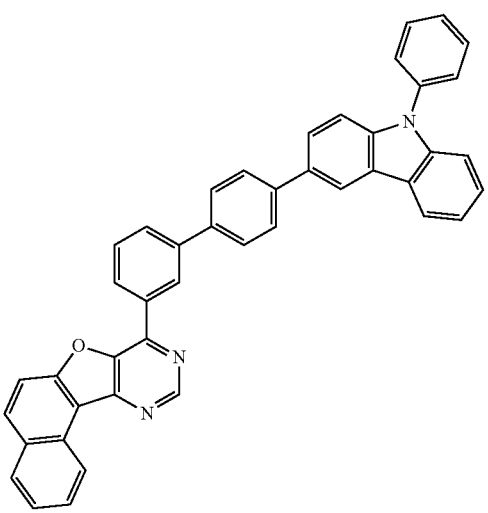
(114)
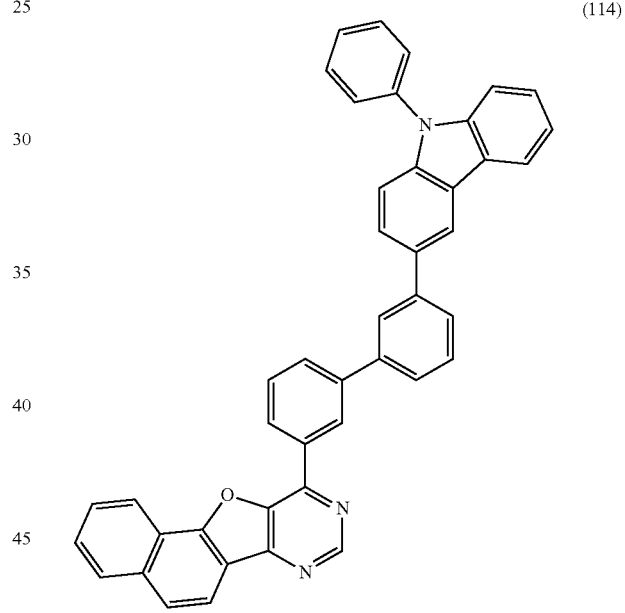
(115)
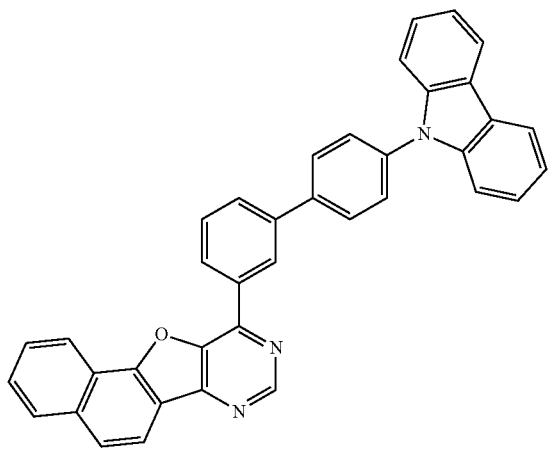

(116)
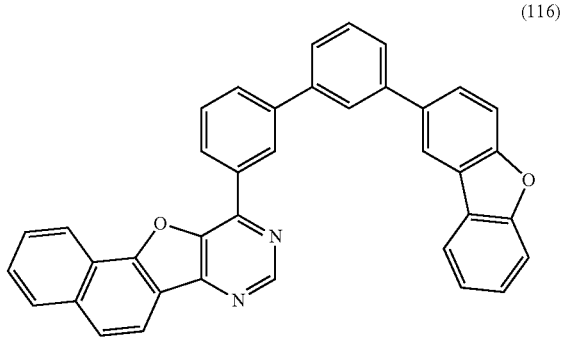
(117)
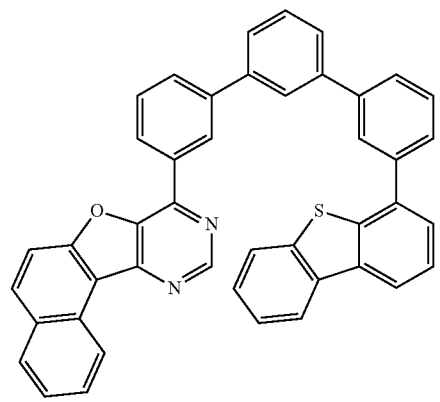
(118)
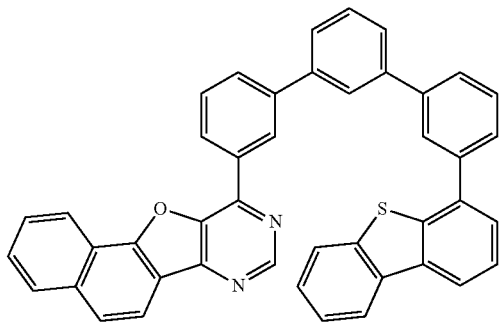
(119)
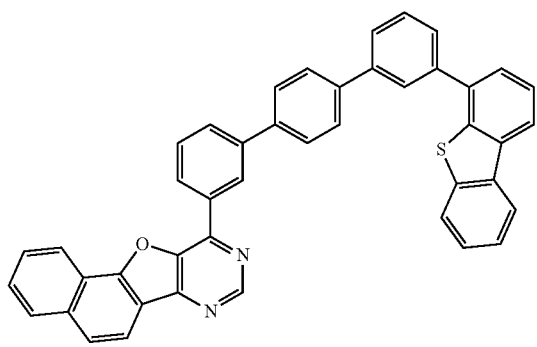
(120)
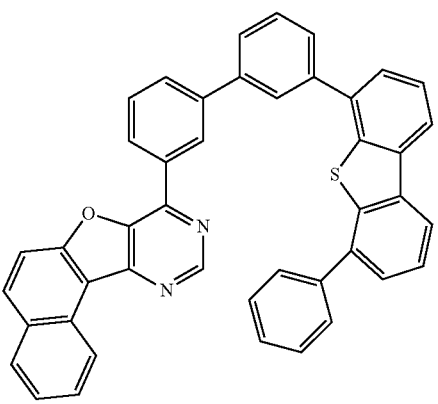
(121)
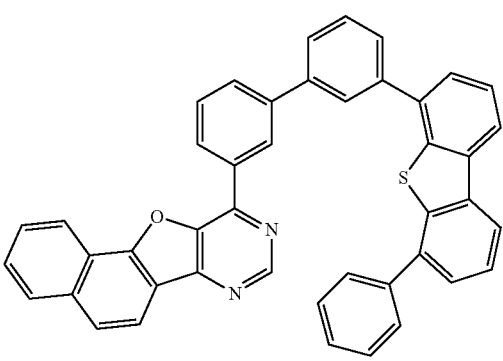
(122)
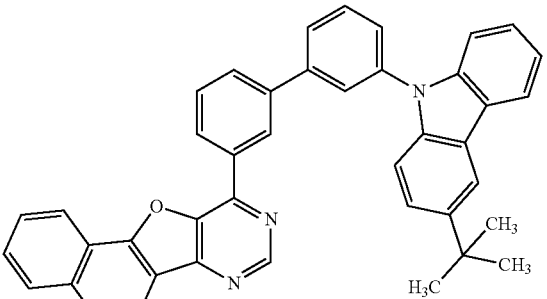
(123)
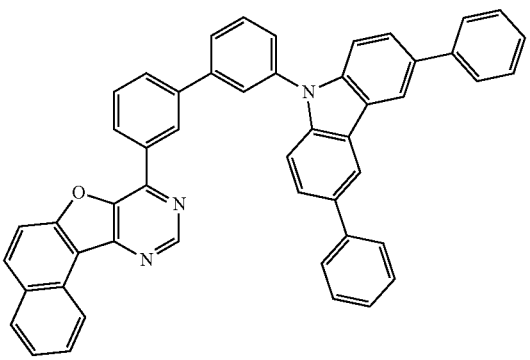

[Chemical Formulae 21]
(124)
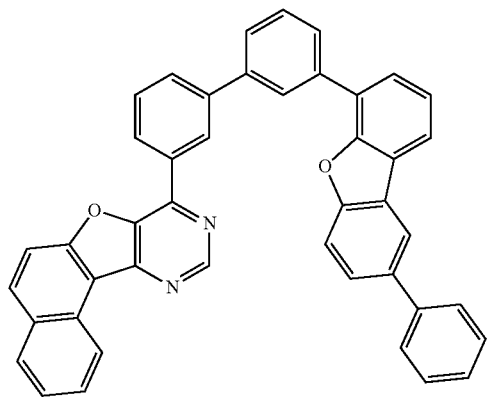
(125)
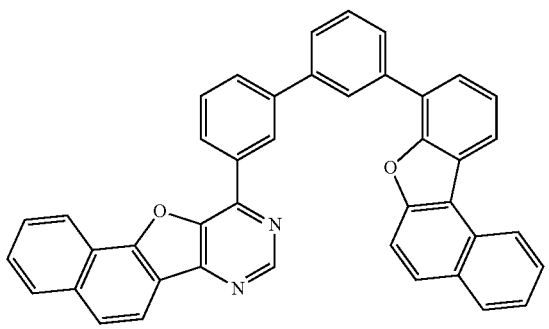
(126)
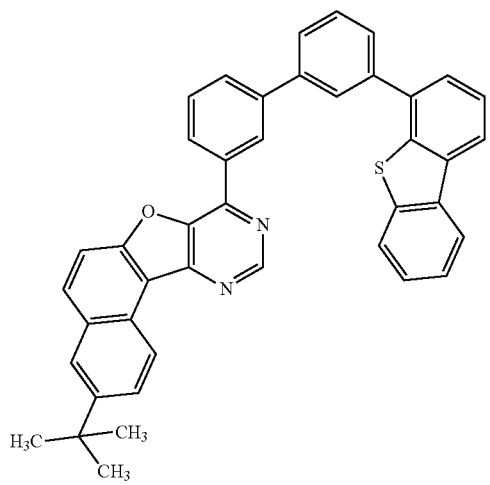
(127)
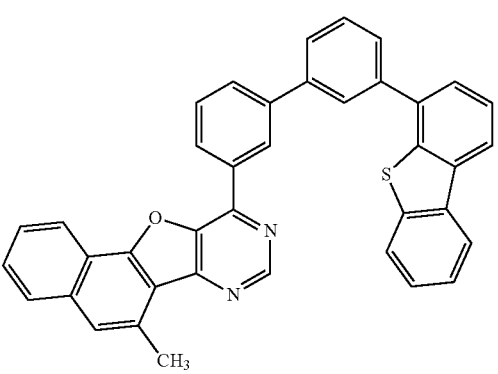
(128)
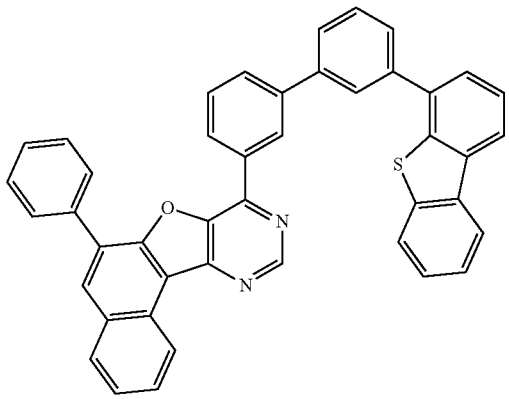
(129)
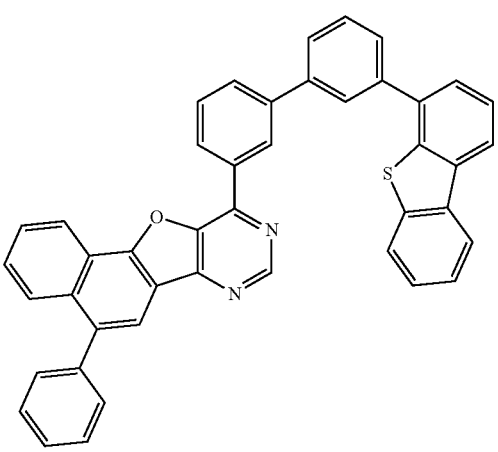
(130)
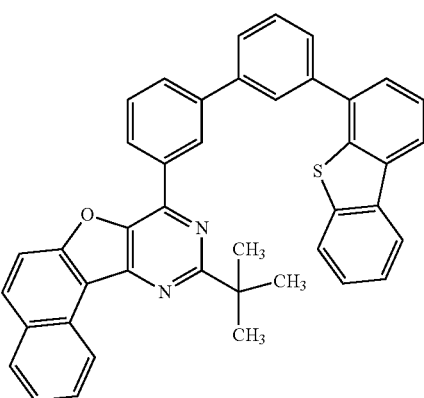
(131)
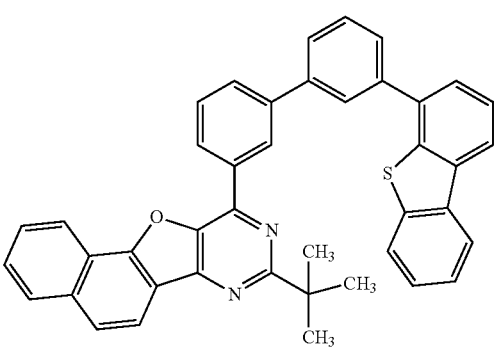

(132)
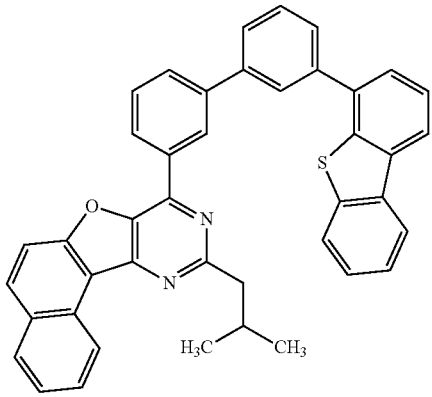
(133)
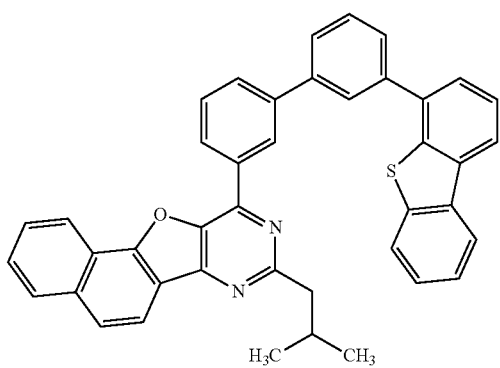
(134)
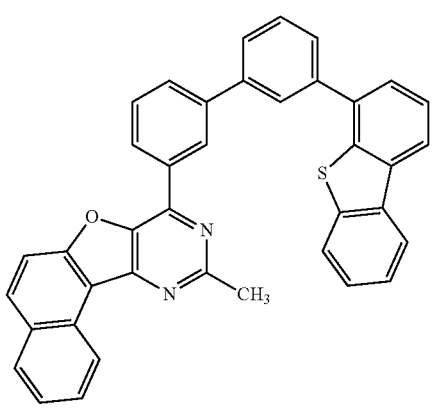
(135)
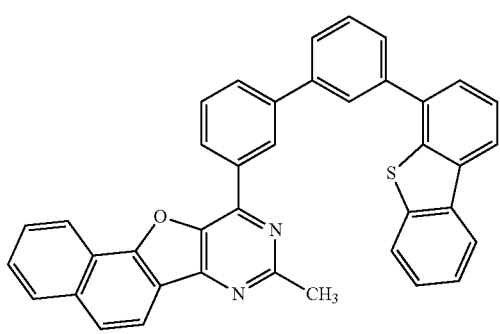
[Chemical Formulae 22]
(136)
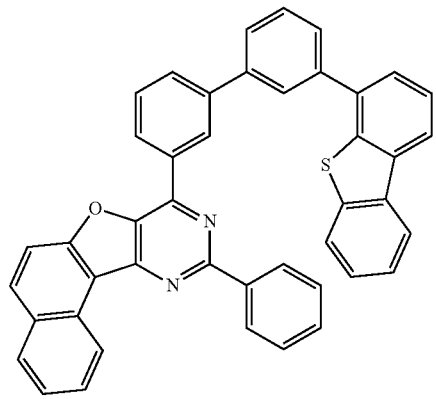
(137)
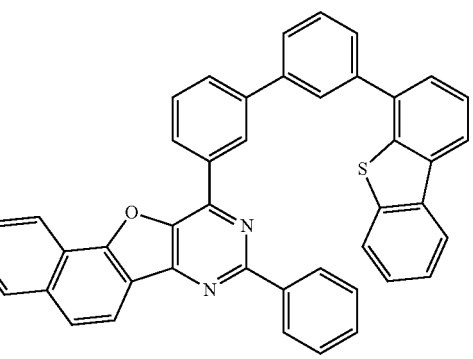
(138)
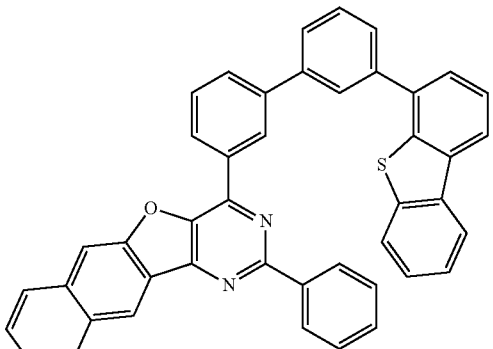
(139)
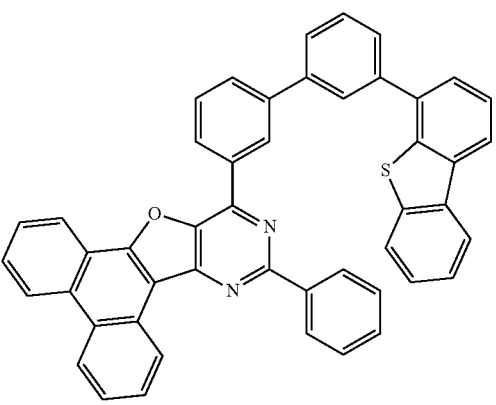

(140)
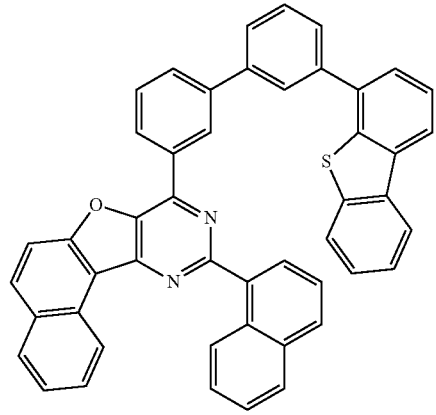
(141)
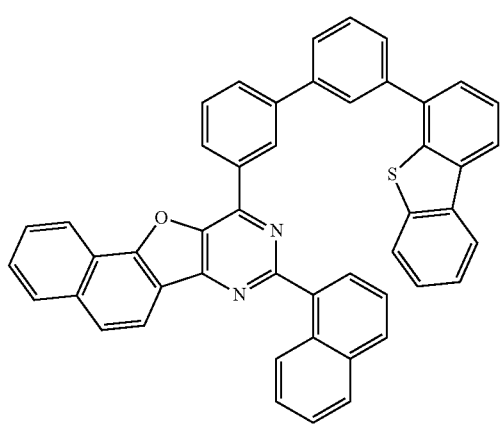
(142)
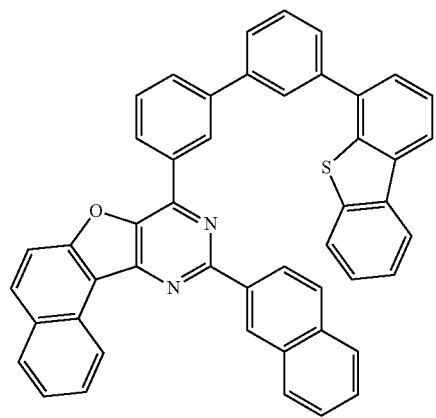
(143)
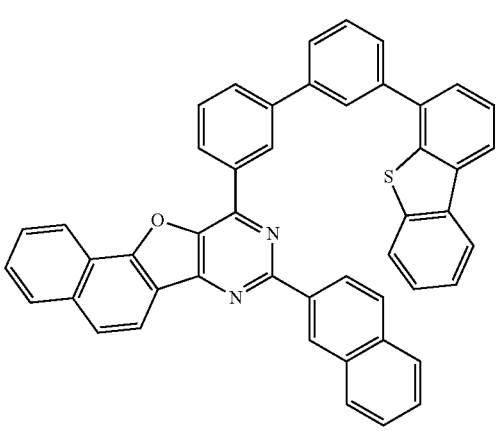
(144)
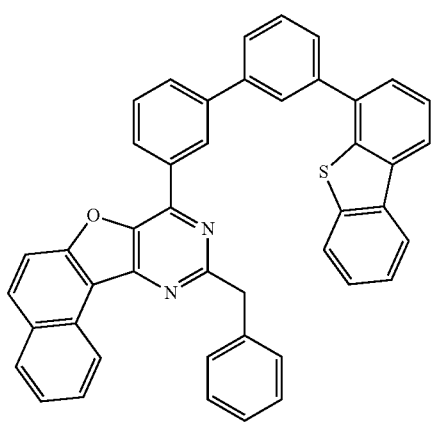
(145)

-continued (146)

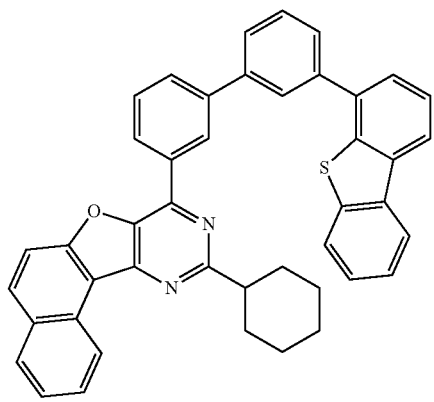

(147)

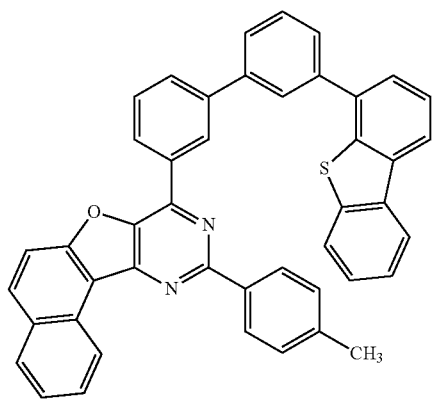

Note that the organic compounds represented by Structural Formulae (100) to (147) are examples of the organic compound represented by General Formula (G1). The organic compound of one embodiment of the present invention is not limited thereto.

Next, examples of methods for synthesizing the organic compounds which are embodiments of the present invention and are represented by General Formulae (G1) and (G3) are described.

<<Method for Synthesizing Organic Compound Represented by General Formula (G1)>>

First, an example of a method for synthesizing the organic compound represented by General Formula (G1) will be described.

[Chemical Formula 23]

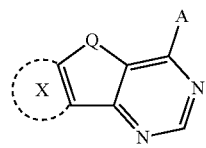

(G1)

In General Formula (G1), A represents an aryl group having 6 to 100 carbon atoms and includes at least one of an aromatic ring and a heteroaromatic ring. Note that the aromatic ring and the heteroaromatic ring may each include a substituent. Furthermore, Q represents oxygen or sulfur. The ring X represents a substituted or unsubstituted naphthalene ring or a substituted or unsubstituted phenanthrene ring.

The organic compound represented by General Formula (G1) can be synthesized by Synthesis Scheme (AX-1) shown below. That is, a halogen compound (A1) reacts with a boronic acid compound (A2), whereby the organic compound represented by General Formula (G1) can be obtained.

[Chemical Formula 24]

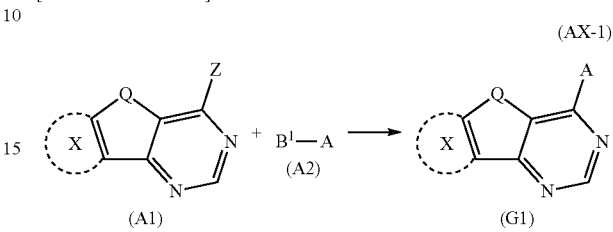

Note that in Synthesis Scheme (AX-1), A represents a group having 6 to 100 carbon atoms and includes at least one of an aromatic ring and a heteroaromatic ring. The aromatic ring and the heteroaromatic ring may each include a substituent. Furthermore, Q represents oxygen or sulfur. The ring X represents a substituted or unsubstituted naphthalene ring or a substituted or unsubstituted phenanthrene ring. Moreover, Z represents a halogen element. In addition, $B^1$ represents a boronic acid, a boronic ester, a cyclic-triolborate salt, or the like. As the cyclic-triolborate salt, a lithium salt, a potassium salt, or a sodium salt may be used.

<<Method for Synthesizing Organic Compound Represented by General Formula (G3)>>

Next, an example of a method for synthesizing the organic compound represented by General Formula (G3) will be described.

[Chemical Formula 25]

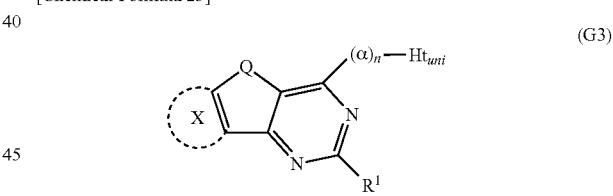

In General Formula (G3), a represents a substituted or unsubstituted phenylene group, and n represents an integer of 1 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. Moreover, Q represents oxygen or sulfur. The ring X represents a substituted or unsubstituted naphthalene ring or a substituted or unsubstituted phenanthrene ring.

The organic compound represented by General Formula (G3) can be synthesized by Synthesis Scheme (AX-2) shown below. That is, a halogen compound (B1) reacts with a substituted or unsubstituted halogen-containing phenyleneboronic acid compound (B2) to obtain an intermediate (B3), and then the intermediate (B3) reacts with a boronic acid compound (B4) including a hole-transport skeleton, whereby the organic compound represented by General Formula (G3) can be obtained.

[Chemical Formula 26]

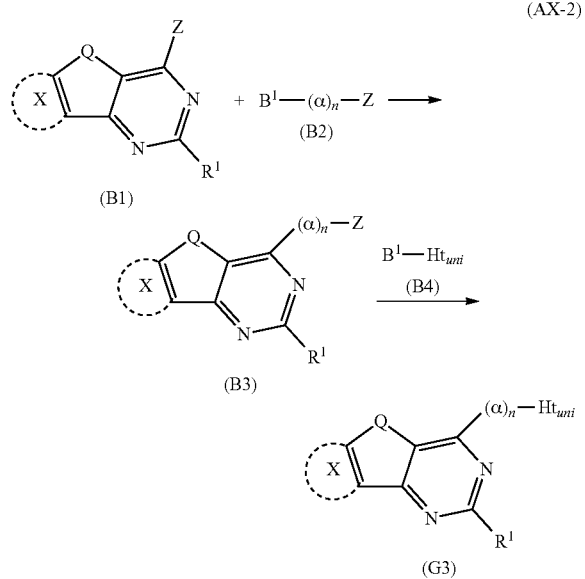

Note that α represents a substituted or unsubstituted phenylene group, and n represents an integer of 1 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms. Moreover, Q represents oxygen or sulfur. The ring X represents a substituted or unsubstituted naphthalene ring or a substituted or unsubstituted phenanthrene ring. Furthermore, Z represents a halogen element. In addition, $B^1$ represents a boronic acid, a boronic ester, a cyclic-triolborate salt, or the like. As the cyclic-triolborate salt, a lithium salt, a potassium salt, or a sodium salt may be used.

The organic compound represented by General Formula (G3) can also be obtained by Synthesis Scheme (AX-2') shown below. That is, one of halogens of a substituted or unsubstituted dihalogen compound (C1) reacts with a substituted or unsubstituted phenyleneboronic acid compound (C2) including a hole-transport skeleton to obtain an intermediate (C3), and then the intermediate (C3) reacts with a boronic acid compound (C4), whereby the organic compound represented by General Formula (G3) can be obtained.

[Chemical Formula 27]

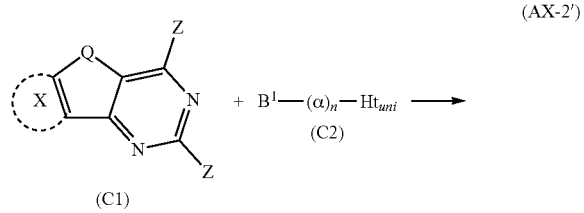

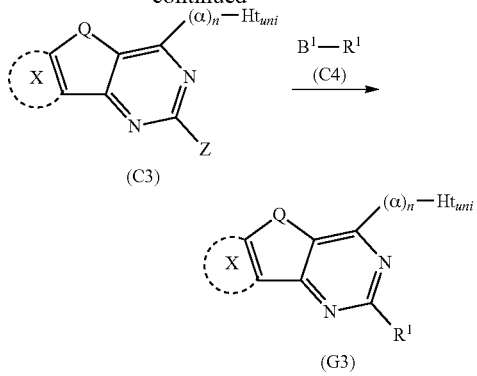

The above is the description of the methods for synthesizing the organic compounds which are embodiments of the present invention and are represented by General Formulae (G1) and (G3); however, the present invention is not limited thereto and another synthesis method may be employed.

Note that the above organic compounds which are embodiments of the present invention each have an electron-transport property and a hole-transport property and thus can be used as a host material in a light-emitting layer or can be used in an electron-transport layer or a hole-transport layer. Furthermore, the above organic compounds are preferably used in combination with a light-emitting substance (guest material), as host materials. In addition, the above organic compounds can be used as light-emitting substances of light-emitting elements. Accordingly, light-emitting elements containing these organic compounds are also included as embodiments of the present invention.

With the use of the organic compound of one embodiment of the present invention, a light-emitting element, a light-emitting device, an electronic device, or a lighting device with high emission efficiency can be obtained. In addition, a light-emitting element, a light-emitting device, an electronic device, or a lighting device with low power consumption can be obtained.

In this embodiment, one embodiment of the present invention has been described. Other embodiments of the present invention are described in the other embodiments. Note that one embodiment of the present invention is not limited thereto. In other words, since various embodiments of the invention are described in this embodiment and the other embodiments, one embodiment of the present invention is not limited to a particular embodiment.

The structures described in this embodiment can be combined with any of the structures described in the other embodiments as appropriate.

Embodiment 2

In this embodiment, a light-emitting element including any of the organic compounds described in Embodiment 1 is described with reference to FIGS. 1A to 1E.

<<Basic Structure of Light-Emitting Element>>

A basic structure of a light-emitting element will be described. FIG. 1A illustrates a light-emitting element including, between a pair of electrodes, an EL layer having a light-emitting layer. Specifically, an EL layer 103 is provided between a first electrode 101 and a second electrode 102.

Figure 1B:
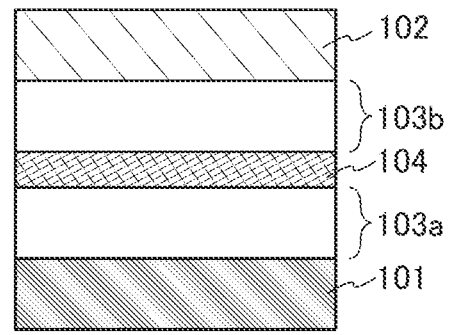

FIG. 1B illustrates a light-emitting element that has a stacked-layer structure (tandem structure) in which a plurality of EL layers (two EL layers 103a and 103b in FIG. 1B) are provided between a pair of electrodes and a charge-generation layer 104 is provided between the EL layers. With the use of such a tandem light-emitting element, a light-emitting device which can be driven at low voltage with low power consumption can be obtained.

The charge-generation layer 104 has a function of injecting electrons into one of the EL layers (103a or 103b) and injecting holes into the other of the EL layers (103b or 103a) when voltage is applied between the first electrode 101 and the second electrode 102. Thus, when voltage is applied in FIG. 1B such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a property of transmitting visible light (specifically, the charge-generation layer 104 has a visible light transmittance of 40% or more). The charge-generation layer 104 functions even when it has lower conductivity than the first electrode 101 or the second electrode 102.

Figure 1C:
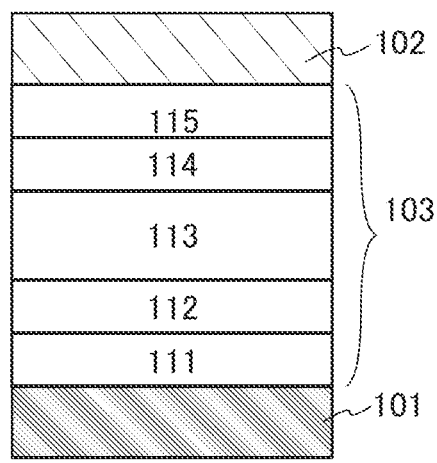

FIG. 1C illustrates a stacked-layer structure of the EL layer 103 in the light-emitting element of one embodiment of the present invention. In this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked in this order over the first electrode 101. Even in the case where a plurality of EL layers are provided as in the tandem structure illustrated in FIG. 1B, the layers in each EL layer are sequentially stacked from the anode side as described above. When the first electrode 101 is a cathode and the second electrode 102 is an anode, the stacking order is reversed.

The light-emitting layer 113 included in the EL layers (103, 103a, and 103b) contains an appropriate combination of a light-emitting substance and a plurality of substances, so that fluorescence or phosphorescence of a desired emission color can be obtained. The light-emitting layer 113 may have a stacked-layer structure having different emission colors. In that case, the light-emitting substance and other substances are different between the stacked light-emitting layers. Alternatively, the plurality of EL layers (103a and 103b) in FIG. 1B may exhibit their respective emission colors. Also in that case, the light-emitting substance and other substances are different between the light-emitting layers.

In the light-emitting element of one embodiment of the present invention, for example, a micro optical resonator (microcavity) structure in which the first electrode 101 is a reflective electrode and the second electrode 102 is a transflective electrode can be employed in FIG. 1C, whereby light emission from the light-emitting layer 113 in the EL layer 103 can be resonated between the electrodes and light emission obtained through the second electrode 102 can be intensified.

Note that when the first electrode 101 of the light-emitting element is a reflective electrode having a structure in which a reflective conductive material and a light-transmitting conductive material (transparent conductive film) are stacked, optical adjustment can be performed by controlling the thickness of the transparent conductive film. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around $(2m'+1)\lambda/4$ (m' is a natural number). Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In that case, the optical path length between the first electrode 101 and the second electrode 102 is, to be exact, the total thickness from a reflective region in the first electrode 101 to a reflective region in the second electrode 102. However, it is difficult to exactly determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer emitting the desired light is, to be exact, the optical path length between the reflective region in the first electrode 101 and the light-emitting region in the light-emitting layer emitting the desired light. However, it is difficult to precisely determine the reflective region in the first electrode 101 and the light-emitting region in the light-emitting layer emitting the desired light; thus, it is assumed that the above effect can be sufficiently obtained wherever the reflective region and the light-emitting region may be set in the first electrode 101 and the light-emitting layer emitting the desired light.

The light-emitting element in FIG. 1C has a microcavity structure, so that light (monochromatic light) with different wavelengths can be extracted even if the same EL layer is used. Thus, separate coloring for obtaining a plurality of emission colors (e.g., R, G, and B) is not necessary. Therefore, high resolution can be easily achieved. Note that a combination with coloring layers (color filters) is also possible. Furthermore, emission intensity of light with a specific wavelength in the front direction can be increased, whereby power consumption can be reduced.

Figure 1D:
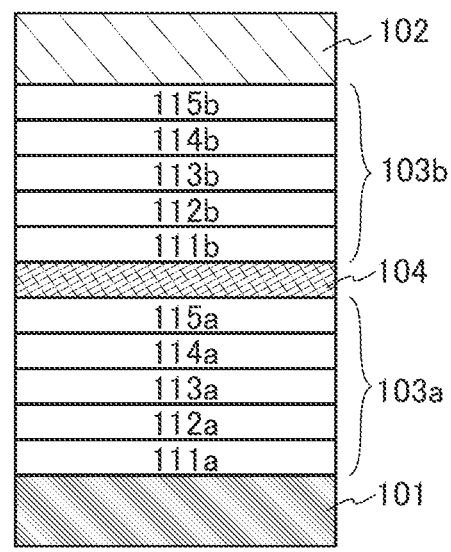
Figure 1E:
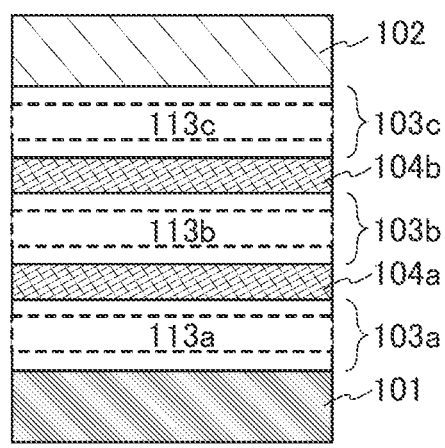

A light-emitting element illustrated in FIG. 1E is an example of the light-emitting element with the tandem structure illustrated in FIG. 1B, and includes three EL layers (103a, 103b, and 103c) stacked with charge-generation layers (104a and 104b) positioned therebetween, as illustrated in the figure. The three EL layers (103a, 103b, and 103c) include respective light-emitting layers (113a, 113b, and 113c) and the emission colors of the light-emitting layers can be selected freely. For example, each of the light-emitting layer 113a and the light-emitting layer 113c can emit blue light, and the light-emitting layer 113b can emit red light, green light, or yellow light. For another example, each of the light-emitting layer 113a and the light-emitting layer 113c can emit red light, and the light-emitting layer 113b can emit blue light, green light, or yellow light.

In the light-emitting element of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance of higher than or equal to 40%. In the case where the light-transmitting electrode is a transflective electrode, the transflective electrode has a visible light reflectance of higher than or equal to 20% and lower than or equal to 80%, and preferably higher than or equal to 40% and lower than or equal to 70%. These electrodes preferably have a resistivity of $1\times10^{-2}$ Ωcm or less.

Furthermore, when one of the first electrode 101 and the second electrode 102 is a reflective electrode in the light-emitting element of one embodiment of the present invention, the visible light reflectance of the reflective electrode is higher than or equal to 40% and lower than or equal to 100%, and preferably higher than or equal to 70% and lower than or equal to 100%. This electrode preferably has a resistivity of $1\times10^{-2}$ Ωcm or less.

<<Specific Structure and Fabrication Method of Light-Emitting Element>>

Specific structures and specific fabrication methods of light-emitting elements of embodiments of the present invention will be described with reference to FIGS. 1A to 1E. Here, a light-emitting element having the tandem structure in FIG. 1B and a microcavity structure will also be described with reference to FIG. 1D. In the light-emitting element in FIG. 1D having a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above. For fabrication of these electrodes, a sputtering method or a vacuum evaporation method can be used.

<First Electrode and Second Electrode>

As materials used for the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be appropriately used. Specifically, an In—Sn oxide (also referred to as ITO), an In—Si—Sn oxide (also referred to as ITSO), an In—Zn oxide, an In—W—Zn oxide, or the like can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting element in FIG. 1D, when the first electrode 101 is an anode, a hole-injection layer 111a and a hole-transport layer 112a of the EL layer 103a are sequentially stacked over the first electrode 101 by a vacuum evaporation method. After the EL layer 103a and the charge-generation layer 104 are formed, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) inject holes from the first electrode 101 that is an anode and the charge-generation layer (104) to the EL layers (103, 103a, and 103b) and each contain a material with a high hole-injection property.

As examples of the material with a high hole-injection property, transition metal oxides such as molybdenum oxide, vanadium oxide, ruthenium oxide, tungsten oxide, and manganese oxide can be given. Alternatively, it is possible to use any of the following materials: phthalocyanine-based compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); and the like.

Alternatively, as the material with a high hole-injection property, a composite material containing a hole-transport material and an acceptor material (an electron-accepting material) can also be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed to have a single-layer structure using a composite material containing a hole-transport material and an acceptor material (electron-accepting material), or a stacked-layer structure in which a layer including a hole-transport material and a layer including an acceptor material (electron-accepting material) are stacked.

The hole-transport layers (112, 112a, and 112b) transport the holes, which are injected from the first electrode 101 and the charge-generation layer (104) by the hole-injection layers (111, 111a, and 111b), to the light-emitting layers (113, 113a, and 113b). Note that the hole-transport layers (112, 112a, and 112b) each contain a hole-transport material. It is particularly preferable that the HOMO level of the hole-transport material included in the hole-transport layers (112, 112a, and 112b) be the same as or close to that of the hole-injection layers (111, 111a, and 111b).

Examples of the acceptor material used for the hole-injection layers (111, 11a, and 111b) include an oxide of a metal belonging to any of Groups 4 to 8 of the periodic table. Specifically, molybdenum oxide, vanadium oxide, niobium oxide, tantalum oxide, chromium oxide, tungsten oxide, manganese oxide, and rhenium oxide can be given. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. Specifically, 7,7,8,8-tetracyano-2,3,5,6-tetrafluoroquinodimethane (abbreviation: F4-TCNQ), chloranil, 2,3,6,7,10,11-hexacyano-1,4,5,8,9,12-hexaazatriphenylene (abbreviation: HAT-CN), and the like can be used. In particular, a compound in which electron-withdrawing groups are bonded to a condensed aromatic ring having a plurality of heteroatoms, like HAT-CN, is thermally stable and preferable. A [3]radialene derivative including an electron-withdrawing group (in particular, a cyano group or a halogen group such as a fluoro group) has a very high electron-accepting property and thus is preferred. Specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile].

The hole-transport materials used for the hole-injection layers (111, 111a, and 111b) and the hole-transport layers (112, 112a, and 112b) are preferably substances with a hole mobility of greater than or equal to $10^{-6}$ cm$^2$/Vs. Note that other substances may be used as long as the substances have a hole-transport property higher than an electron-transport property.

Preferred hole-transport materials are π-electron rich heteroaromatic compounds (e.g., carbazole derivatives and indole derivatives) and aromatic amine compounds, examples of which include compounds having an aromatic amine skeleton, such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 3-[4-(9-phenanthryl)-phenyl]-9-phenyl-9H-carbazole (abbreviation: PCPPn), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 4,4',4''-tris(carbazol-9-yl)triphenylamine (abbreviation: TCTA), 4,4',4''-tris(N,N-diphenylamino)triphenylamine (abbreviation: TDATA), and 4,4',4''-tris[N-(3-methylphenyl)-N-phenylamino]triphenylamine (abbreviation: MTDATA); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA); compounds having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4''-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

A high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), or poly[N,N'-bis(4-butylphenyl)-N,N'-bis(phenyl)benzidine] (abbreviation: Poly-TPD) can also be used.

Note that the hole-transport material is not limited to the above examples and may be one of or a combination of various known materials when used for the hole-injection layers (111, 111a, and 111b) and the hole-transport layers (112, 112a, and 112b). Note that the hole-transport layers (112, 112a, and 112b) may each be formed of a plurality of layers. That is, for example, the hole-transport layers may each have a stacked-layer structure of a first hole-transport layer and a second hole-transport layer.

In the light-emitting element in FIG. 1D, the light-emitting layer 113a is formed over the hole-transport layer 112a of the EL layer 103a by a vacuum evaporation method. After the EL layer 103a and the charge-generation layer 104 are formed, the light-emitting layer 113b is formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance whose emission color is blue, violet, bluish violet, green, yellowish green, yellow, orange, red, or the like is appropriately used. When the plurality of light-emitting layers (113a, 113b, and 113c) are formed using different light-emitting substances, different emission colors can be exhibited (for example, complementary emission colors are combined to achieve white light emission). Furthermore, a stacked-layer structure in which one light-emitting layer contains two or more kinds of light-emitting substances may be employed.

Note that the light-emitting layers (113, 113a, 113b, and 113c) may each contain one or more kinds of organic compounds (a host material and an assist material) in addition to a light-emitting substance (guest material). As the one or more kinds of organic compounds, the organic compounds described in Embodiment 1 or one or both of the hole-transport material and the electron-transport material described in this embodiment can be used.

As the light-emitting substance that can be used for the light-emitting layers (113, 113a, 113b, and 113c), a light-emitting substance that converts triplet excitation energy into light emission in the visible light range or a light-emitting substance that converts singlet excitation energy into light emission in the visible light range can be used. In the case where the light-emitting substance is used in combination with the organic compounds described in Embodiment 1, the light-emitting substance that converts triplet excitation energy into light emission in the visible light range is preferably used.

Examples of other light-emitting substances are given below.

As examples of a light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit the respective emission colors (emission peaks) and thus, any of them is appropriately selected according to need.

As examples of a phosphorescent material which emits blue or green light and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-N2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4', 6'-difluorophenyl)pyridinato-N,C$^2$']iridium(III) tetrakis(1-pyrazolyl)borate (abbreviation: FIr6), bis[2-(4', 6'-difluorophenyl)pyridinato-N,C$^2$]iridium(III) picolinate (abbreviation: FIrpic), bis{2-[3',5'-bis(trifluoromethyl)phenyl]pyridinato-N,C$^2$'}iridium(III) picolinate (abbreviation: [Ir(CF$_3$ppy)$_2$(pic)]), and bis[2-(4', 6'-difluorophenyl)pyridinato-N,C$^2$]iridium(III) acetylacetonate (abbreviation: FIr(acac)); and the like can be given.

As examples of a phosphorescent material which emits green or yellow light and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN3]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^2$')iridium(III) (abbreviation: [Ir(ppy)$_3$]), bis(2-phenylpyridinato-N,C$^2$')iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^2$')iridium(III) (abbreviation: [Ir(pq)$_3$]), and bis(2-phenylquinolinato-N,C$^2$')iridium(III) acetylacetonate (abbreviation: [Ir(pq)$_2$(acac)]); organometallic complexes such as bis(2,4-diphenyl-1,3-oxazolato-N,C$^2$')iridium(III) acetylacetonate (abbreviation: [Ir(dpo)$_2$(acac)]), bis{2-[4'-(perfluorophenyl)phenyl]pyridinato-N,C$^2$'}iridium(III) acetylacetonate (abbreviation: [Ir(p-PF-ph)$_2$(acac)]), and bis(2-phenylbenzothiazolato-N,C$^2$')iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As examples of a phosphorescent material which emits yellow or red light and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^2$']iridium(III) (abbreviation: [Ir(mpq)$_2$(acac)]), (acetylacetonato)bis(2,3-diphenylquinoxalinato-N,C$^2$')iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,C$^2$')iridium(III) (abbreviation: [Ir(piq)$_3$]) and bis(1-phenylisoquinolinato-N,C$^2$')iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As an example of the light-emitting substance that converts singlet excitation energy into light emission, a substance that emits fluorescence (fluorescent material) can be given. Examples of the substance that emits fluorescence include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'- bis[3-(9-phenyl-9H-fluoren-9-yl)phenyl]pyrene-1,6-diamine (abbreviation: 1,6mMemFLPAPm), N,N'-diphenyl-N,N'-bis[4-(9-phenyl-9H-fluoren-9-yl)phenyl]pyrene-1,6-diamine (abbreviation: 1,6FLPAPm), N,N'-bis(dibenzofuran-2-yl)-N,N'-diphenylpyrene-1,6-diamine (abbreviation: 1,6FrAPm), N,N'-bis(dibenzothiophen-2-yl)-N,N'-diphenylpyrene-1,6-diamine (abbreviation: 1,6ThAPm), N,N'-(pyrene-1,6-diyl)bis[(N-phenylbenzo[b]naphtho[1,2-d]furan)-6-amine] (abbreviation: 1,6BnfAPm), N,N'-(pyrene-1,6-diyl)bis[(N-phenylbenzo[b]naphtho[1,2-d]furan)-8-amine] (abbreviation: 1,6BnfAPm-02), and N,N'-(pyrene-1,6-diyl)bis[(6,N-diphenylbenzo[b]naphtho[1,2-d]furan)-8-amine](abbreviation: 1,6BnfAPm-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

As the organic compounds used in the light-emitting layers (113, 113a, 113b, and 113c), one or more kinds of substances having a larger energy gap than the light-emitting substance (the guest material) are used. Thus, the following organic compounds (the host material and the assist material) as well as the organic compounds described in Embodiment 1 can be used as appropriate.

When the light-emitting substance is a fluorescent material, for example, it is preferable to use, as the host material, an organic compound that has a high energy level in a singlet excited state and has a low energy level in a triplet excited state. For example, an anthracene derivative or a tetracene derivative is preferably used. Specific examples include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the host material. In that case, it is possible to use a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, an aromatic amine, a carbazole derivative, and the like.

Note that more specifically, any of the following hole-transport materials and electron-transport materials can be used as the host material, for example.

Examples of the host material having a high hole-transport property include aromatic amine compounds such as N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Other examples include carbazole derivatives such as 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Other examples of the carbazole derivative include 4,4'-di(N-carbazolyl)biphenyl (abbreviation: CBP), 1,3,5-tris[4-(N-carbazolyl)phenyl]benzene (abbreviation: TCPB), and 1,4-bis[4-(N-carbazolyl)phenyl]-2,3,5,6-tetraphenylbenzene.

Examples of the host material having a high hole-transport property include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N,N'-triphenyl-N,N',N"-tris(9-phenylcarbazol-3-yl)benzene-1,3,5-triamine (abbreviation: PCA3B), N-(4-biphenyl)-N-(9,9-dimethyl-9H-fluoren-2-yl)-9H-carbazol-3-amine (abbreviation: PCBiF), N-(1,1'-biphenyl-4-yl)-N-[4-(9-phenyl-9H-carbazol-3-yl)phenyl]-9,9- dimethyl-9H-fluoren-2-amine (abbreviation: PCBBiF), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 2-[N-(9-phenylcarbazol-3-yl)-N-phenylamino]spiro-9,9'-bifluorene (abbreviation: PCASF), 2,7-bis[N-(4-diphenylaminophenyl)-N-phenylamino]-spiro-9,9'-bifluorene (abbreviation: DPA2SF), N-[4-(9H-carbazol-9-yl)phenyl]-N-(4-phenyl)phenylaniline (abbreviation: YGA1BP), and N,N'-bis[4-(carbazol-9-yl)phenyl]-N,N'-diphenyl-9,9-dimethylfluorene-2,7-diamine (abbreviation: YGA2F). Other examples are carbazole compounds, thiophene compounds, furan compounds, fluorene compounds; triphenylene compounds; phenanthrene compounds, and the like such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 3,3'-bis(9-phenyl-9H-carbazole) (abbreviation: PCCP), 1,3-bis(N-carbazolyl)benzene (abbreviation: mCP), 3,6-bis(3,5-diphenylphenyl)-9-phenylcarbazole (abbreviation: CzTP), 4-{3-[3-(9-phenyl-9H-fluoren-9-yl)phenyl]phenyl}dibenzofuran (abbreviation: mmDBFFLBi-II), 4,4', 4"-(benzene-1,3,5-triyl)tri(dibenzofuran) (abbreviation: DBF3P-II), 1,3,5-tri(dibenzothiophen-4-yl)-benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II).

Examples of the host material having a high electron-transport property include a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), or bis(8-quinolinolato)zinc(II) (abbreviation.: Znq). Alternatively, a metal complex having an oxazole-based or thiazole-based ligand, such as bis[2-(2-benzoxazolyl)phenolato]zinc(II) (abbreviation: ZnPBO) or bis[2-(2-benzothiazolyl)phenolato]zinc(II) (abbreviation: ZnBTZ) can be used. Other than such metal complexes, any of the following can be used: oxadiazole derivatives such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-4-phenyl-5-(4-tert-butylphenyl)-1,2,4-triazole (abbreviation: TAZ); a compound having an imidazole skeleton (in particular, a benzimidazole derivative) such as 2,2', 2"-(1,3,5-benzenetriyl)tris(1-phenyl-1H-benzimidazole)(abbreviation: TPBI) or 2-[3-(dibenzothiophen-4-yl)phenyl]-1-phenyl-1H-benzimidazole (abbreviation: mDBTBIm-II); a compound having an oxazole skeleton (in particular, a benzoxazole derivative) such as 4,4'-bis(5-methylbenzoxazol-2-yl)stilbene (abbreviation: BzOs); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl] dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); heterocyclic compounds having a triazine skeleton, such as 2-{4-[3-(N-phenyl-9H-carbazol-3-yl)-9H-carbazol-9-yl]phenyl}-4,6-diphenyl-1,3,5-triazine (abbreviation: PCCzPTzn); and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used.

In addition, as the host material, condensed polycyclic aromatic compounds such as anthracene derivatives, phenanthrene derivatives, pyrene derivatives, chrysene derivatives, and dibenzo[gp]chrysene derivatives can be used. Specifically, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N",N",N''',N'''-octaphenyldibenzo[gp]chrysene-2,7,10,15-tetraamine (abbreviation: DBC1), 9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), or the like can be used.

In the case where a plurality of organic compounds are used for the light-emitting layers (113, 113a, 113b, and 113c), two compounds that form an exciplex (a first compound and a second compound) mixed with an organometallic complex may be used. In that case, although any of various organic compounds can be used in an appropriate combination, in order to form an exciplex efficiently, it is particularly preferable to combine a compound that easily accepts holes (hole-transport material) and a compound that easily accepts electrons (electron-transport material). As the hole-transport material and the electron-transport material, specifically, any of the materials described in this embodiment can be used. With this structure, high efficiency, low voltage, and a long lifetime can be achieved at the same time.

The TADF material is a material that can up-convert a triplet excited state into a singlet excited state (i.e., reverse intersystem crossing is possible) using a little thermal energy and efficiently exhibits light emission (fluorescence)

from the singlet excited state. The TADF is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Note that "delayed fluorescence" exhibited by the TADF material refers to light emission having the same spectrum as normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin, such as a porphyrin containing magnesium(Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(1OH-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can be combined with another organic compound.

In the light-emitting element in FIG. 1D, an electron-transport layer 114a is formed over the light-emitting layer 113a of the EL layer 103a by a vacuum evaporation method. After the EL layer 103a and the charge-generation layer 104 are formed, an electron-transport layer 114b is formed over the light-emitting layer 113b of the EL layer 103b by a vacuum evaporation method.

<Electron-Transport Layer>

The electron-transport layers (114, 114a, and 114b) transport the electrons, which are injected from the second electrode 102 and the charge-generation layer (104) by the electron-injection layers (115, 115a, and 115b), to the light-emitting layers (113, 113a, and 113b). Note that the electron-transport layers (114, 114a, and 114b) each contain an electron-transport material. It is preferable that the electron-transport materials included in the electron-transport layers (114, 114a, and 114b) be substances with an electron mobility of higher than or equal to $1 \times 10^{-6}$ cm²/Vs. Note that other substances may also be used as long as the substances have an electron-transport property higher than a hole-transport property.

Examples of the electron-transport material include metal complexes having a quinoline ligand, a benzoquinoline ligand, an oxazole ligand, and a thiazole ligand; an oxadiazole derivative; a triazole derivative; a phenanthroline derivative; a pyridine derivative; and a bipyridine derivative. In addition, a π-electron deficient heteroaromatic compound such as a nitrogen-containing heteroaromatic compound can also be used.

Specifically, it is possible to use metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, bis[2-(2-hydroxyphenyl)benzoxazolato]zinc(II) (abbreviation: $Zn(BOX)_2$), and bis[2-(2-hydroxyphenyl)benzothiazolato]zinc(II) (abbreviation: $Zn(BTZ)_2$), heteroaromatic compounds such as 2-(4-biphenylyl)-5-(4-tert-butylphenyl)-1,3,4-oxadiazole (abbreviation: PBD), OXD-7, 3-(4'-tert-butylphenyl)-4-phenyl-5-(4"-biphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), and 4,4'-bis(5-methylbenzoxazol-2-yl)stilbene (abbreviation: BzOs), and quinoxaline derivatives and dibenzoquinoxaline derivatives such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Alternatively, a high molecular compound such as poly (2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

Each of the electron-transport layers (114, 114a, and 114b) is not limited to a single layer, but may be a stack of two or more layers each containing any of the above substances.

In the light-emitting element in FIG. 1D, the electron-injection layer 115a is formed over the electron-transport layer 114a of the EL layer 103a by a vacuum evaporation method. After the EL layer 103a and the charge-generation layer 104 are formed, the components up to the electron-transport layer 114b of the EL layer 103b are formed. Then, the electron-injection layer 115b is formed over the electron-transport layer 114b by a vacuum evaporation method.

<Electron-Injection Layer>

The electron-injection layers (115, 115a, and 115b) each contain a substance having a high electron-injection property. The electron-injection layers (115, 115a, and 115b) can each be formed using an alkali metal, an alkaline earth metal, or a compound thereof, such as lithium fluoride (LiF), cesium fluoride (CsF), calcium fluoride ($CaF_2$), or lithium oxide ($LiO_x$). A rare earth metal compound like erbium fluoride ($ErF_3$) can also be used. Electride may also be used for the electron-injection layers (115, 115a, and 115b). Examples of the electride include a substance in which electrons are added at high concentration to calcium oxide-aluminum oxide. Any of the substances for forming the electron-transport layers (114, 114*a*, and 114*b*), which are given above, can also be used.

A composite material in which an organic compound and an electron donor (donor) are mixed may also be used for the electron-injection layers (115, 115*a*, and 115*b*). Such a composite material is excellent in an electron-injection property and an electron-transport property because electrons are generated in the organic compound by the electron donor. The organic compound here is preferably a material excellent in transporting the generated electrons; specifically, for example, the electron-transport materials for forming the electron-transport layers (114, 114*a*, and 114*b*) (e.g., a metal complex and a heteroaromatic compound) can be used. As the electron donor, a substance showing an electron-donating property with respect to the organic compound may be used. Preferable examples are an alkali metal, an alkaline earth metal, and a rare earth metal. Specifically, lithium, cesium, magnesium, calcium, erbium, ytterbium, and the like can be given. Furthermore, an alkali metal oxide and an alkaline earth metal oxide are preferable, and a lithium oxide, a calcium oxide, a barium oxide, and the like can be given. Alternatively, a Lewis base such as magnesium oxide can be used. Further alternatively, an organic compound such as tetrathiafulvalene (abbreviation: TTF) can be used.

In the case where light obtained from the light-emitting layer 113*b* is amplified, for example, the optical path length between the second electrode 102 and the light-emitting layer 113*b* is preferably less than one fourth of the wavelength $\lambda$ of light emitted from the light-emitting layer 113*b*. In that case, the optical path length can be adjusted by changing the thickness of the electron-transport layer 114*b* or the electron-injection layer 115*b*.

<Charge-Generation Layer>

The charge-generation layer 104 has a function of injecting electrons into the EL layer 103*a* and injecting holes into the EL layer 103*b* when voltage is applied between the first electrode (anode) 101 and the second electrode (cathode) 102. The charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 by using any of the above materials can suppress an increase in drive voltage caused by the stack of the EL layers.

In the case where the charge-generation layer 104 has a structure in which an electron acceptor is added to a hole-transport material, any of the materials described in this embodiment can be used as the hole-transport material. As the electron acceptor, it is possible to use 7,7,8,8-tetracyano-2,3,5,6-tetrafluoroquinodimethane (abbreviation: $F_4$-TCNQ), chloranil, and the like. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, or the like is used.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103*c* in FIG. 1E has a structure similar to those of the above-described EL layers (103, 103*a*, and 103*b*). In addition, the charge-generation layers 104*a* and 104*b* each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES); a synthetic resin such as acrylic; polypropylene; polyester; polyvinyl fluoride; polyvinyl chloride; polyamide; polyimide; aramid; epoxy; an inorganic vapor deposition film; and paper.

For fabrication of the light-emitting element in this embodiment, a vacuum process such as an evaporation method or a solution process such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layers (111, 11*a*, and 111*b*), the hole-transport layers (112, 112*a*, and 112*b*), the light-emitting layers (113, 113*a*, 113*b*, and 113*c*), the electron-transport layers (114, 114*a*, and 114*b*), the electron-injection layers (115, 115*a*, and 115*b*)) included in the EL layers and the charge-generation layers (104, 104*a*, and 104*b*) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Note that materials that can be used for the functional layers (the hole-injection layers (111, 111*a*, and 111*b*), the hole-transport layers (112, 112*a*, and 112*b*), the light-emitting layers (113, 113*a*, 113*b*, and 113*c*), the electron-transport layers (114, 114*a*, and 114*b*), and the electron-injection layers (115, 115*a*, and 115*b*)) that are included in the EL layers (103, 103*a*, and 103*b*) and the charge-generation layers (104, 104*a*, and 104*b*) in the light-emitting element described in this embodiment are not limited to the above materials, and other materials can be used in combination as long as the functions of the layers are fulfilled. For example, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot material may be a colloidal quantum dot material, an alloyed quantum dot material, a core-shell quantum dot material, a core quantum dot material, or the like.

The structure described in this embodiment can be combined with any of the structures described in the other embodiments as appropriate.

Embodiment 3

Figure 2A:
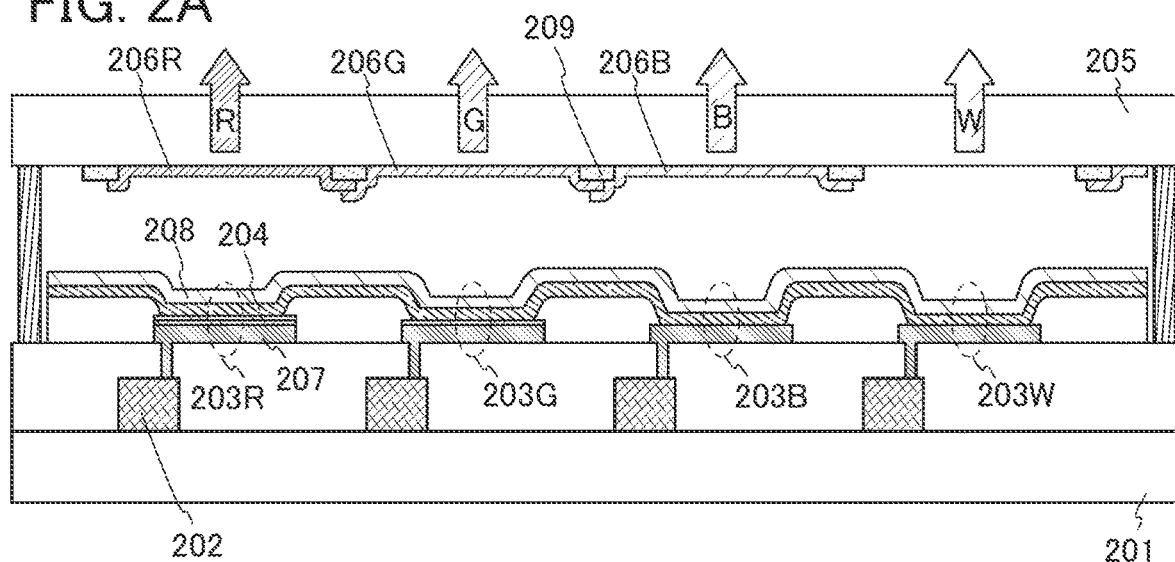
FIGS. 2A to 2C illustrate light-emitting devices.

In this embodiment, a light-emitting device of one embodiment of the present invention is described. Note that a light-emitting device illustrated in FIG. 2A is an active-matrix light-emitting device in which transistors (FETs) 202 are electrically connected to light-emitting elements (203R, 203G, 203B, and 203W) over a first substrate 201. The light-emitting elements (203R, 203G, 203B, and 203W) include a common EL layer 204 and each have a microcavity structure in which the optical path length between electrodes is adjusted depending on the emission color of the light-emitting element. The light-emitting device is a top-emission light-emitting device in which light is emitted from the EL layer 204 through color filters (206R, 206G, and 206B) formed on a second substrate 205.

The light-emitting device illustrated in FIG. 2A is fabricated such that a first electrode 207 functions as a reflective electrode and a second electrode 208 functions as a transflective electrode. Note that description in any of the other embodiments can be referred to as appropriate for electrode materials for the first electrode 207 and the second electrode 208.

Figure 2B:
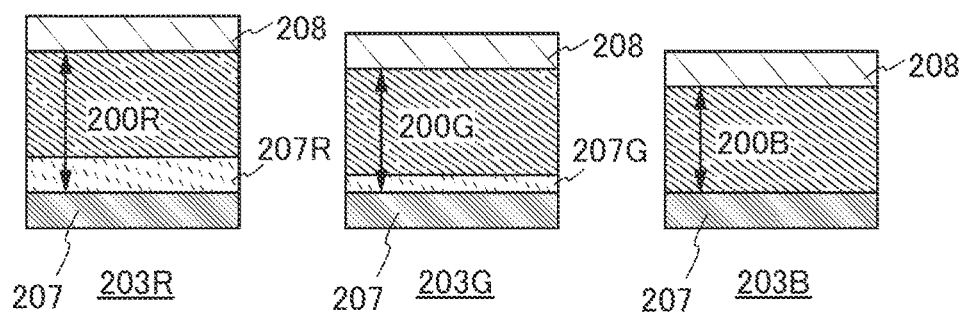

In the case where the light-emitting element 203R functions as a red light-emitting element, the light-emitting element 203G functions as a green light-emitting element, the light-emitting element 203B functions as a blue light-emitting element, and the light-emitting element 203W functions as a white light-emitting element in FIG. 2A, for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2B. Note that optical adjustment can be performed in such a manner that a conductive layer 207R is stacked over the first electrode 207 in the light-emitting element 203R and a conductive layer 207G is stacked over the first electrode 207 in the light-emitting element 203G as illustrated in FIG. 2B.

The second substrate 205 is provided with the color filters (206R, 206G, and 206B). Note that the color filters each transmit visible light in a specific wavelength range and blocks visible light in a specific wavelength range. Thus, as illustrated in FIG. 2A, the color filter 206R that transmits only light in the red wavelength range is provided in a position overlapping with the light-emitting element 203R, whereby red light emission can be obtained from the light-emitting element 203R. Furthermore, the color filter 206G that transmits only light in the green wavelength range is provided in a position overlapping with the light-emitting element 203G, whereby green light emission can be obtained from the light-emitting element 203G. Moreover, the color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of each color filter. The color filters (206R, 206G, and 206B) and the black layer 209 may be covered with an overcoat layer formed using a transparent material.

Figure 2C:
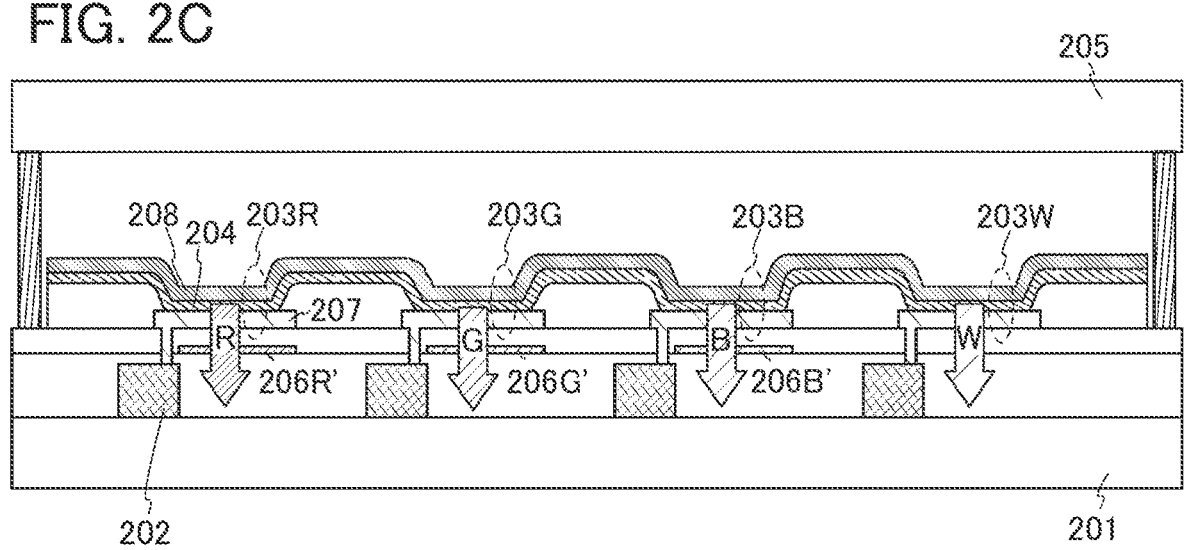

Although the light-emitting device in FIG. 2A has a structure in which light is extracted from the second substrate 205 side (top emission structure), a structure in which light is extracted from the first substrate 201 side where the FETs 202 are formed (bottom emission structure) may be employed as illustrated in FIG. 2C. In the case of a bottom-emission light-emitting device, the first electrode 207 is formed as a transflective electrode and the second electrode 208 is formed as a reflective electrode. As the first substrate 201, a substrate having at least a light-transmitting property is used. As illustrated in FIG. 2C, color filters (206R', 206G', and 206B') are provided so as to be closer to the first substrate 201 than the light-emitting elements (203R, 203G, and 203B) are.

In FIG. 2A, the light-emitting elements are the red light-emitting element, the green light-emitting element, the blue light-emitting element, and the white light-emitting element; however, the light-emitting elements of one embodiment of the present invention are not limited to the above, and a yellow light-emitting element or an orange light-emitting element may be used. Note that description in any of the other embodiments can be referred to as appropriate for materials that are used for the EL layers (a light-emitting layer, a hole-injection layer, a hole-transport layer, an electron-transport layer, an electron-injection layer, a charge-generation layer, and the like) to fabricate each of the light-emitting elements. In that case, a color filter needs to be appropriately selected depending on the emission color of the light-emitting element.

With the above structure, a light-emitting device including light-emitting elements that exhibit a plurality of emission colors can be fabricated.

Note that the structures described in this embodiment can be combined with any of the structures described in the other embodiments as appropriate.

Embodiment 4

In this embodiment, a light-emitting device of one embodiment of the present invention is described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is one embodiment of the present invention. Note that any of the light-emitting elements described in other embodiments can be used in the light-emitting device described in this embodiment.

In this embodiment, an active-matrix light-emitting device will be described with reference to FIGS. 3A and 3B.

Figure 3A:
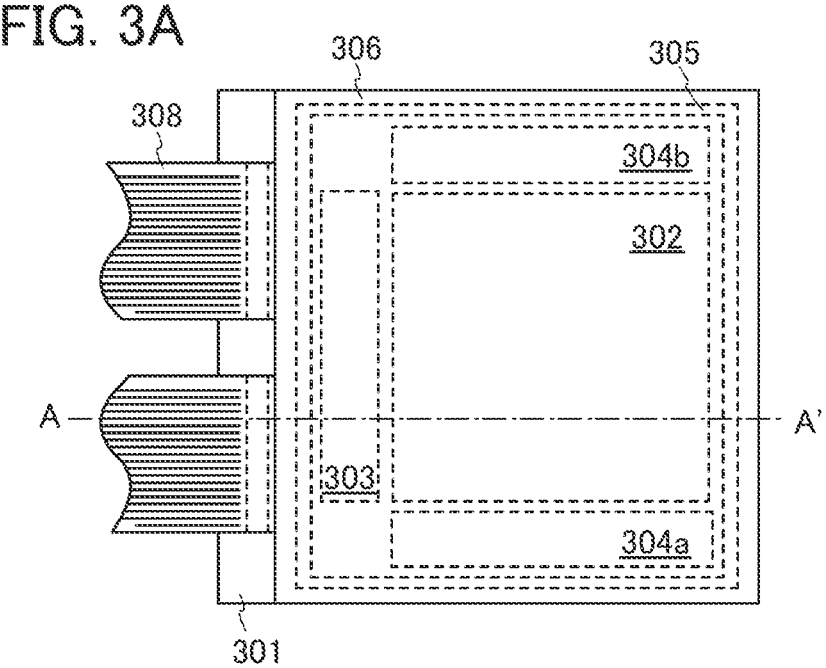
FIGS. 3A and 3B illustrate a light-emitting device.
Figure 3B:
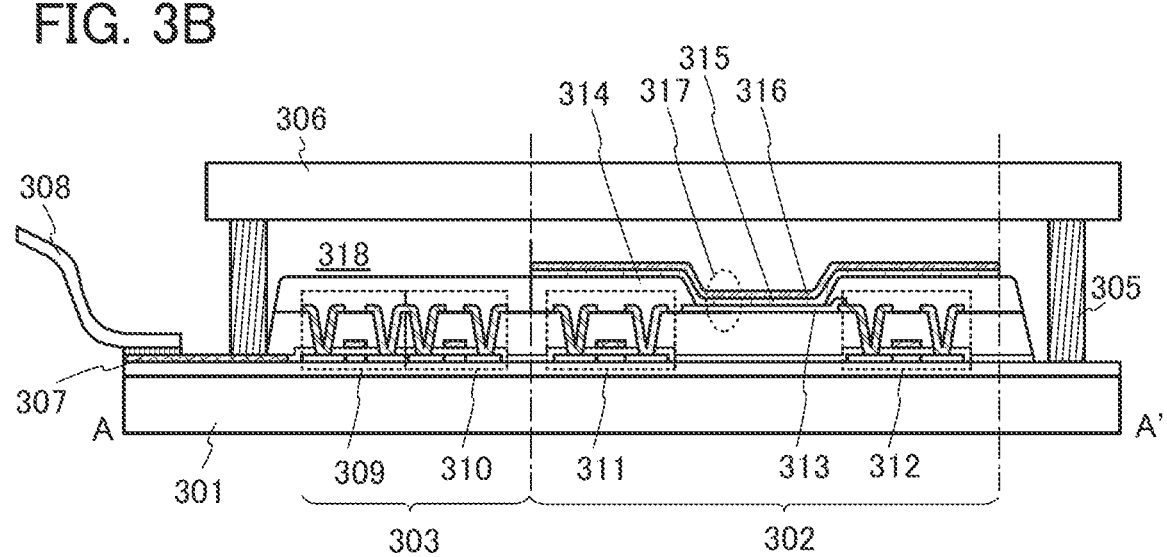

FIG. 3A is a top view illustrating the light-emitting device, and FIG. 3B is a cross-sectional view taken along chain line A-A' in FIG. 3A. The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is connected to an FPC 308 that is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

FIG. 3B illustrates a cross-sectional structure of the light-emitting device.

The pixel portion 302 includes a plurality of pixels each of which includes an FET (switching FET) 311, an FET (current control FET) 312, and a first electrode 313 electrically connected to the FET 312. Note that the number of FETs included in each pixel is not particularly limited and can be set appropriately.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

For the semiconductor, a Group 14 element, a compound semiconductor, an oxide semiconductor, an organic semiconductor, or the like can be used, for example. As a typical example, a semiconductor containing silicon, a semiconductor containing gallium arsenide, or an oxide semiconductor containing indium can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a driver circuit may be provided outside.

An end portion of the first electrode 313 is covered with an insulator 314. The insulator 314 can be formed using an organic compound such as a negative photosensitive resin or a positive photosensitive resin (acrylic resin), or an inorganic compound such as silicon oxide, silicon oxynitride, or silicon nitride. The insulator 314 preferably has a curved surface with curvature at an upper end portion or a lower end portion thereof. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the components of a light-emitting element 317 described in this embodiment.

Although not illustrated, the second electrode 316 is electrically connected to the FPC 308 that is an external input terminal.

Although the cross-sectional view in FIG. 3B illustrates only one light-emitting element 317, a plurality of light-emitting elements are arranged in a matrix in the pixel portion 302. Light-emitting elements that emit light of three kinds of colors (R, G, and B) are selectively formed in the pixel portion 302, whereby a light-emitting device capable of displaying a full-color image can be obtained. In addition to the light-emitting elements that emit light of three kinds of colors (R, G, and B), for example, light-emitting elements that emit light of white (W), yellow (Y), magenta (M), cyan (C), and the like may be formed. For example, the light-emitting elements that emit light of some of the above colors are used in combination with the light-emitting elements that emit light of three kinds of colors (R, G, and B), whereby effects such as an improvement in color purity and a reduction in power consumption can be achieved. Alternatively, a light-emitting device which is capable of displaying a full-color image may be fabricated by a combination with color filters. As color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin, glass frit, or the like can be used for the sealant 305. It is preferable to use a material that is permeable to as little moisture and oxygen as possible for the sealant 305. As the second substrate 306, a substrate that can be used as the first substrate 301 can be similarly used. Thus, any of the various substrates described in the other embodiments can be appropriately used. As the substrate, a glass substrate, a quartz substrate, or a plastic substrate made of fiber-reinforced plastic (FRP), polyvinyl fluoride (PVF), polyester, acrylic, or the like can be used. In the case where glass frit is used for the sealant, the first substrate 301 and the second substrate 306 are preferably glass substrates in terms of adhesion.

Accordingly, the active-matrix light-emitting device can be obtained.

In the case where the active-matrix light-emitting device is provided over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester), or the like), a leather substrate, and a rubber substrate. With the use of any of these substrates, an increase in durability, an increase in heat resistance, a reduction in weight, and a reduction in thickness can be achieved.

Note that the structures described in this embodiment can be combined with any of the structures described in the other embodiments as appropriate.

Embodiment 5

In this embodiment, examples of a variety of electronic devices and an automobile manufactured using the light-emitting device of one embodiment of the present invention or a display device including the light-emitting element of one embodiment of the present invention are described.

Electronic devices illustrated in FIGS. 4A to 4E can include a housing 7000, a display portion 7001, a speaker 7003, an LED lamp 7004, operation keys 7005 (including a power switch or an operation switch), a connection terminal 7006, a sensor 7007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

Figure 4A:
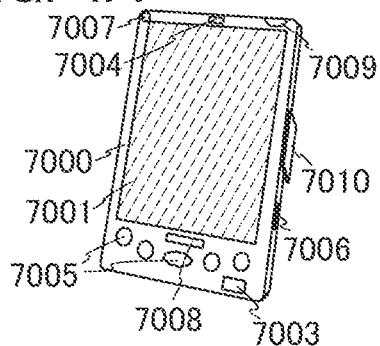
FIGS. 4A to 4G illustrate electronic devices.

FIG. 4A illustrates a mobile computer that can include a switch 7009, an infrared port 7010, and the like in addition to the above components.

Figure 4B:
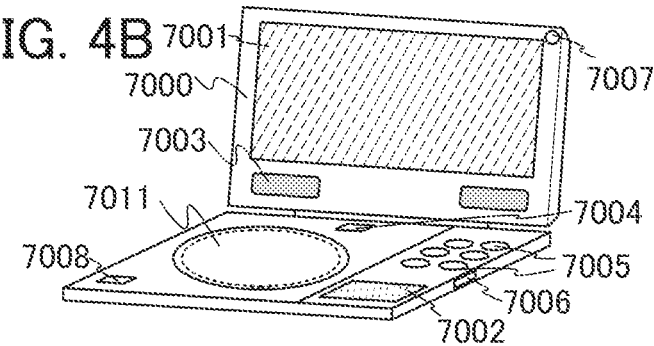

FIG. 4B illustrates a portable image reproducing device (e.g., a DVD player) that is provided with a recording medium and can include a second display portion 7002, a recording medium reading portion 7011, and the like in addition to the above components.

Figure 4C:
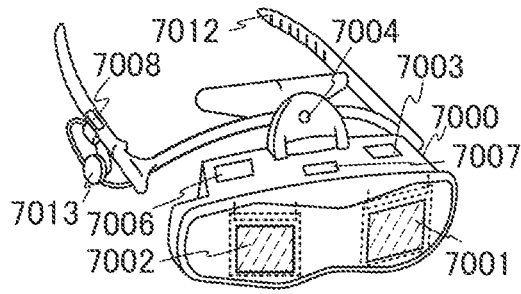

FIG. 4C illustrates a goggle-type display that can include the second display portion 7002, a support 7012, an earphone 7013, and the like in addition to the above components.

Figure 4D:
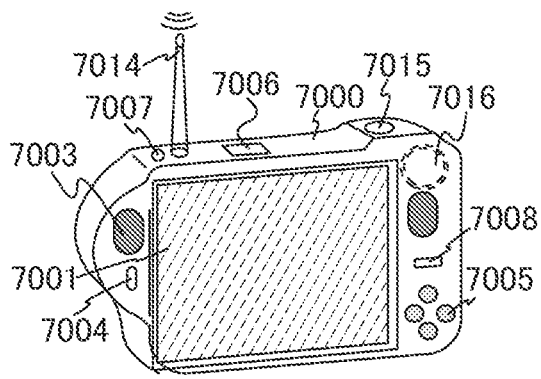

FIG. 4D illustrates a digital camera that has a television reception function and can include an antenna 7014, a shutter button 7015, an image receiving portion 7016, and the like in addition to the above components.

Figure 4E:
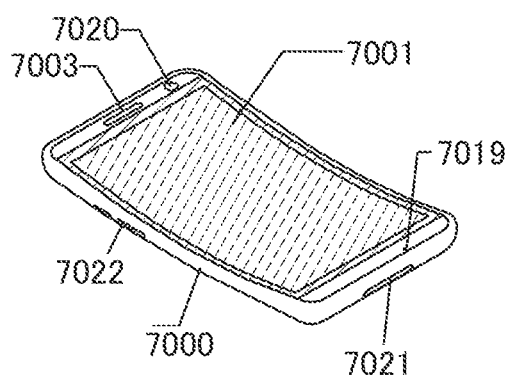

FIG. 4E illustrates a cellular phone (including a smartphone) that can include the display portion 7001, a microphone 7019, the speaker 7003, a camera 7020, an external connection portion 7021, an operation button 7022, and the like in the housing 7000.

Figure 4F:
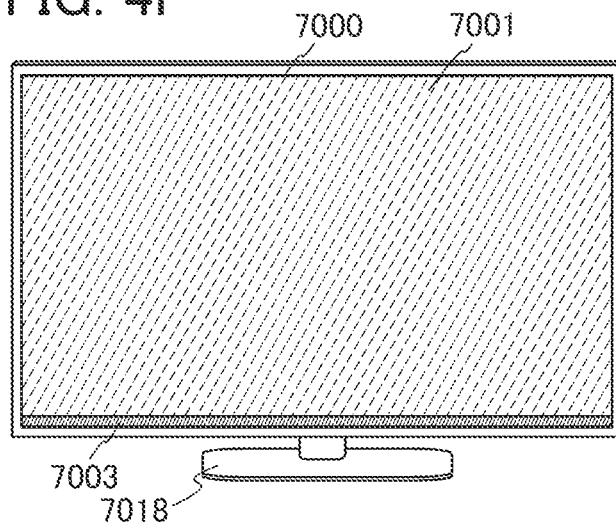

FIG. 4F illustrates a large-size television set (also referred to as TV or a television receiver) that can include the housing 7000, the display portion 7001, the speaker 7003, and the like. In addition, here, the housing 7000 is supported by a stand 7018.

The electronic devices illustrated in FIGS. 4A to 4F can have a variety of functions, such as a function of displaying a variety of data (a still image, a moving image, a text image, and the like) on the display portion, a touch panel function, a function of displaying a calendar, date, time, and the like, a function of controlling a process with a variety of types of software (programs), a wireless communication function, a function of connecting to a variety of computer networks with a wireless communication function, a function of transmitting and receiving a variety of data with a wireless communication function, a function of reading a program or data stored in a recording medium and displaying the program or data on the display portion, and the like. Furthermore, an electronic device including a plurality of display portions can have a function of displaying image data mainly on one display portion while displaying text data on another display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that can be provided for the electronic devices illustrated in FIGS. 4A to 4F are not limited to those described above, and the electronic devices can have a variety of functions.

Figure 4G:
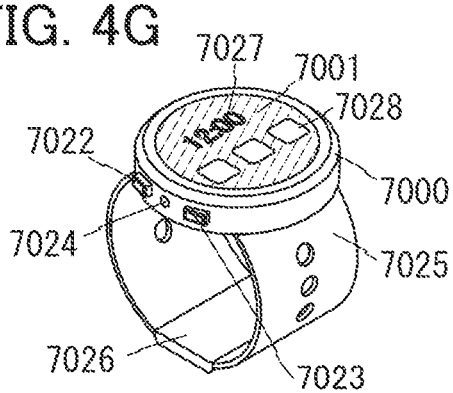

FIG. 4G illustrates a smart watch, which includes the housing 7000, the display portion 7001, operation buttons 7022 and 7023, a connection terminal 7024, a band 7025, a clasp 7026, and the like.

The display portion 7001 mounted in the housing 7000 serving as a bezel includes a non-rectangular display region. The display portion 7001 can display an icon 7027 indicating time, another icon 7028, and the like. The display portion 7001 may be a touch panel (an input/output device) including a touch sensor (an input device).

The smart watch illustrated in FIG. 4G can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

The housing 7000 can include a speaker, a sensor (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like.

Note that the light-emitting device of one embodiment of the present invention or the display device including the light-emitting element of one embodiment of the present invention can be used in the display portion of each electronic device described in this embodiment, enabling display with high color purity.

Figure 5A:
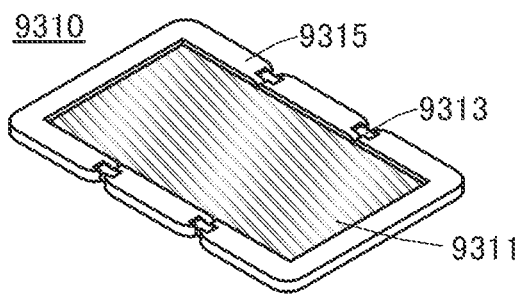
FIGS. 5A to 5C illustrate an electronic device.
Figure 5B:
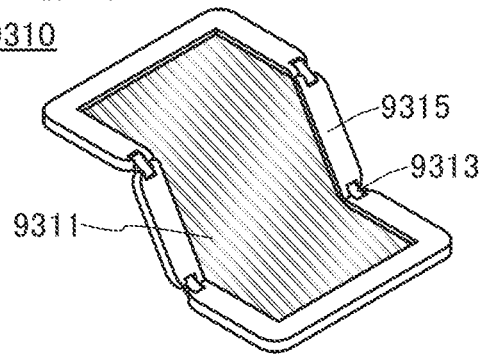
Figure 5C:
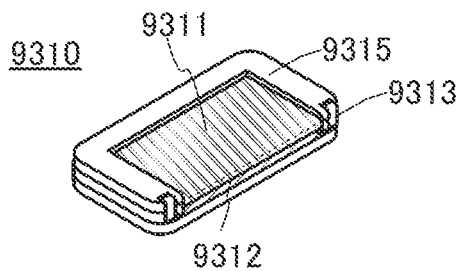

Another electronic device including the light-emitting device is a foldable portable information terminal illustrated in FIGS. 5A to 5C. FIG. 5A illustrates a portable information terminal 9310 which is opened. FIG. 5B illustrates the portable information terminal 9310 which is being opened or being folded. FIG. 5C illustrates the portable information terminal 9310 which is folded. The portable information terminal 9310 is highly portable when folded. The portable information terminal 9310 is highly browsable when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a connection portion between two housings 9315 with the use of the hinges 9313, the portable information terminal 9310 can be reversibly changed in shape from an opened state to a folded state. The light-emitting device of one embodiment of the present invention can be used for the display portion 9311. In addition, display with high color purity can be performed. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of application and the like can be smoothly performed.

Figure 6A:
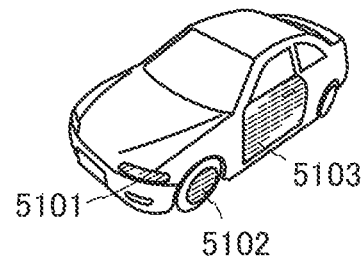
FIGS. 6A and 6B illustrate an automobile.
Figure 6B:
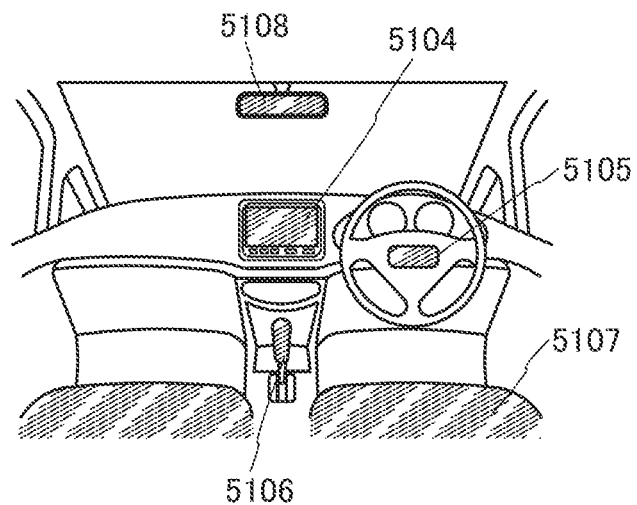

FIGS. 6A and 6B illustrate an automobile including the light-emitting device. The light-emitting device can be incorporated in the automobile, and specifically, can be included in lights 5101 (including lights of the rear part of the car), a wheel cover 5102, a part or whole of a door 5103, or the like on the outer side of the automobile which is illustrated in FIG. 6A. The light-emitting device can also be included in a display portion 5104, a steering wheel 5105, a gear lever 5106, a seat 5107, an inner rearview mirror 5108, or the like on the inner side of the automobile which is illustrated in FIG. 6B, or in a part of a glass window.

As described above, the electronic devices and automobiles can be obtained using the light-emitting device or the display device of one embodiment of the present invention. In that case, display with high color purity can be performed. Note that the light-emitting device or the display device can be used for electronic devices and automobiles in a variety of fields without being limited to those described in this embodiment.

Note that the structures described in this embodiment can be combined with any of the structures described in the other embodiments as appropriate.

Embodiment 6

In this embodiment, a structure of a lighting device fabricated using the light-emitting device of one embodiment of the present invention or the light-emitting element which is a part of the light-emitting device is described with reference to FIGS. 7A to 7D.

Figure 7A:
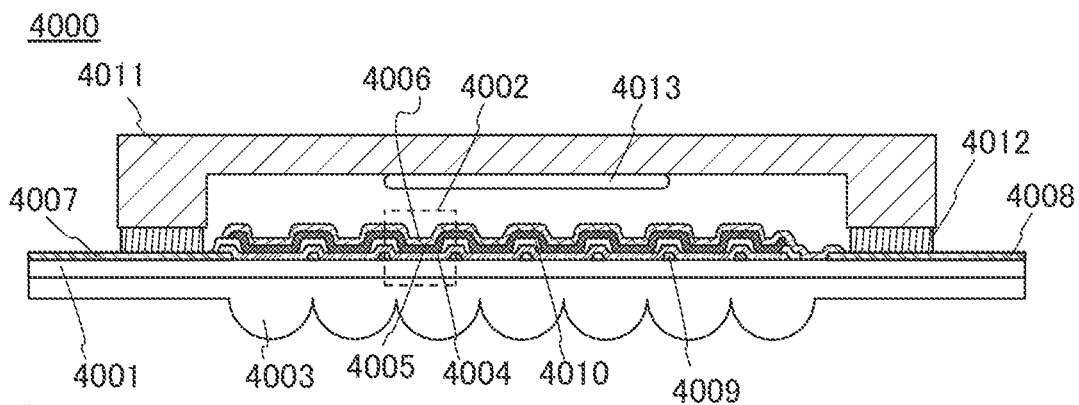
FIGS. 7A to 7D illustrate lighting devices.
Figure 7B:
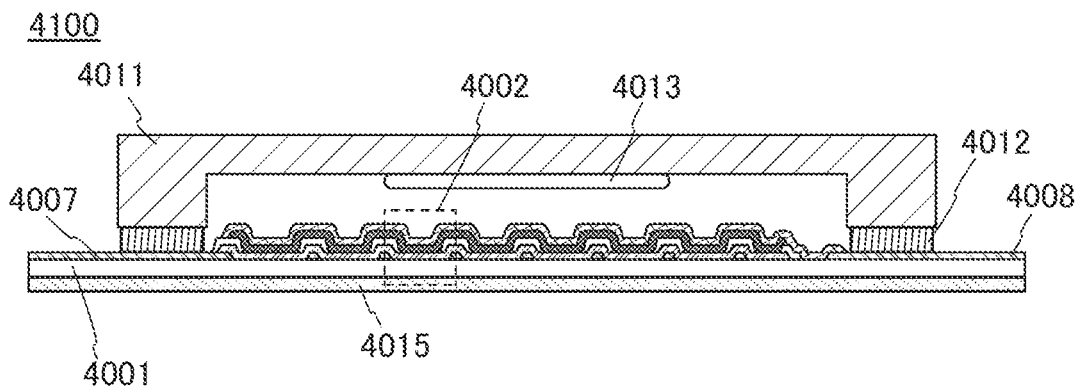
Figure 7C:
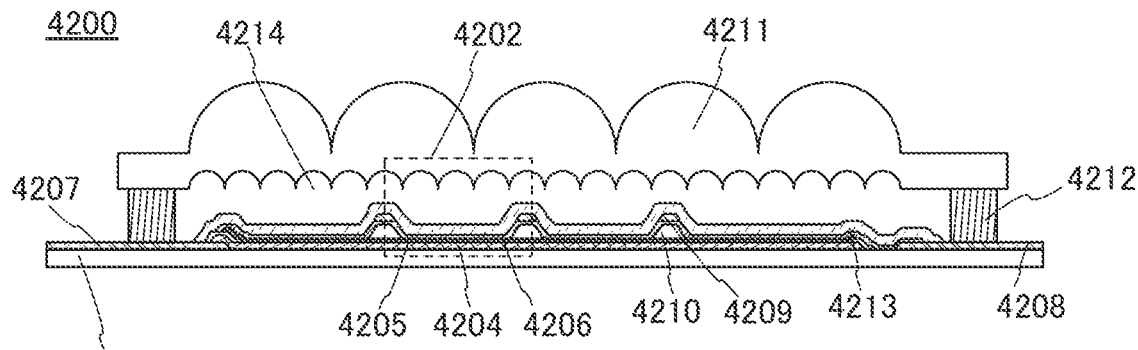
Figure 7D:
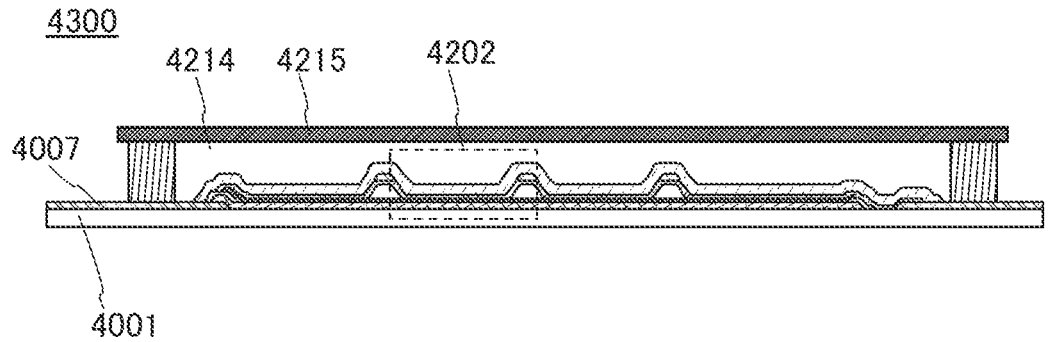

FIGS. 7A to 7D are examples of cross-sectional views of lighting devices. FIGS. 7A and 7B illustrate bottom-emission lighting devices in which light is extracted from the substrate side, and FIGS. 7C and 7D illustrate top-emission lighting devices in which light is extracted from the sealing substrate side.

A lighting device 4000 illustrated in FIG. 7A includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7A, whereby the extraction efficiency of light emitted from the light-emitting element 4002 can be increased.

Instead of the substrate 4003, a diffusion plate 4015 may be provided on the outside of the substrate 4001 as in a lighting device 4100 illustrated in FIG. 7B.

A lighting device 4200 illustrated in FIG. 7C includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may be provided. An insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7C, whereby the extraction efficiency of light emitted from the light-emitting element 4202 can be increased.

Instead of the sealing substrate 4211, a diffusion plate 4215 may be provided over the light-emitting element 4202 as in a lighting device 4300 illustrated in FIG. 7D.

Note that with the use of the light-emitting device of one embodiment of the present invention or the light-emitting element which is a part of the light-emitting device as described in this embodiment, a lighting device having desired chromaticity can be provided.

Note that the structures described in this embodiment can be combined with any of the structures described in the other embodiments as appropriate.

Embodiment 7

Figure 8:
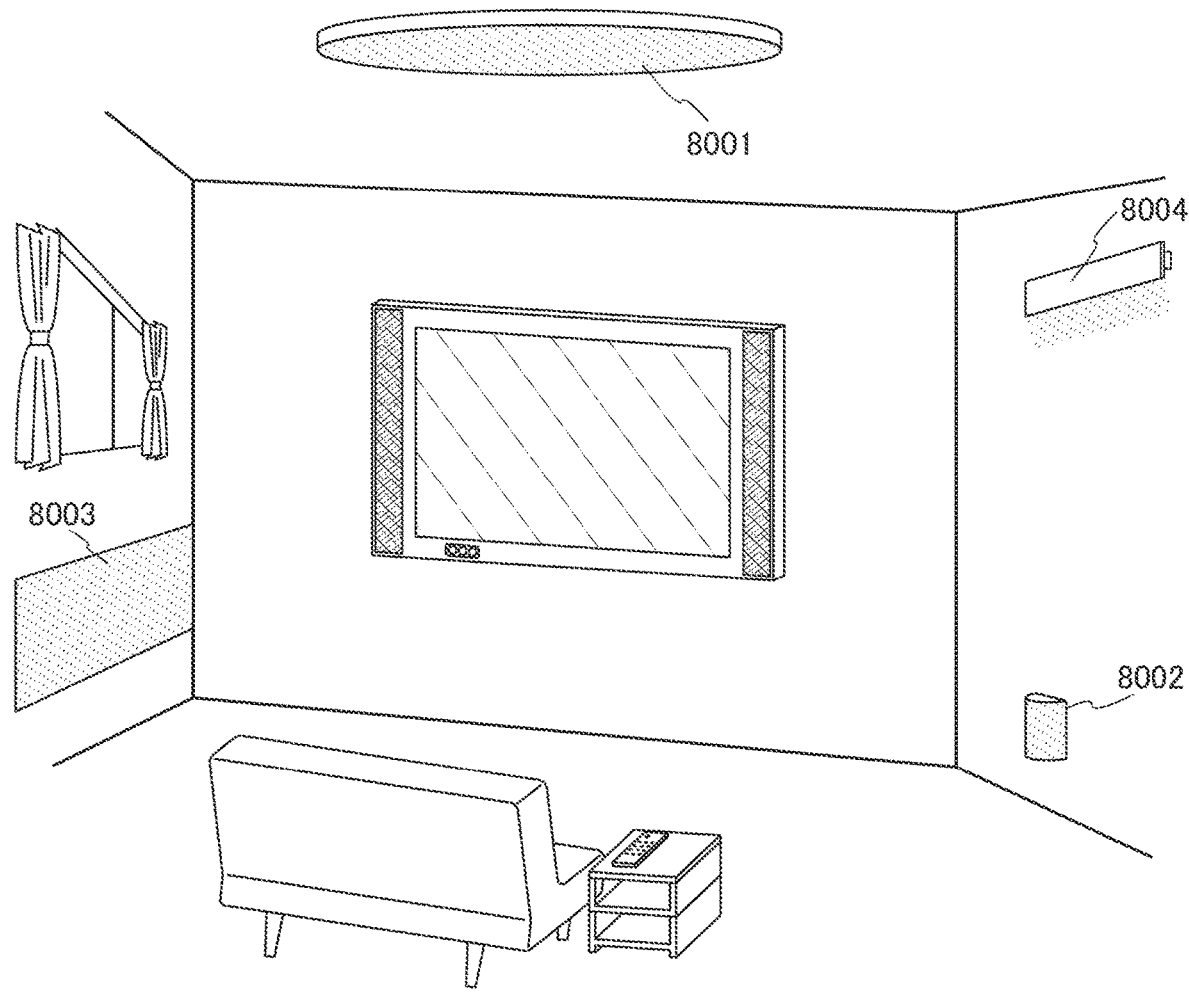
FIG. 8 illustrates lighting devices.

In this embodiment, application examples of lighting devices fabricated using the light-emitting device of one embodiment of the present invention or the light-emitting element which is a part of the light-emitting device will be described with reference to FIG. 8.

A ceiling light 8001 can be used as an indoor lighting device. Examples of the ceiling light 8001 include a direct-mount light and an embedded light. Such a lighting device is fabricated using the light-emitting device and a housing or a cover in combination. Besides, application to a cord pendant light (light that is suspended from a ceiling by a cord) is also possible.

A foot light 8002 lights a floor so that safety on the floor can be improved. For example, it can be effectively used in a bedroom, on a staircase, or on a passage. In that case, the size or shape of the foot light can be changed depending on the area or structure of a room. The foot light 8002 can be a stationary lighting device fabricated using the light-emitting device and a support base in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be increased. The sheet-like lighting can also be used on a wall or housing having a curved surface.

In addition, a lighting device 8004 in which the direction of light from a light source is controlled to be only a desired direction can be used.

Besides the above examples, when the light-emitting device of one embodiment of the present invention or the light-emitting element which is a part of the light-emitting device is used as part of furniture in a room, a lighting device that functions as the furniture can be obtained.

As described above, a variety of lighting devices that include the light-emitting device can be obtained. Note that these lighting devices are also embodiments of the present invention.

The structures described in this embodiment can be combined with any of the structures described in the other embodiments as appropriate.

Example 1

Synthesis Example 1

This example describes a method for synthesizing 8-[3'-(dibenzothiophen-4-yl)(1,1'-biphenyl-3-yl)]naphtho[1',2': 4,5]furo[3,2-d]pyrimidine (abbreviation: 8mDBtBPNfpm), which is the organic compound of one embodiment of the present invention and represented by Structural Formula (100) in Embodiment 1. The structure of 8mDBtBPNfpm is shown below.

[Chemical Formula 28]

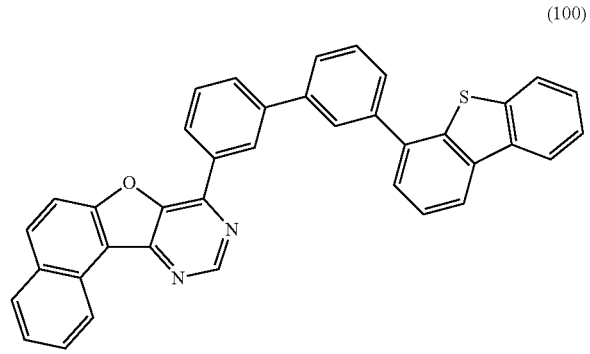

(100)

(8mDBtBPNfpm)

Step 1: Synthesis of ethyl 1-amino-naphtho[2,1-b]furan-2-carboxylate

First, 4.0 g of 2-hydroxynaphthalene-1-carbonitrile and 6.6 g of potassium carbonate were put into a flask, the atmosphere in the flask was replaced with nitrogen, 30 mL of DMF and 4.0 g of ethyl bromoacetate were added, and the mixture was heated at 80° C. for 16 hours. The obtained reaction mixture was added to 100 mL of iced water for rapid cooling, the mixture was stirred for an hour, and then filtered. The obtained residue was washed with water, and recrystallized with ethanol and water, whereby 4.4 g of a target substance (a brown solid) was obtained in a yield of 72%. A synthesis scheme of Step 1 is shown in (a-1) below.

[Chemical Formula 29]

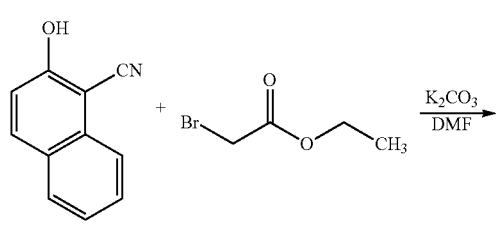

(a-1)

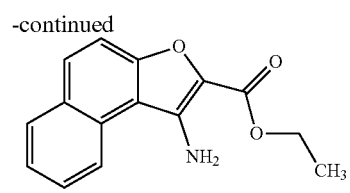

Step 2: Synthesis of naphtho[1', 2': 4,5]furo[3,2-d]pyrimidin-8(9H)-one

Next, 4.4 g of ethyl 1-amino-naphtho[2,1-b]furan-2-carboxylate synthesized in Step 1, 1.8 g of formamidine acetate, and 25 mL of formamide were put into a flask, and the mixture was heated at 160° C. for 8 hours. To the obtained reaction mixture was added 100 mL of water and the mixture was filtered. The residue was washed with water to give 3.9 g of a target substance (a brown solid) in a yield of 96%. A synthesis scheme of Step 2 is shown in (a-2) below.

[Chemical Formula 30]

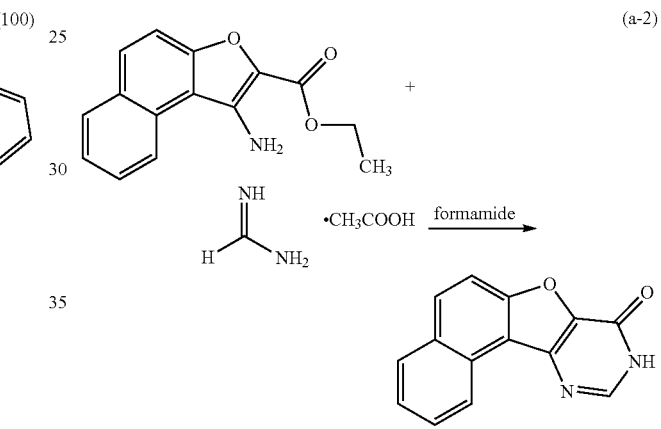

(a-2)

Step 3: Synthesis of 8-chloro-naphtho[1', 2': 4,5]furo[3,2-d]pyrimidine

Next, 3.9 g of naphtho[1', 2': 4,5]furo[3,2-d]pyrimidin-8(9H)-one synthesized in Step 2 and 15 mL of phosphoryl chloride were put into a flask, and the mixture was heated under a nitrogen stream at 100° C. for 6 hours. The obtained reaction mixture was added to 100 mL of iced water for rapid cooling, 330 mL of a 3M sodium hydroxide aqueous solution was added, and the mixture was stirred for an hour. This mixture was filtered and the residue was washed with ethanol to give 1.8 g of a target substance (a yellow solid) in a yield of 42%. A synthesis scheme of Step 3 is shown in (a-3) below.

[Chemical Formula 31]

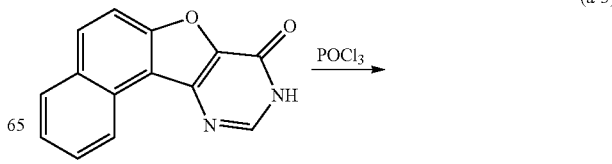

(a-3)

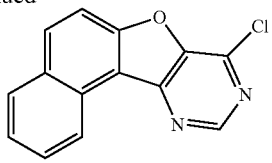

Step 4: Synthesis of 8-[3'-(dibenzothiophen-4-yl)(1,1'-biphenyl-3-yl)]naphtho[1', 2': 4,5]furo[3,2-d]pyrimidine (abbreviation: 8mDBtBPNfpm)

Next, 1.8 g of 8-chloro-naphtho[1', 2': 4,5]furo[3,2-d]pyrimidine synthesized in Step 3, 2.9 g of 3-(dibenzothiophen-4-yl)phenylboronic acid, 15 mL of a 2M potassium carbonate aqueous solution, 150 mL of toluene, and 15 mL of ethanol were put into a flask, and the atmosphere in the flask was replaced with nitrogen. To this mixture was added 0.29 g of tetrakis(triphenylphosphine)palladium(0), and the mixture was heated under a nitrogen stream at 95° C. for 12 hours. The obtained reaction mixture was filtered and the obtained residue was washed with water and then with ethanol.

Then, the obtained residue was dissolved in toluene, the mixture was purified through a filter aid in which Celite, alumina, and Celite were stacked in this order, and then recrystallized with toluene, whereby 3.6 g of a target pale yellow solid was obtained in a yield of 95%. A synthesis scheme of Step 4 is shown in (a-4) below.

[Chemical Formula 32]

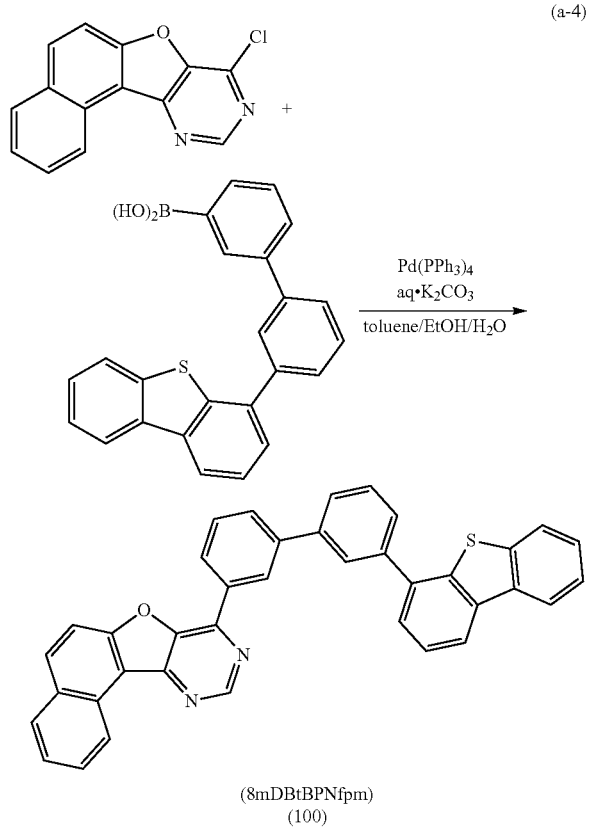

(8mDBtBPNfpm)
(100)

By a train sublimation method, 3.6 g of the obtained pale yellow solid was purified. In the purification by sublimation, the pale yellow solid was heated at 310° C. under a pressure of 2.7 Pa with an argon flow rate of 5 mL/min. After the purification by sublimation, 2.7 g of a pale yellow solid was obtained at a collection rate of 73%.

Figure 9:
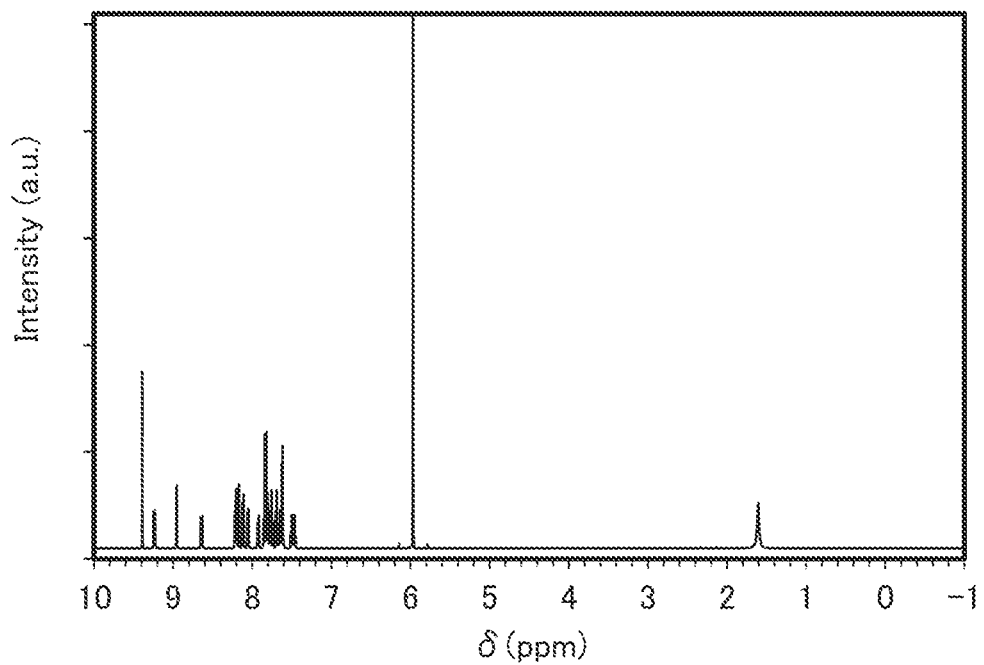
FIG. 9 is a $^1$H-NMR chart of an organic compound represented by Structural Formula (100)

Analysis results by nuclear magnetic resonance ($^1$H-NMR) spectroscopy of the obtained pale yellow solid are shown below. FIG. 9 is a $^1$H-NMR chart. The $^1$H-NMR chart revealed that 8mDBtBPNfpm, the organic compound represented by Structural Formula (100), was obtained in this example.

$^1$H-NMR δ (TCE-d$_2$): 7.45-7.52 ((m, 2H), 7.60-7.71 (m, 4H), 7.74-7.86 (m, 6H), 7.92 (d, 1H), 8.05 (d, 1H), 8.12 (d, 1H), 8.16 (s, 1H), 8.19-8.22 (m, 2H), 8.64 (d, 1H), 8.96 (s, 1H), 9.23 (d, 1H), 9.32 (s, 1H).

Figure 10A:
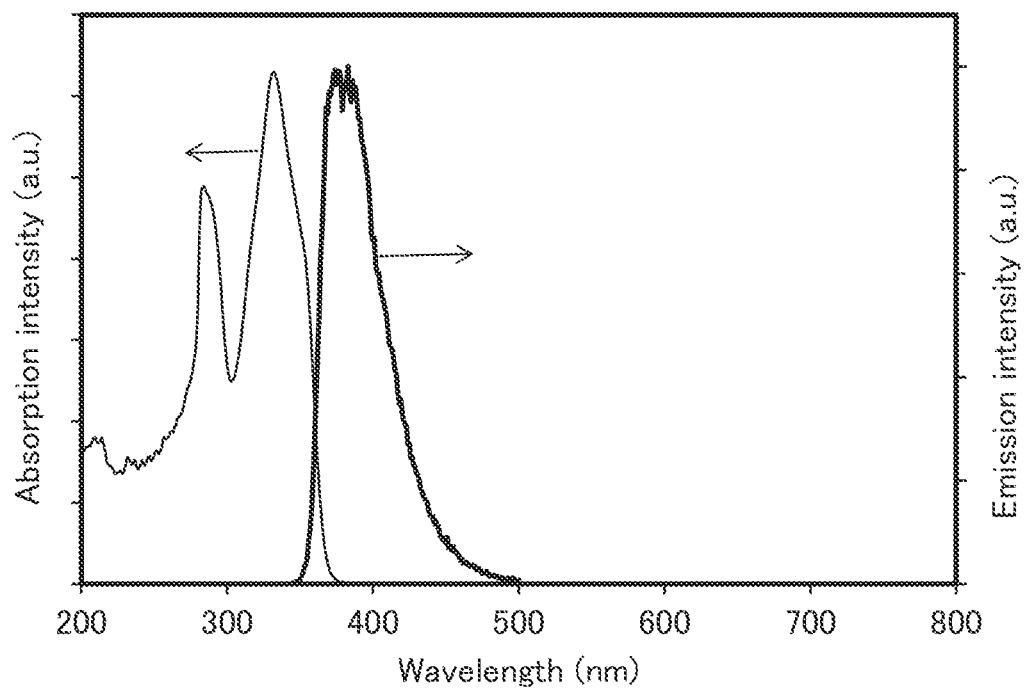
FIGS. 10A and 10B each show an ultraviolet-visible absorption spectrum and an emission spectrum of the organic compound represented by Structural Formula (100)

Next, FIG. 10A shows absorption and emission spectra of 88mDBtBPNfpm in a toluene solution. The horizontal axis represents wavelength and the vertical axes represent absorption intensity and emission intensity.

The absorption spectrum was measured using an ultraviolet-visible light spectrophotometer (V-550, produced by JASCO Corporation). The absorption spectrum of 8mDBtBPNfpm in the toluene solution was obtained by subtracting absorption spectra of toluene and a quartz cell from an absorption spectrum of the toluene solution of 8mDBtBPNfpm put in the quartz cell. The emission spectrum was measured with a PL-EL measurement apparatus (produced by Hamamatsu Photonics K.K.). The emission spectrum of 8mDBtBPNfpm in the toluene solution was measured with the toluene solution of 8mDBtBPNfpm put in a quartz cell.

FIG. 10A shows that 8mDBtBPNfpm in the toluene solution has absorption peaks at around 284 nm, 330 nm, and 353 nm and an emission wavelength peak at around 374 nm (the excitation wavelength: 330 nm).

Figure 10B:
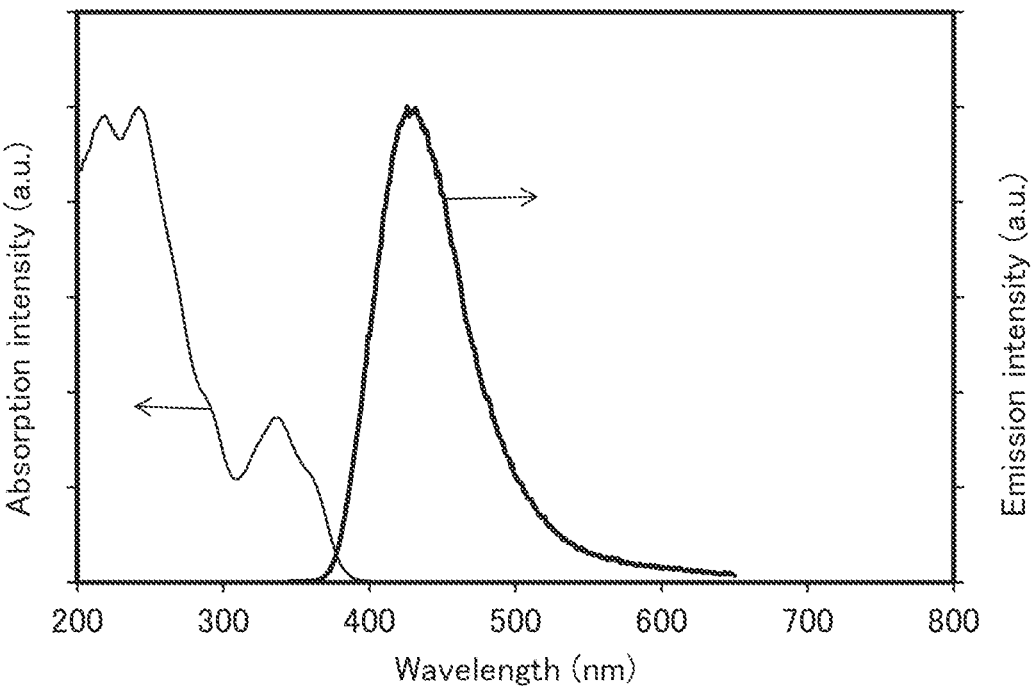

Next, absorption and emission spectra of 8mDBtBPNfpm in a solid thin film were measured. The solid thin film was formed over a quartz substrate by a vacuum evaporation method. The absorption spectrum of the thin film was calculated using an absorbance ($-\log_{10}$ [% T/(100−% R)]) obtained from a transmittance and a reflectance of a substrate and the thin film. Note that % T represents transmittance and % R represents reflectance. The absorption spectrum was measured using an ultraviolet-visible light spectrophotometer (U-4100, produced by Hitachi High-Technologies Corporation). The emission spectrum was measured using a fluorescence spectrophotometer (FS920, produced by Hamamatsu Photonics K.K.). FIG. 10B shows the measurement results of the obtained absorption and emission spectra of the solid thin film. The horizontal axis represents wavelength and the vertical axes represent absorption intensity and emission intensity.

FIG. 10B shows that 8mDBtBPNfpm in the solid thin film has absorption peaks at around 218 nm, 242 nm, 270 nm, 292 nm, 336 nm, and 363 nm, and an emission wavelength peak at around 429 nm (the excitation wavelength: 340 nm).

Next, 8mDBtBPNfpm obtained in this example was analyzed by liquid chromatography mass spectrometry (LC/MS).

In the analysis by LC/MS, liquid chromatography (LC) separation was carried out with UltiMate 3000 produced by Thermo Fisher Scientific K.K., and the MS analysis was carried out with Q Exactive produced by Thermo Fisher Scientific K.K.

In the LC separation, a given column was used at a column temperature of 40° C., and solution sending was performed in such a manner that an appropriate solvent was selected, the sample was prepared by dissolving 8mDBtBPNfpm in an organic solvent at a given concentration, and the injection amount was 5.0 μL.

A component with m/z of 554.15, which is an ion derived from 8mDBtBPNfpm, was subjected to the $MS^2$ analysis by a Targeted-$MS^2$ method. For Targeted-$MS^2$, the mass range of a target ion was set to m/z=554.15±2.0 (isolation window=4) and detection was performed in a positive mode. Measurement was performed with energy (normalized collision energy: NCE) for accelerating a target ion in a collision cell set to 60. The obtained MS spectrum is shown in FIG. 11.

Figure 11:
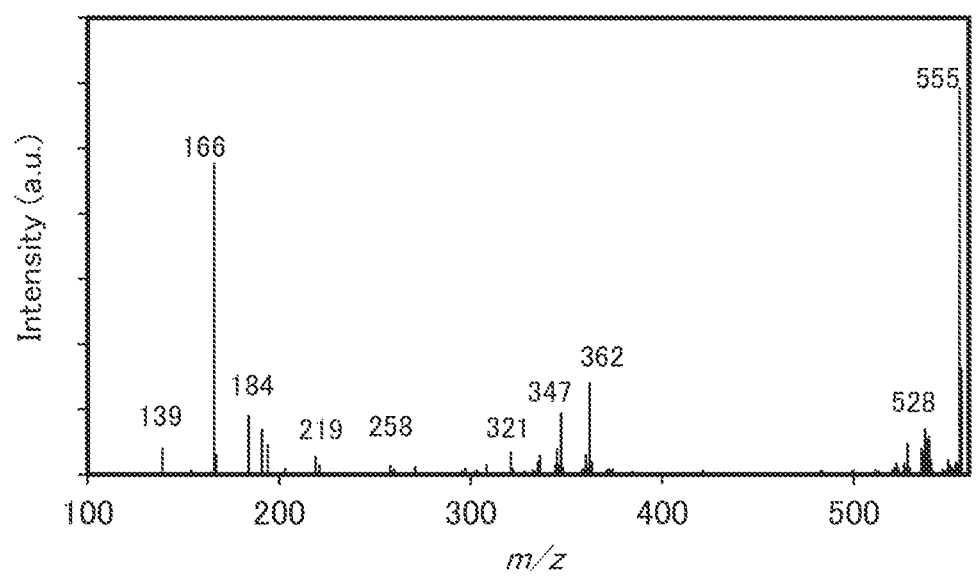
FIG. 11 shows UHPLC results of the organic compound represented by Structural Formula (100)

FIG. 11 shows that product ions of 8mDBtBPNfpm are mainly detected around m/z=528, 362, 347, 321, 258, 219, 184, 166, and 139. Note that the results in FIG. 11 show characteristics derived from 8mDBtBPNfpm and thus can be regarded as important data for identifying 8mDBtBPNfpm contained in the mixture.

It is presumed that the product ion around m/z=528 is a cation generated due to dissociation of nitrile by cleavage of a pyrimidine ring in 8mDBtBPNfpm, the product ion around m/z=362 is a cation generated due to dissociation of naphthofuran, the product ion around m/z=347 is a cation of diphenyldibenzothiophene, and the product ion around m/z=258 is a cation of phenyldibenzothiophene. These data suggest that 8mDBtBPNfpm includes a naphthofuropyrimidine group and a phenyldibenzothiophene ring or a diphenyldibenzothiophene ring.

It is also presumed that the product ion around m/z=219 is a cation generated due to dissociation of biphenyldibenzothiophene in 8mDBtBPNfpm, the product ion around m/z=184 is a cation generated due to dissociation of ethylamine by cleavage of a pyrimidine ring, the product ion around m/z=166 is a cation generated due to further dissociation of hydroxy, and the product ion around m/z=139 is a cation generated due to further dissociation of nitrile. These data suggest that 8mDBtBPNfpm includes a pyrimidine ring.

Example 2

Synthesis Example 2

This example describes a method for synthesizing 10-[3'-(dibenzothiophen-4-yl)(1,1'-biphenyl-3-yl)]naphtho[2', 1': 4,5]furo[3,2-d]pyrimidine (abbreviation: 10mDBtBPNfpm (II)), which is the organic compound of one embodiment of the present invention and represented by Structural Formula (101) in Embodiment 1. The structure of 10mDBtBPNfpm (II) is shown below.

[Chemical Formula 33]

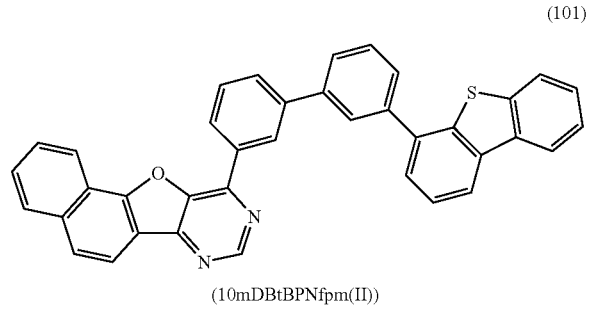

(101)

(10mDBtBPNfpm(II))

Step 1: Synthesis of ethyl 3-amino-naphtho[1,2-b]furan-2-carboxylate

First, 4.9 g of 1-hydroxynaphthalene-2-carbonitrile and 8.1 g of potassium carbonate were put into a flask, the atmosphere in the flask was replaced with nitrogen, 40 mL of DMF and 4.9 g of ethyl bromoacetate were added, and the mixture was heated at 80° C. for 15 hours. The obtained reaction mixture was added to 100 mL of iced water for rapid cooling, the mixture was stirred for 2 hours, and then filtered. The obtained residue was washed with water, and recrystallized with ethanol and water, whereby 5.2 g of a target substance (a gray solid) was obtained in a yield of 70%. A synthesis scheme of Step 1 is shown in (b-1) below.

[Chemical Formula 34]

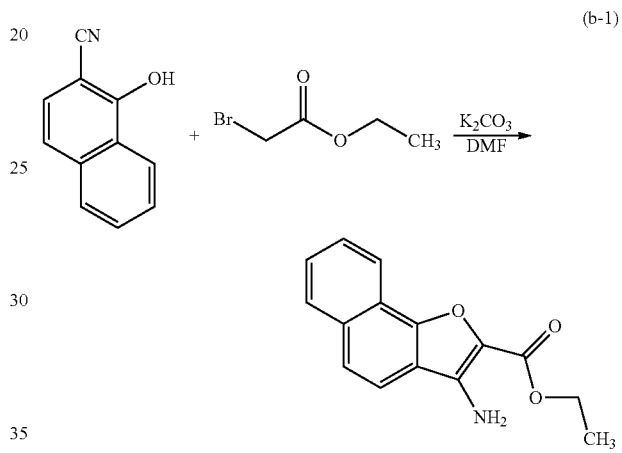

(b-1)

Step 2: Synthesis of naphtho[2', 1': 4,5]furo[3,2-d]pyrimidin-10(9H)-one

Next, 5.2 g of ethyl 3-amino-naphtho[1,2-b]furan-2-carboxylate synthesized in Step 1, 4.2 g of formamidine acetate, and 28 mL of formamide were put into a flask, and the mixture was heated at 160° C. for 5 hours. To the obtained reaction mixture was added 100 mL of water and the mixture was filtered. The residue was washed with water to give 4.8 g of a target substance (a brown solid) in a yield of 95%. A synthesis scheme of Step 2 is shown in (b-2) below.

[Chemical Formula 35]

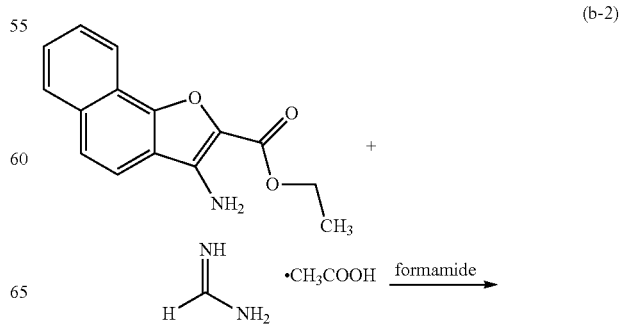

(b-2)

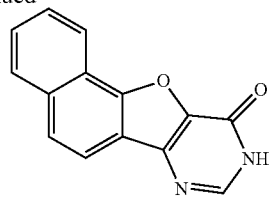

Step 3: Synthesis of 10-chloro-naphtho[2', 1': 4,5]furo[3,2-d]pyrimidine

Next, 4.6 g of naphtho[2', 1': 4,5]furo[3,2-d]pyrimidin-10(9H)-one synthesized in Step 2 and 18 mL of phosphoryl chloride were put into a flask, and the mixture was heated under a nitrogen stream at 100° C. for 7 hours. The obtained reaction mixture was added to 100 mL of iced water for rapid cooling, 400 mL of a 3M sodium hydroxide aqueous solution was added, and the mixture was stirred for an hour. This mixture was filtered and the residue was washed with ethanol to give 3.9 g of a target substance (a brown solid) in a yield of 78%. A synthesis scheme of Step 3 is shown in (b-3) below.

[Chemical Formula 36]

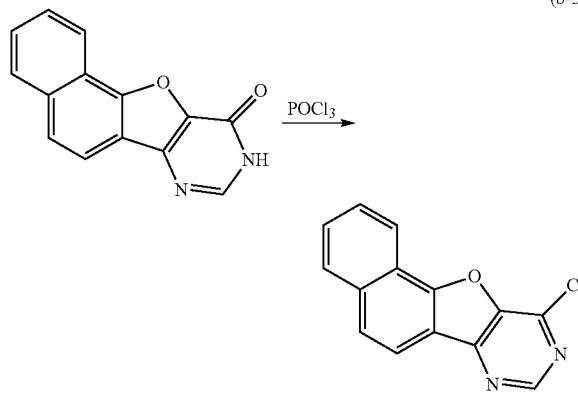

(b-3)

Step 4: Synthesis of 10-[3'-(dibenzothiophen-4-yl)(,1'-biphenyl-3-yl)]naphtho[2', 1': 4,5]furo[3,2-d]pyrimidine (abbreviation: 10mDBtBPNfpm(II))

Next, 1.8 g of 10-chloro-naphtho[2', 1': 4,5]furo[3,2-d]pyrimidine synthesized in Step 3, 1.2 g of 3-(dibenzothiophen-4-yl)phenylboronic acid, 15 mL of a 2M potassium carbonate aqueous solution, 150 mL of toluene, and 15 mL of ethanol were put into a flask, and the atmosphere in the flask was replaced with nitrogen. To this mixture was added 0.49 g of bis(triphenylphosphine)palladium(II) dichloride, and the mixture was heated under a nitrogen stream at 95° C. The obtained reaction mixture was filtered and the obtained residue was washed with water and then with ethanol.

Then, the obtained residue was dissolved in toluene, the mixture was purified through a filter aid in which Celite, alumina, and Celite were stacked in this order, and then recrystallized with toluene, whereby 1.8 g of a target pale yellow solid was obtained in a yield of 47%. A synthesis scheme of Step 4 is shown in (b-4) below.

[Chemical Formula 37]

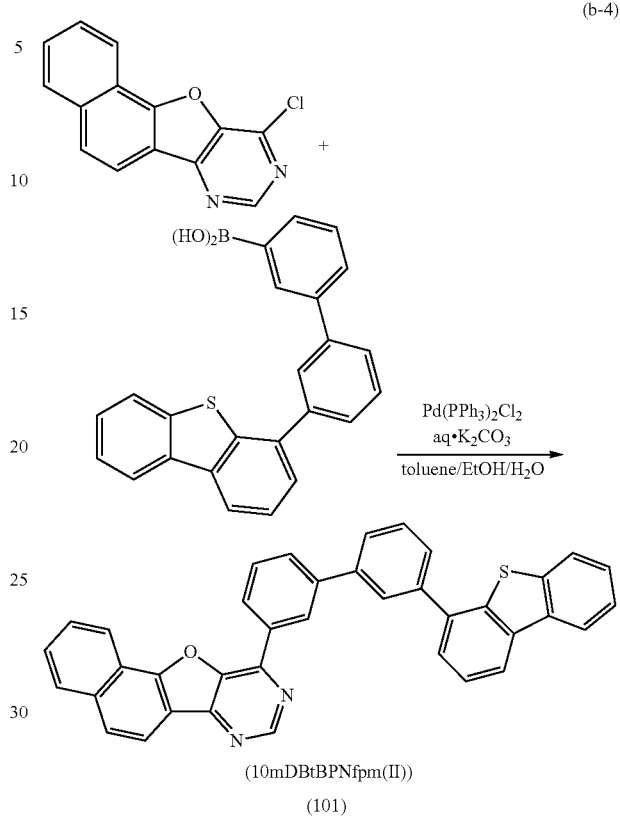

(b-4)

(10mDBtBPNfpm(II))
(101)

By a train sublimation method, 1.8 g of the obtained pale yellow solid was purified. In the purification by sublimation, the pale yellow solid was heated at 300° C. under a pressure of 2.0 Pa with an argon flow rate of 10 mL/min. After the purification by sublimation, 1.6 g of a pale yellow solid was obtained at a collection rate of 89%.

Figure 12:
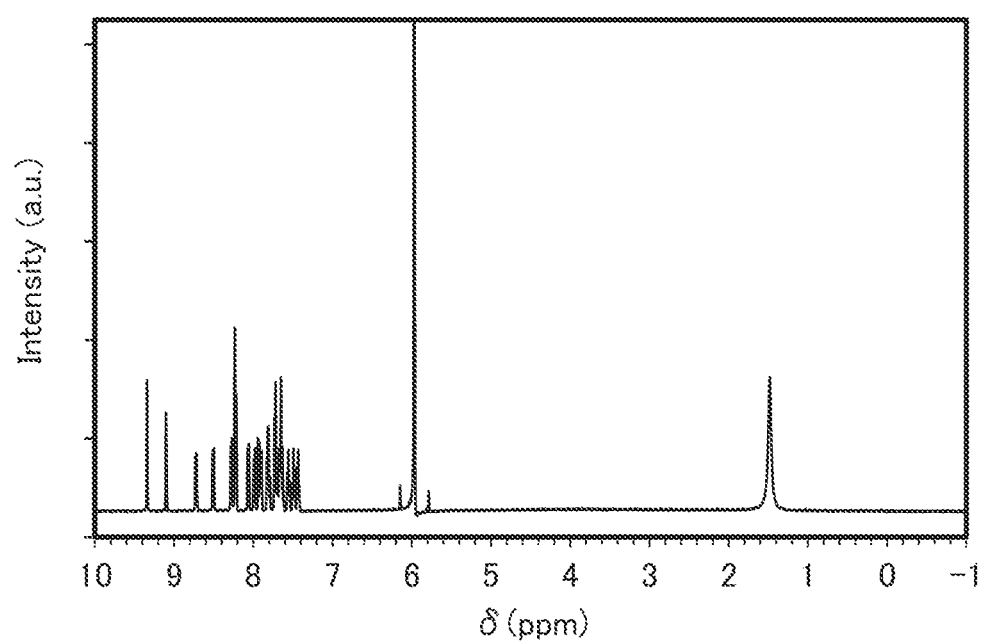
FIG. 12 is a $^1$H-NMR chart of an organic compound represented by Structural Formula (101)

Analysis results by nuclear magnetic resonance ($^1$H-NMR) spectroscopy of the obtained pale yellow solid are shown below. FIG. 12 is a $^1$H-NMR chart. The $^1$H-NMR chart revealed that 10mDBtBPNfpm(II), the organic compound represented by Structural Formula (101), was obtained in this example.

$^1$H-NMR δ (TCE-d2): 7.42-7.45 (t, 1H), 7.48-7.50 (t, 1H), 7.54-7.57 (t, 1H), 7.62-7.73 (m, 5H), 7.79-7.83 (m, 2H), 7.90-7.94 (m, 2H), 7.99 (d, 1H), 8.06 (d, 1H), 8.22 (ds, 3H), 8.27 (d, 1H), 8.50 (d, 1H), 8.72 (d, 1H), 9.10 (s, 1H), 9.34 (s, 1H).

Example 3

Figure 13:
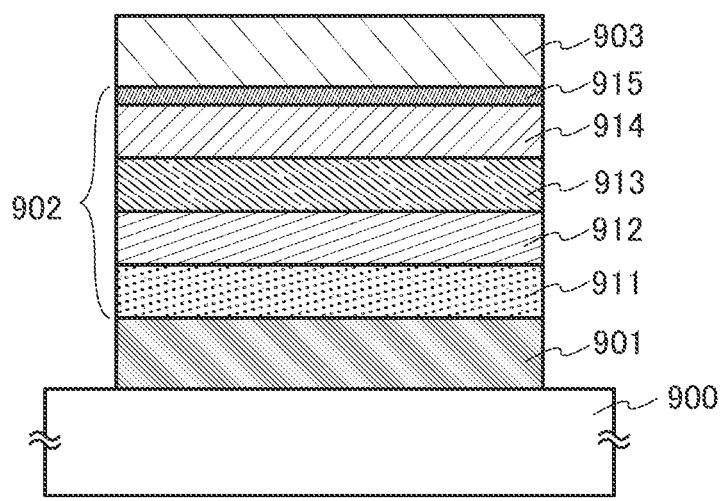
FIG. 13 illustrates a light-emitting element.

This example describes element structures, fabrication methods, and properties of a light-emitting element 1 (a light-emitting element of one embodiment of the present invention) in which 8mDBtBPNfpm (Structural Formula (100)) described in Example 1 is used in a light-emitting layer, a comparative light-emitting element 2 in which the comparative organic compound 4-[3'-(dibenzothiophen-4-yl)biphenyl-3-yl]benzofuro[3,2-d]pyrimidine (abbreviation: 4mDBTBPBfpm-II) is used in a light-emitting layer, and a comparative light-emitting element 3 in which the comparative organic compound 2-[3'-(dibenzothiophen-4-yl)biphenyl-3-yl]dibenzo[f,h]quinoxaline (abbreviation: 2mDBTBPDBq-II) is used in a light-emitting layer. Note that FIG. 13 illustrates an element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITO (70 nm) | DBT3P-II:MoOx (2:1 60 nm) | BPAFLP (20 nm) | * | 8mDBtBPNfpm (20 nm) | Bphen (10 nm) | LiF (1 nm) | Al (200 nm) |
| Comparative light-emitting element 2 | ITO (70 nm) | DBT3P-II:MoOx (2:1 60 nm) | BPAFLP (20 nm) | ** | 4mDBTBPBfpm-II (20 nm) | Bphen (10 nm) | LiF (1 nm) | Al (200 nm) |
| Comparative light-emitting element 3 | ITO (70 nm) | DBT3P-II:MoOx (2:1 60 nm) | BPAFLP (20 nm) | *** | 2mDBTBPDBq-II (20 nm) | Bphen (10 nm) | LiF (1 nm) | Al (200 nm) |

* 8mDBtBPNfpm:PCBBiF:[Ir(dppm)$_2$(acac)] (0.7:0.3:0.05 20 nm\0.8:0.2:0.05 20 nm)

** 4mDBTBPBfpm-II:PCBBiF:[Ir(dppm)$_2$(acac)] (0.7:0.3:0.05 20 nm\0.8:0.2:0.05 20 nm)

*** 2mDBTBPDBq-II:PCBBiF:[Ir(dppm)$_2$(acac)] (0.7:0.3:0.05 20 nm\0.8:0.2:0.05 20 nm)

[Chemical Formulae 38]

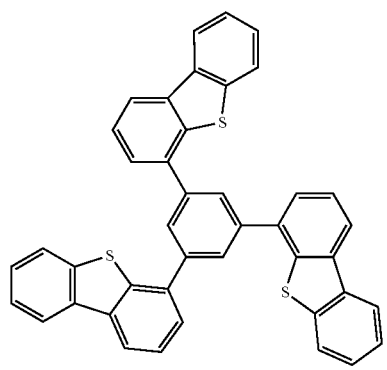

DBT3P-II

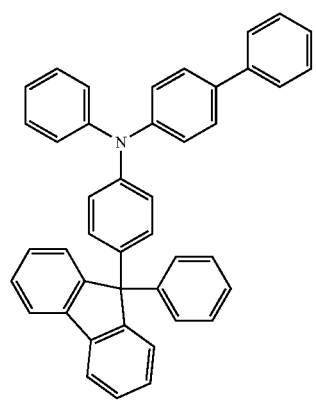

BPAFLP

TABLE 1-continued

| First electrode | Hole-injection layer | Hole-transport layer | Light-emitting layer | Electron-transport layer | Electron-injection layer | Second electrode |
| --- | --- | --- | --- | --- | --- | --- |

PCBBiF

8mDBtBPNfpm
(100)

4mDBtBPBfpmII

2mDBtBPDBqII

TABLE 1-continued

| First electrode | Hole-injection layer | Hole-transport layer | Light-emitting layer | Electron-transport layer | Electron-injection layer | Second electrode |
| --- | --- | --- | --- | --- | --- | --- |

[Ir(dppm)₂(acac)]

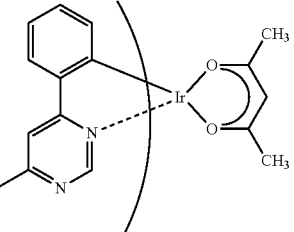

Bphen

<<Fabrication of Light-Emitting Elements>>

In each of the light-emitting elements described in this example, as illustrated in FIG. 13, a hole-injection layer 911, a hole-transport layer 912, a light-emitting layer 913, an electron-transport layer 914, and an electron-injection layer 915 were stacked in this order over a first electrode 901 formed over a substrate 900, and a second electrode 903 was stacked over the electron-injection layer 915.

First, the first electrode 901 was formed over the substrate 900. The electrode area was set to 4 mm² (2 mm×2 mm). A glass substrate was used as the substrate 900. The first electrode 901 was formed to a thickness of 70 nm using indium tin oxide (ITO) containing silicon oxide by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus where the pressure had been reduced to approximately $10^{-4}$ Pa, and was subjected to vacuum baking at 170° C. for 60 minutes in a heating chamber of the vacuum evaporation apparatus, and then the substrate was cooled down for about 30 minutes.

Next, the hole-injection layer 911 was formed over the first electrode 901. After the pressure in the vacuum evaporation apparatus was reduced to $10^{-4}$ Pa, the hole-injection layer 911 was formed by co-evaporation to have a mass ratio of 1,3,5-tri(dibenzothiophen-4-yl)benzene (abbreviation: DBT3P-II) to molybdenum oxide of 4:2 and a thickness of 60 nm.

Then, the hole-transport layer 912 was formed over the hole-injection layer 911. The hole-transport layer 912 was formed to a thickness of 20 nm by evaporation of 4-phenyl-4'-(9-phenylfluoren-9-yl)triphenylamine (abbreviation: BPAFLP).

Next, the light-emitting layer 913 was formed over the hole-transport layer 912.

The light-emitting layer 913 in the light-emitting element 1 was formed to have a thickness of 20 nm by co-evaporation of 8-[3'-(dibenzothiophen4-yl)(1,1'-biphenyl-3-yl)]naphtho[1', 2': 4,5]furo[3,2-d]pyrimidine (abbreviation: 8mDBtBPNfpm), N-(1,1'-biphenyl-4-yl)-9,9-dimethyl-N-[4-(9-phenyl-9H-carbazol-3-yl)phenyl]-9H-fluoren-2-amine (abbreviation: PCBBiF), and (acetylacetonato)bis(4,6-diphenylpyrimidinato)iridium(III) (abbreviation: [Ir(dppm)₂(acac)]) at a mass ratio of 0.7:0.3:0.05 (8mDBtBPNfpm: PCBBiF: [Ir(dppm)₂(acac)]). Furthermore, 8mDBtBPNfpm, PCBBiF, and [Ir(dppm)₂(acac)] were deposited by co-evaporation to a thickness of 20 nm with a mass ratio of 8mDBtBPNfpm to PCBBiF to [Ir(dppm)₂(acac)] being 0.8:0.2:0.05. Through the above process, the light-emitting layer 913 of the light-emitting element 1 was formed to a thickness of 40 nm.

The light-emitting layer 913 in the comparative light-emitting element 2 was formed to have a thickness of 20 nm by co-evaporation of 4-[3'-(dibenzothiophen-4-yl)biphenyl-3-yl]benzofuro[3,2-d]pyrimidine (abbreviation: 4mDBTBPBfpm-II), PCBBiF, and [Ir(dppm)₂(acac)] at a mass ratio of 0.7:0.3:0.05 (4mDBTBPBfpm-II: PCBBiF: [Ir(dppm)₂(acac)]). Furthermore, 4mDBTBPBfpm-II, PCBBiF, and [Ir(dppm)₂(acac)] were deposited by co-evaporation to a thickness of 20 nm with a mass ratio of 4mDBTBPBfpm-II to PCBBiF to [Ir(dppm)₂(acac)] being 0.8:0.2:0.05. Through the above process, the light-emitting layer 913 of the comparative light-emitting element 2 was formed to a thickness of 40 nm.

The light-emitting layer 913 in the comparative light-emitting element 3 was formed to have a thickness of 20 nm by co-evaporation of 2-[3'-(dibenzothiophen-4-yl)biphenyl-3-yl]dibenzo[f,h]quinoxaline (abbreviation: 2mDBTBPDBq-II), PCBBiF, and [Ir(dppm)₂(acac)] at a mass ratio of 0.7:0.3:0.05 (2mDBTBPDBq-II: PCBBiF: [Ir(dppm)₂(acac)]). Furthermore, 2mDBTBPDBq-II, PCBBiF, and [Ir(dppm)₂(acac)] were deposited by co-evaporation to a thickness of 20 nm with a mass ratio of 2mDBTBPDBq-II to PCBBiF to [Ir(dppm)$_2$(acac)]being 0.8:0.2:0.05. Through the above process, the light-emitting layer 913 of the comparative light-emitting element 3 was formed to a thickness of 40 nm.

Next, the electron-transport layer 914 was formed over the light-emitting layer 913. The electron-transport layer 914 in the light-emitting element 1 was formed in the following manner: 8mDBtBPNfpm and bathophenanthroline (abbreviation: Bphen) were sequentially deposited by evaporation to thicknesses of 20 nm and 10 nm, respectively. The electron-transport layer 914 in the comparative light-emitting element 2 was formed in the following manner: 4mDBTBPBfpm-II and Bphen were sequentially deposited by evaporation to thicknesses of 20 nm and 10 nm, respectively. The electron-transport layer 914 in the comparative light-emitting element 3 was formed in the following manner: 2mDBTBPDBq-II and Bphen were sequentially deposited by evaporation to thicknesses of 20 nm and 10 nm, respectively.

Then, the electron-injection layer 915 was formed over the electron-transport layer 914. The electron-injection layer 915 was formed to a thickness of 1 nm by evaporation of lithium fluoride (LiF).

After that, the second electrode 903 was formed over the electron-injection layer 915. The second electrode 903 was formed using aluminum to a thickness of 200 nm by an evaporation method. In this example, the second electrode 903 functioned as a cathode.

Through the above steps, the light-emitting elements in each of which an EL layer 902 was provided between a pair of electrodes over the substrate 900 were fabricated. The hole-injection layer 911, the hole-transport layer 912, the light-emitting layer 913, the electron-transport layer 914, and the electron-injection layer 915 described above were functional layers forming the EL layer of one embodiment of the present invention. Furthermore, in all the evaporation steps in the above fabrication method, evaporation was performed by a resistance-heating method.

Each of the light-emitting elements fabricated as described above was sealed using another substrate (not illustrated) in such a manner that the substrate (not illustrated) with an ultraviolet curable sealant was fixed to the substrate 900 in a glove box containing a nitrogen atmosphere, and the substrates were bonded to each other with the sealant attached to the periphery of the light-emitting element formed over the substrate 900. At the time of sealing, the sealant was irradiated with ultraviolet light having a wavelength of 365 nm at 6 J/cm$^2$ and heated at 80° C. for 1 hour, so that the sealant was stabilized.

<<Operation Characteristics of Light-Emitting Elements>>

Operation characteristics of the fabricated light-emitting elements were measured. Note that the measurement was performed at room temperature (in an atmosphere kept at 25° C.).

Table 2 shows initial values of main characteristics of the light-emitting elements at around 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 2.9 | 0.057 | 1.4 | (0.56, 0.44) | 940 | 66 | 71 | 26 |
| Comparative light-emitting element 2 | 2.7 | 0.037 | 0.92 | (0.56, 0.44) | 680 | 74 | 86 | 29 |
| Comparative light-emitting element 3 | 3.0 | 0.054 | 1.3 | (0.56, 0.44) | 950 | 70 | 74 | 28 |

The above results show that the light-emitting element 1 fabricated in this example has excellent element characteristics.

Figure 14:
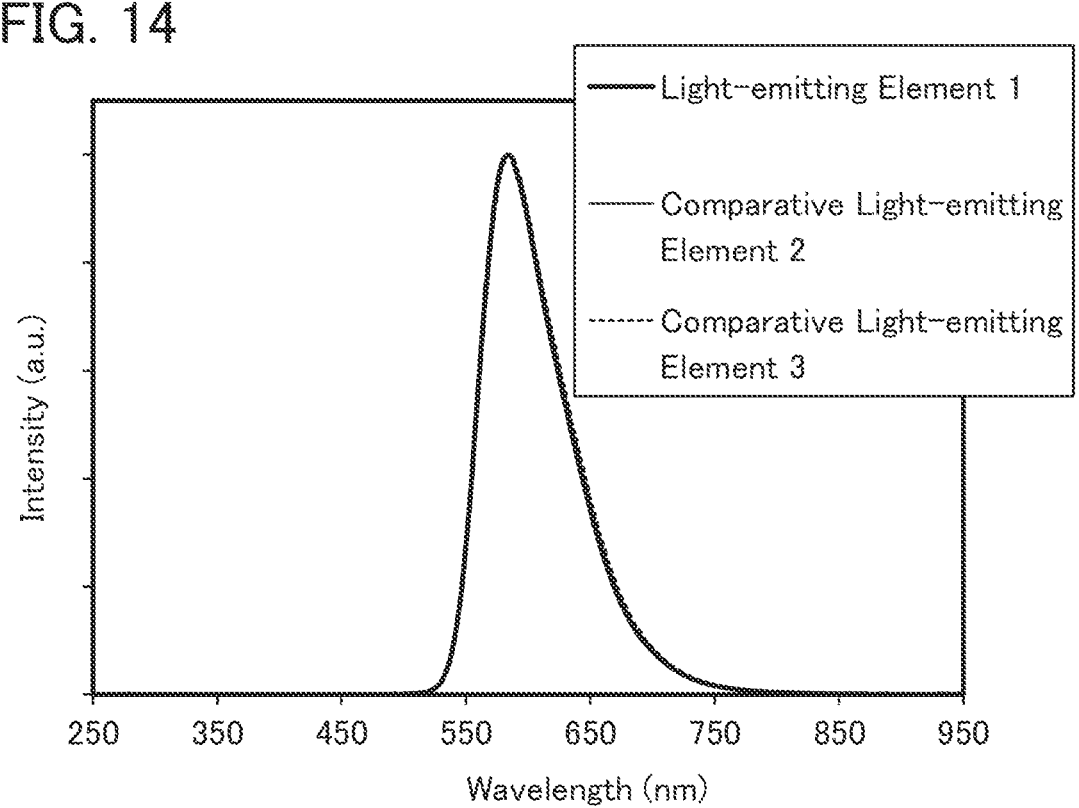
FIG. 14 shows emission spectra of a light-emitting element 1, a comparative light-emitting element 2, and a comparative light-emitting element 3.

FIG. 14 shows emission spectra of the light-emitting element 1, the comparative light-emitting element 2, and the comparative light-emitting element 3 to which current was applied at a current density of 2.5 mA/cm$^2$. As shown in FIG. 14, the emission spectrum of each of the light-emitting element 1, the comparative light-emitting element 2, and the comparative light-emitting element 3 has a peak at around 586 nm that is derived from light emission of [Ir(dppm)$_2$(acac)] contained in the light-emitting layer 913.

Figure 15:
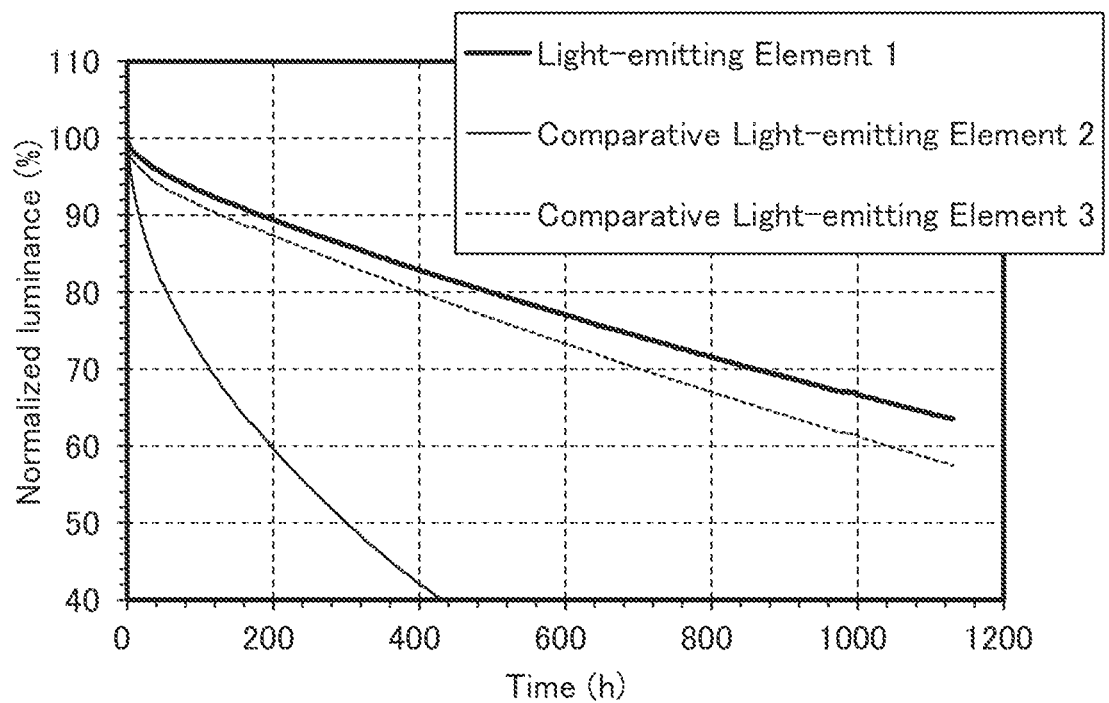
FIG. 15 shows reliability of the light-emitting element 1, the comparative light-emitting element 2, and the comparative light-emitting element 3.

Next, reliability tests were performed on the light-emitting element 1, the comparative light-emitting element 2, and the comparative light-emitting element 3. FIG. 15 shows results of the reliability tests. In FIG. 15, the vertical axis represents normalized luminance (%) with an initial luminance of 100%, and the horizontal axis represents driving time (h) of the elements. As the reliability tests, constant current driving tests at a constant current density of 50 mA/cm$^2$ were performed.

The light-emitting element of one embodiment of the present invention (the light-emitting element 1) has higher reliability than the comparative light-emitting element 2 and the comparative light-emitting element 3. The light-emitting element 1 includes, in the light-emitting layer, the organic compound (8mDBtBPNfpm) in which a hetero ring condensed with a pyrimidine ring includes a naphthyl ring, which is the specific ring structure described in Embodiment 1, whereas the comparative light-emitting element 2 includes, in the light-emitting layer, the organic compound (4mDBTBPBfpm-II) in which a hetero ring condensed with a pyrimidine ring includes a benzene ring, which is any of the ring structures other than the specific ring structure described in Embodiment 1, and the comparative light-emitting element 3 includes, in the light-emitting layer, the organic compound (2mDBTBPDBq-II) including a quinoxaline ring, which is any of the ring structures other than the ring structures described in Embodiment 1. Therefore, it is indicated that the difference in reliability of these light-emitting elements as shown in FIG. 15 is attributed to the difference in the structures of these organic compounds.

Example 4

In this example, as light-emitting elements of one embodiment of the present invention, a light-emitting element 4 including 8mDBtBPNfpm (Structural Formula (100)) described in Example 1 in a light-emitting layer and a light-emitting element 5 including 10mDBtBPNfpm(II) (Structural Formula (101)) in a light-emitting layer were fabricated. The measurement results of the properties of these light-emitting elements are shown.

Element structures of the light-emitting elements used in this example are similar to the element structure described in Example 3 with reference to FIG. 13, and Table 3 shows specific structures of layers in the element structures. Chemical formulae of materials used in this example are shown below.

TABLE 3

|  | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 4 | ITSO (70 nm) | DBT3P-II:MoOx (2:1 45 nm) | PCBBi1BP (20 nm) | * | 8mDBtBPNfpm (20 nm) | NBphen (15 nm) | LiF (1 nm) | Al (200 nm) |
| Light-emitting element 5 | ITSO (70 nm) | DBT3P-II:MoOx (2:1 45 nm) | PCBBi1BP (20 nm) | ** | 10mDBtBPNfpm(II) (20 nm) | NBphen (15 nm) | LiF (1 nm) | Al (200 nm) |

* 8mDBtBPNfpm:PCCP:[Ir(ppy)$_2$(mdppy)] (0.6:0.4:0.1 40 nm)

** 10mDBtBPNfpm(II):PCCP:[Ir(ppy)$_2$(mdppy)] (0.7:0.3:0.1 40 nm)

[Chemical Formulae 39]

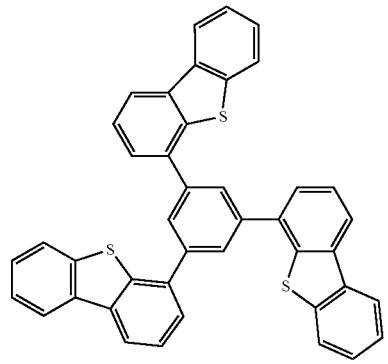

DBT3P-II

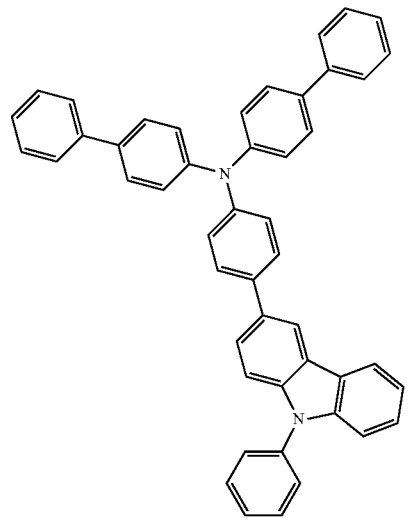

PCBBi1BP

TABLE 3-continued
| First electrode | Hole-injection layer | Hole-transport layer | Light-emitting layer | Electron-transport layer | Electron-injection layer | Second electrode |
|---|---|---|---|---|---|---|
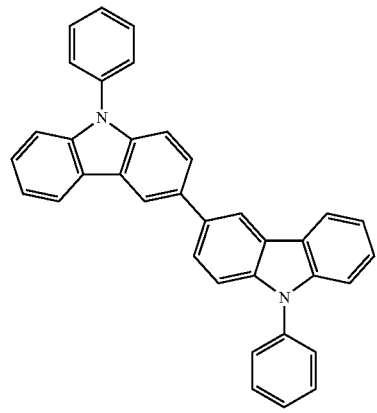
PCCP
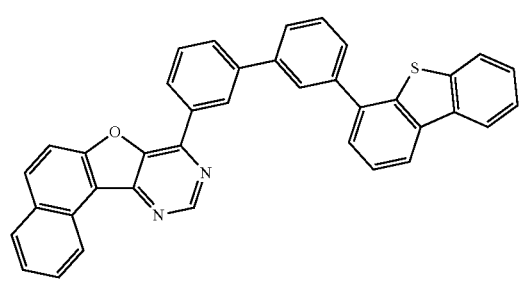
8mDBtBPNfpm
(100)
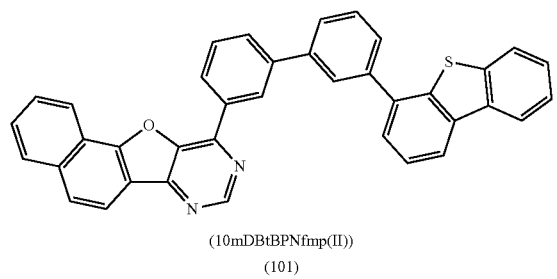 [SMILES: c1cc(-c2cccc(-c3cccc4c3sc3ccccc34)c2)cc(-c2ncnc3c2oc2c4ccccc4ccc32)c1]
(10mDBtBPNfmp(II))
(101)
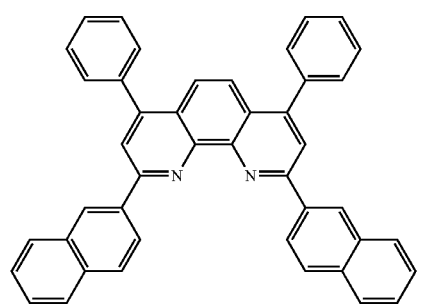
NBphen TABLE 3-continued

| First electrode | Hole-injection layer | Hole-transport layer | Light-emitting layer | Electron-transport layer | Electron-injection layer | Second electrode |
|---|---|---|---|---|---|---|

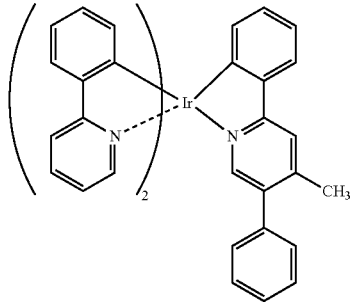

[Ir(ppy)$_2$(mdppy)]

<<Operation Characteristics of Light-Emitting Elements>>

Operation characteristics of the light-emitting element 4 and the light-emitting element 5 were measured. Note that the measurement was performed at room temperature (in an atmosphere kept at 25° C.).

Table 4 shows initial values of main characteristics of the light-emitting elements at around 1000 cd/m$^2$.

TABLE 4

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 4 | 3 | 0.048 | 1.2 | (0.35, 0.62) | 870 | 73 | 77 | 20 |
| Light-emitting element 5 | 3.1 | 0.062 | 1.50 | (0.32, 0.64) | 1100 | 74 | 75 | 20 |

The above results show that the light-emitting element 4 and the light-emitting element 5 fabricated in this example have high efficiency.

Figure 16:
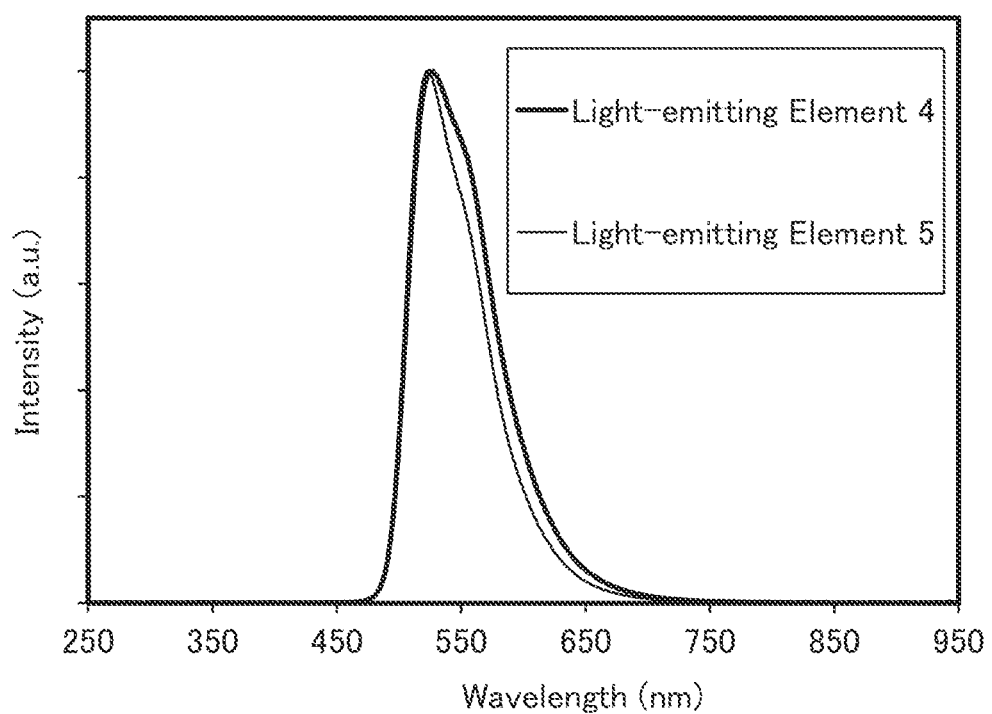
FIG. 16 shows emission spectra of a light-emitting element 4 and a light-emitting element 5.

FIG. 16 shows the emission spectra of the light-emitting element 4 and the light-emitting element 5 to which current was applied at a current density of 2.5 mA/cm$^2$. As shown in FIG. 16, the emission spectrum of each of the light-emitting elements has a peak at around 522 nm that is derived from light emission of [2-(4-methyl-5-phenyl-2-pyridinyl-κN)phenyl-κC]bis[2-(2-pyridinyl-1IV)phenyl-κC] iridium (abbreviation: [Ir(ppy)$_2$(mdppy)]) contained in the light-emitting layer 913.

Example 5

In this example, a light-emitting element 6 (a light-emitting element of one embodiment of the present invention) including 8mDBtBPNfpm (Structural Formula (100)) described in Example 1 in a light-emitting layer and a comparative light-emitting element 7 including 4-[3'-(dibenzothiophen-4-yl)biphenyl-3-yl]benzofuro[3,2-d]pyrimidine (abbreviation: 4mDBTBPBfpm-II) in a light-emitting layer were fabricated. The measurement results of the properties of these light-emitting elements are shown.

Element structures of the light-emitting elements used in this example are similar to the element structure described in Example 3 with reference to FIG. 13, and Table 5 shows specific structures of layers in the element structures. Chemical formulae of materials used in this example are shown below.

TABLE 5

| | First electrode | Hole-injection layer | Hole-transport layer | Light-emitting layer | Electron-transport layer | Electron-injection layer | Second electrode |
|---|---|---|---|---|---|---|---|
| Light-emitting element 6 | ITSO (70 nm) | DBT3P-II:MoOx (2:1 50 nm) | PCBBi1BP (20 nm) | * | 8mDBtBPNfpm (20 nm) | NBphen (15 nm) | LiF (1 nm) | Al (200 nm) |
| Comparative light-emitting element 7 | ITSO (70 nm) | DBT3P-II:MoOx (2:1 50 nm) | PCBBi1BP (20 nm) | ** | 4mDBTBPBfpm-II (20 nm) | NBphen (15 nm) | LiF (1 nm) | Al (200 nm) |

TABLE 5-continued
| First electrode | Hole-injection layer | Hole-transport layer | Light-emitting layer | Electron-transport layer | Electron-injection layer | Second electrode |
| --- | --- | --- | --- | --- | --- | --- |
\* 8mDBtBPNfpm:PCCP:[Ir(ppy)$_2$(4dppy)] (0.6:0,4:0.1 40 nm)
\*\* 4mDBTBPBfpm-II:PCCP:[Ir(ppy)$_2$(4dppy)] (0.6:0.4:0.1 40 nm)
[Chemical Formulae 40]
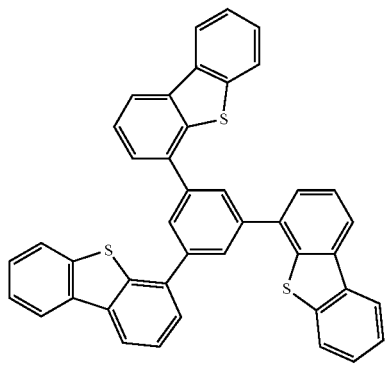
DBT3P-II
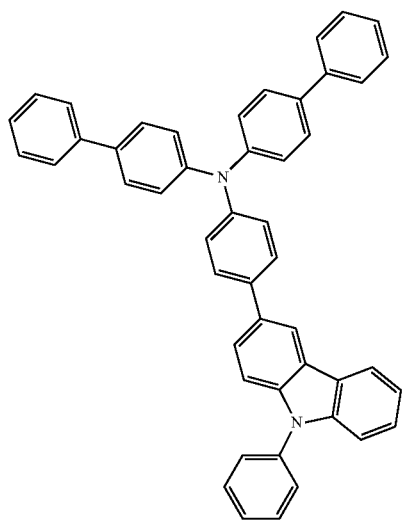
PCBBi1BP
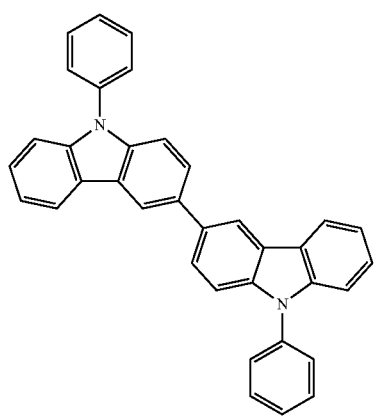
PCCP TABLE 5-continued
| First electrode | Hole-injection layer | Hole-transport layer | Light-emitting layer | Electron-transport layer | Electron-injection layer | Second electrode |
| --- | --- | --- | --- | --- | --- | --- |
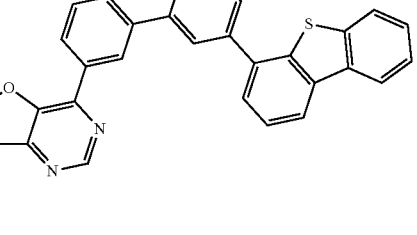
8mDBtBPNfpm
(100)
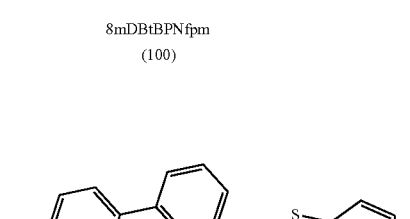
4mDBtBPBfpmII
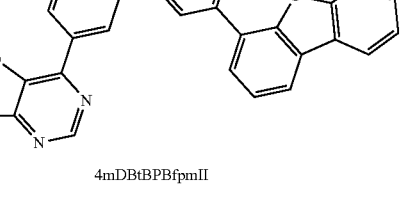
NBphen
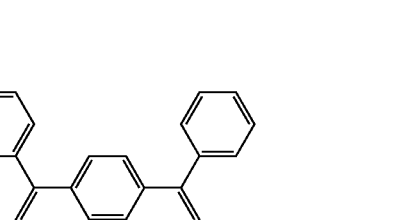
[Ir(ppy)$_2$(4dppy)]

<<Operation Characteristics of Light-Emitting Elements>>

Operation characteristics of the light-emitting element 6 and the comparative light-emitting element 7 were measured. Note that the measurement was performed at room temperature (in an atmosphere kept at 25° C.).

Table 6 shows initial values of main characteristics of the light-emitting elements at around 1000 cd/m².

TABLE 6

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 6 | 3.4 | 0.048 | 1.2 | (0.45, 0.54) | 910 | 76 | 70 | 22 |
| Comparative light-emitting element 7 | 3.4 | 0.046 | 1.2 | (0.45, 0.54) | 970 | 84 | 78 | 25 |

Figure 17:
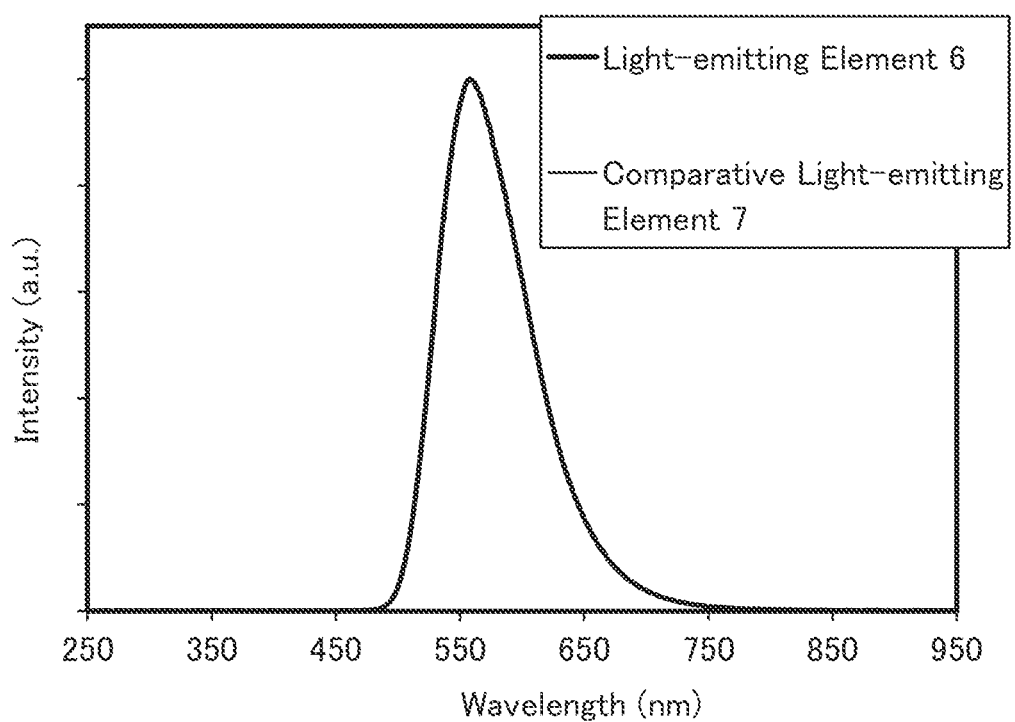
FIG. 17 shows emission spectra of a light-emitting element 6 and a comparative light-emitting element 7.

FIG. 17 shows the emission spectra of the light-emitting element 6 and the comparative light-emitting element 7 to which current was applied at a current density of 2.5 mA/cm². As shown in FIG. 17, the emission spectrum of each of the light-emitting elements has a peak at around 557 nm that is derived from light emission of bis[2-(2-pyridinyl-N)phenyl-κC][2-(4-phenyl-2-pyridinyl-κN)phenyl-κC] iridium(III) (abbreviation: [Ir(ppy)₂(4dppy)]) contained in the light-emitting layer 913.

Figure 18:
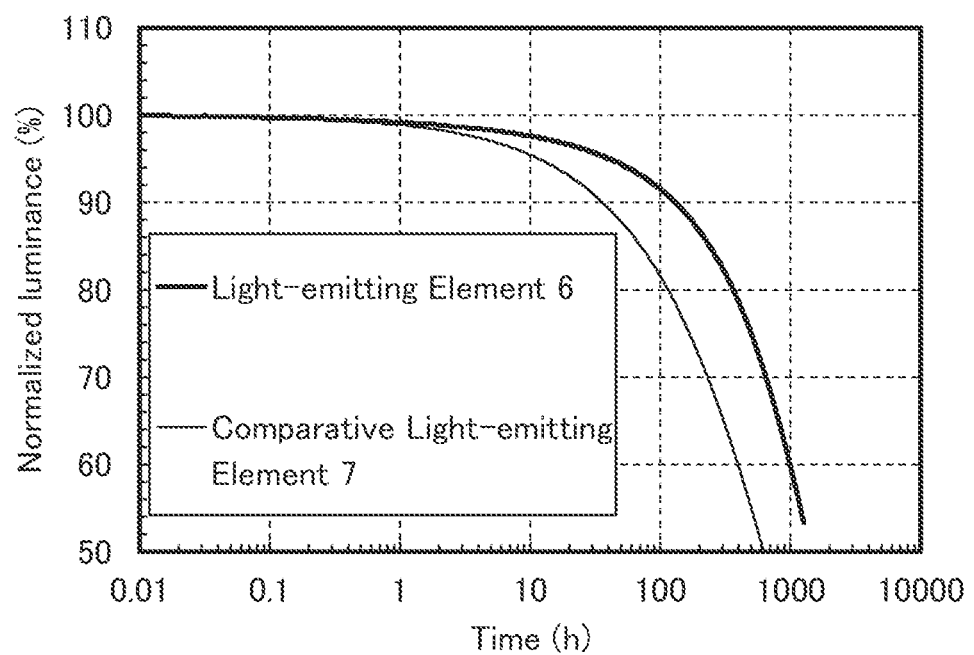
FIG. 18 shows reliability of the light-emitting element 6 and the comparative light-emitting element 7.

Next, reliability tests were performed on the light-emitting element 6 and the comparative light-emitting element 7. FIG. 18 shows results of the reliability tests. In FIG. 18, the vertical axis represents normalized luminance (%) with an initial luminance of 100%, and the horizontal axis represents driving time (h) of the elements. As the reliability tests, constant current driving tests at a constant current density of 50 mA/cm² were performed.

The results of the reliability tests show that the light-emitting element 6 has higher reliability than the comparative light-emitting element 7. Thus, 8mDBtBPNfpm (Structural Formula (100)), which is the organic compound of one embodiment of the present invention, is useful in improving the properties of the light-emitting element.

Example 6

Synthesis Example 3

This example describes a method for synthesizing 10-[3'-(dibenzothiophen-4-yl)biphenyl-3-yl]phenanthro[9', 10': 4,5]furo[3,2-d]pyrimidine (abbreviation: 10mDBtBPPnfpm), which is the organic compound of one embodiment of the present invention and represented by Structural Formula (103) in Embodiment 1. The structure of 10mDBtBPPnfpm is shown below.

[Chemical Formula 41]

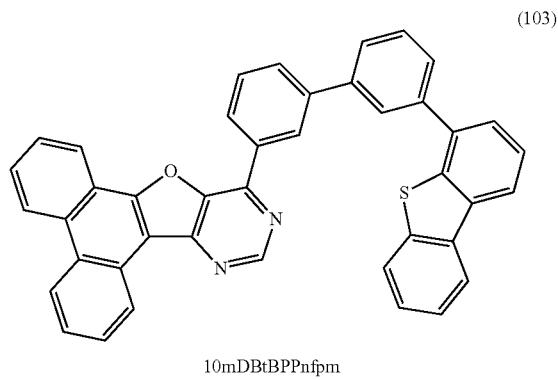

10mDBtBPPnfpm

Note that 10mDBtBPPnfpm can be synthesized by a synthesis scheme shown in (c) below.

[Chemical Formula 42]

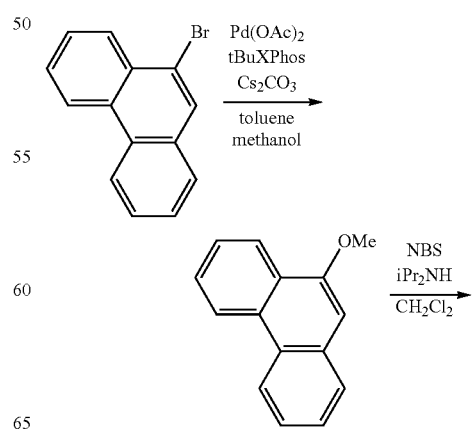

-continued

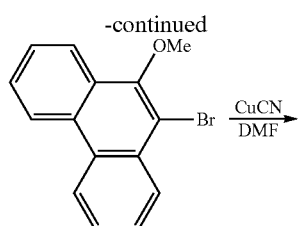

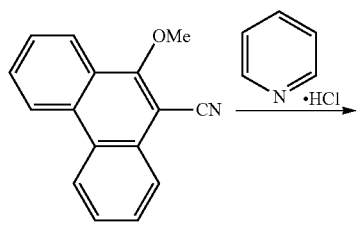

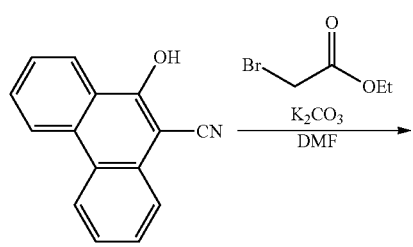

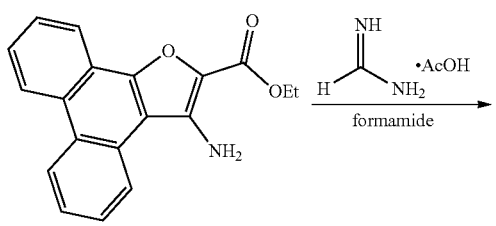

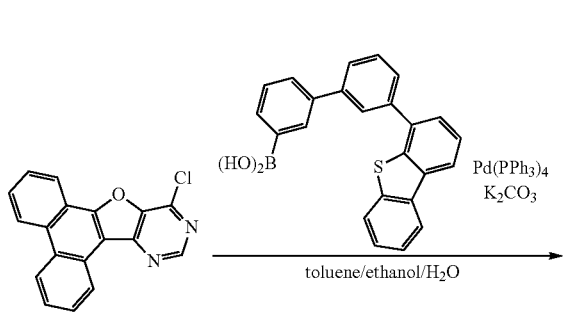

-continued

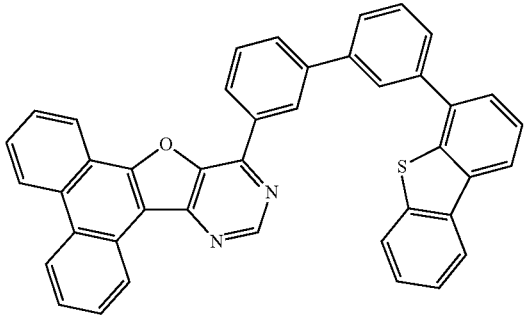

10mDBtBPPnfpm
(103)

Analysis results by nuclear magnetic resonance ($^1$H-NMR) spectroscopy of the obtained solid are shown below. The results revealed that 10mDBtBPPnfpm, the organic compound represented by Structural Formula (103), was obtained in this example.

$^1$H-NMR δ (CDCl$_3$): 7.40 (t, 1H), 7.47 (t, 1H), 7.56 (t, 1H), 7.60-7.66 (m, 3H), 7.72 (t, 1H), 7.76-7.83 (m, 4H), 7.85-7.91 (m, 2H), 7.98 (d, 1H), 8.21-8.23 (m, 2H), 8.26 (s, 1H), 8.57 (d, 1H), 8.72 (d, 1H), 8.79 (t, 2H), 9.10 (s, 1H), 9.38 (d, 1H), 9.42 (s, 1H).

REFERENCE NUMERALS

101: first electrode, 102: second electrode, 103: EL layer, 103a, 103b, and 103c: EL layer, 104: charge-generation layer, 111, 111a, and 111b: hole-injection layer, 112, 112a, and 112b: hole-transport layer, 113, 113a, 113b, and 113c: light-emitting layer, 114, 114a, and 114b: electron-transport layer, 115, 115a, and 115b: electron-injection layer, 201: first substrate, 202: transistor (FET), 203R, 203G, 203B, and 203W: light-emitting element, 204: EL layer, 205: second substrate, 206R, 206G, and 206B: color filter, 206R', 206G', and 206B': color filter, 207: first electrode, 208: second electrode, 209: black layer (black matrix), 210R and 210G: conductive layer, 301: first substrate, 302: pixel portion, 303: driver circuit portion (source line driver circuit), 304a and 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4015: diffusion plate, 4100: lighting device, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 4215: diffusion plate, 4300: lighting device, 5101: light, 5102: wheel cover, 5103: door, 5104: display portion, 5105: steering wheel, 5106: gear lever, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7012: support, 7013: earphone, 7014: antenna, 7015: shutter button, 7016: image receiving portion, 7018: stand, 7019: microphone, 7020: camera, 7021: external connection portion, 7022 and 7023: operation button, 7024: connection terminal, 7025: band, 7026: clasp, 7027: icon indicating time, 7028: another icon, 8001: lighting device, 8002: lighting device, 8003: lighting device, 8004: lighting device, 9310: portable information terminal, 9311: display portion, 9312: display region, 9313: hinge, and 9315: housing.

This application is based on Japanese Patent Application Serial No. 2017-051536 filed with Japan Patent Office on Mar. 16, 2017, the entire contents of which are hereby incorporated by reference.

The invention claimed is:

1. A light-emitting device comprising:
   a pair of electrodes; and
   a light-emitting layer between the pair of electrodes,
   wherein the light-emitting layer comprises a first organic compound, a second organic compound, and a light-emitting substance,
   wherein the first organic compound and the second organic compound form an exciplex,
   wherein the first organic compound is represented by General Formula (G2):

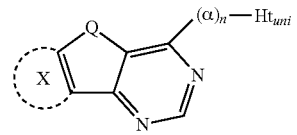

(G2)

wherein α represents a substituted or unsubstituted phenylene group,
wherein n represents an integer of 0 to 4,
wherein $Ht_{uni}$ comprises a pyrrole ring structure, a furan ring structure, or a thiophene ring structure,
wherein Q represents oxygen or sulfur, and
wherein the ring X represents a substituted or unsubstituted naphthalene ring or a substituted or unsubstituted phenanthrene ring.

2. The light-emitting device according to claim 1, wherein General Formula (G2) is represented by General Formula (G5):

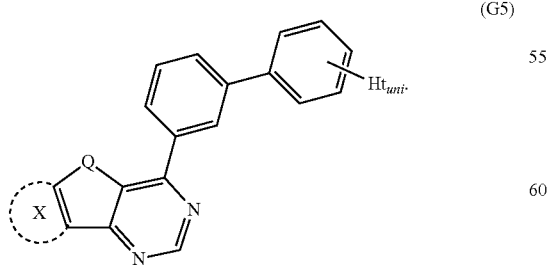

(G5)

3. The light-emitting device according to claim 1, wherein $Ht_{uni}$ is represented by any one of General Formulae (Ht-1) to (Ht-7),

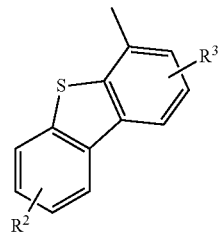
(Ht-1)

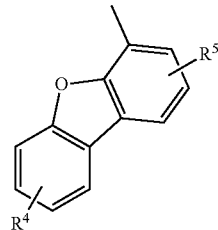
(Ht-2)

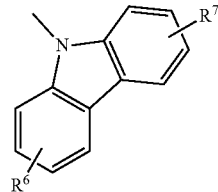
(Ht-3)

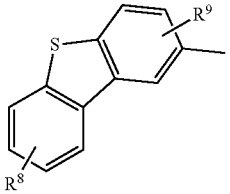
(Ht-4)

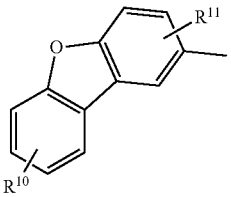
(Ht-5)

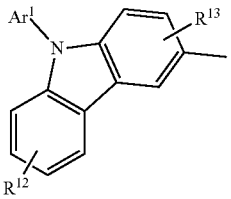
(Ht-6)

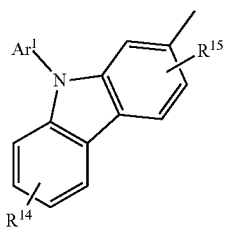
(Ht-7)

wherein $R^2$ to $R^{15}$ each represent 1 to 4 substituents and independently represent any one of hydrogen, an alkyl group having 1 to 6 carbon atoms, and a substituted or unsubstituted phenyl group, and wherein Ar¹ represents a substituted or unsubstituted aryl group having 6 to 13 carbon atoms.

4. The light-emitting device according to claim 1, wherein the ring X is represented by any one of General Formulae (X-1) to (X-4) and is condensed with an adjacent ring at a position represented by a, and

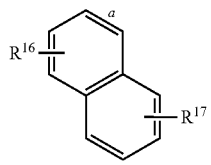
(X-1)

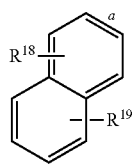
(X-2)

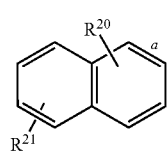
(X-3)

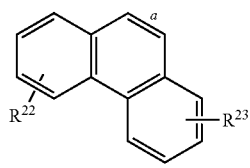
(X-4)

wherein $R^{16}$ to $R^{23}$ each represent 1 to 4 substituents and independently represent any one of hydrogen, an alkyl group having 1 to 6 carbon atoms, and a substituted or unsubstituted phenyl group.

5. The light-emitting device according to claim 1, wherein the first organic compound is represented by Structural Formula (100) or Structural Formula (101):

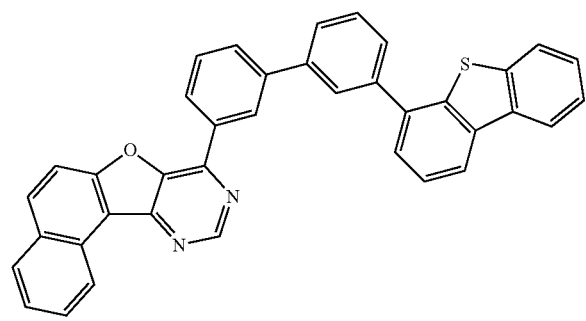
(100)

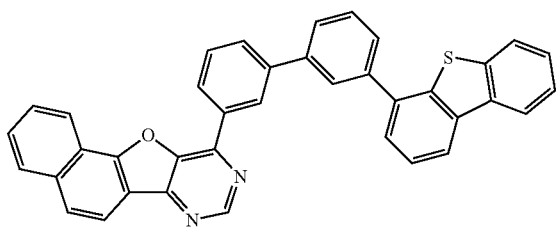
(101)

6. The light-emitting device according to claim 1, wherein the light-emitting substance is a phosphorescent material.

7. The light-emitting device according to claim 1, wherein the light-emitting substance is a thermally activated delayed fluorescence material.

8. A light-emitting device comprising:
   a pair of electrodes; and
   a light-emitting layer between the pair of electrodes,
   wherein the light-emitting layer comprises a first organic compound, a second organic compound, and a light-emitting substance,
   wherein the first organic compound and the second organic compound form an exciplex,
   wherein the first organic compound is represented by General Formula (G3):

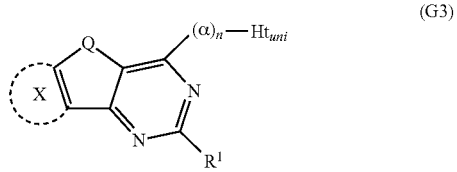
(G3)

wherein α represents a substituted or unsubstituted phenylene group, wherein n represents an integer of 1 to 4, wherein $Ht_{uni}$ comprises a pyrrole ring structure, a furan ring structure, or a thiophene ring structure, wherein R¹ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, or a substituted or unsubstituted aryl group having 6 to 13 carbon atoms, wherein Q represents oxygen or sulfur, and wherein a ring X represents a substituted or unsubstituted naphthalene ring or a substituted or unsubstituted phenanthrene ring.

9. The light-emitting device according to claim 8, wherein General Formula (G3) is represented by General Formula (G4):

(G4)

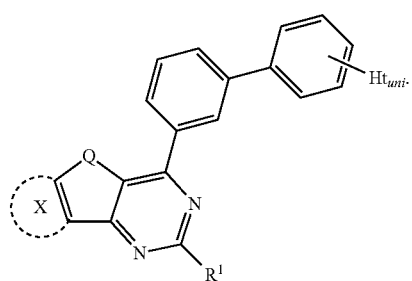

10. The light-emitting device according to claim 8, wherein Ht$_{uni}$ is represented by any one of General Formulae (Ht-1) to (Ht-7), (Ht-1)

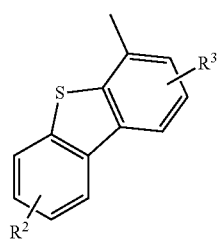

(Ht-2)

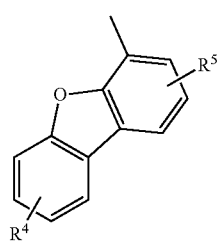

(Ht-3)

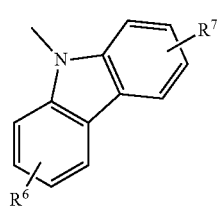

(Ht-4)

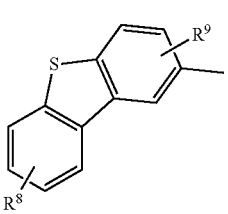

(Ht-5)

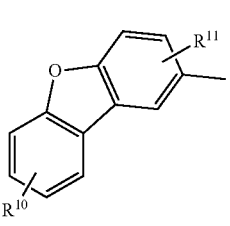

(Ht-6)

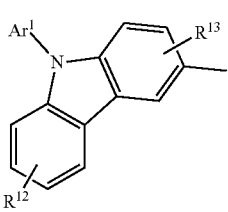

(Ht-7)

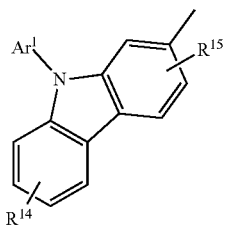

wherein $R^2$ to $R^{15}$ each represent 1 to 4 substituents and independently represent any one of hydrogen, an alkyl group having 1 to 6 carbon atoms, and a substituted or unsubstituted phenyl group, and wherein $Ar^1$ represents a substituted or unsubstituted aryl group having 6 to 13 carbon atoms.

11. The light-emitting device according to claim 8, wherein the ring X is represented by any one of General Formulae (X-1) to (X-4) and is condensed with an adjacent ring at a position represented by a, and (X-1)

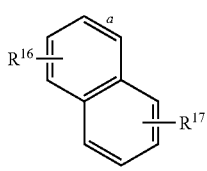

(X-2)

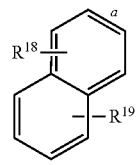

(X-3)

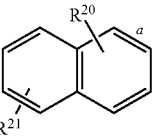

(X-4)

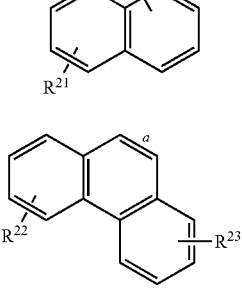

wherein $R^{16}$ to $R^{23}$ each represent 1 to 4 substituents and independently represent any one of hydrogen, an alkyl group having 1 to 6 carbon atoms, and a substituted or unsubstituted phenyl group.

12. The light-emitting device according to claim 8, wherein the light-emitting substance is a phosphorescent material.

13. The light-emitting device according to claim 8, wherein the light-emitting substance is a thermally activated delayed fluorescence material.

* * * * *